US012582410B2

(12) United States Patent
Gilhooley et al.

(10) Patent No.: US 12,582,410 B2
(45) Date of Patent: Mar. 24, 2026

(54) SURGICAL SAGITTAL BLADE CARTRIDGE

(71) Applicant: Stryker European Operations Limited, Carrigtwohill (IE)

(72) Inventors: Seamus Gilhooley, Athenry (IE); Greg McEwan, Mattawan, MI (US); Paul Shiels, Albuquerque, NM (US); Jason Karl Otto, Sioux Falls, SD (US)

(73) Assignee: Stryker European Operations Limited, Carrigtwohill (IE)

( * ) Notice: Subject to any disclaimer, the term of this patent is extended or adjusted under 35 U.S.C. 154(b) by 324 days.

(21) Appl. No.: 18/258,080

(22) PCT Filed: Dec. 20, 2021

(86) PCT No.: PCT/US2021/064328
§ 371 (c)(1),
(2) Date: Jun. 16, 2023

(87) PCT Pub. No.: WO2022/133340
PCT Pub. Date: Jun. 23, 2022

(65) Prior Publication Data
US 2025/0275771 A1 Sep. 4, 2025

Related U.S. Application Data

(60) Provisional application No. 63/251,898, filed on Oct. 4, 2021, provisional application No. 63/127,727, filed on Dec. 18, 2020.

(51) Int. Cl.
*A61B 17/14* (2006.01)
*A61B 90/94* (2016.01)
*A61B 34/20* (2016.01)

(52) U.S. Cl.
CPC ............ *A61B 17/142* (2016.11); *A61B 90/94* (2016.02); *A61B 2034/2055* (2016.02)

(58) Field of Classification Search
CPC .............................. A61B 17/14; A61B 17/142
See application file for complete search history.

(56) References Cited

U.S. PATENT DOCUMENTS 306,285 A 10/1884 Rigby et al.
683,924 A 10/1901 Fraser
(Continued)

FOREIGN PATENT DOCUMENTS

AU 2005292140 B2 7/2012
CH 654196 A5 2/1986
(Continued)

OTHER PUBLICATIONS

English Language abstract and machine-assisted English language translation for FR 2 651 114 B1 extracred from espacenet.com databse on Feb. 27, 2021, 9 pages.
(Continued)

*Primary Examiner* — Andrew Yang
(74) *Attorney, Agent, or Firm* — Howard & Howard Attorneys PLLC

(57) ABSTRACT

A surgical sagittal saw cartridge that includes a guide bar formed from an inner plate and opposed outer plates. The cartridge has a blade that extends distally from the guide bar, the blade comprising a blade head including a plurality of teeth. The plurality of teeth may include a combination of pilot teeth and base teeth, the pilot teeth configured to extend distally beyond the base teeth. The inner plate may comprise an inner tine and/or two opposed outer tines. The inner tine may be formed to define the head against which the blade is configured to pivot about. The inner plate may be configured to have opposed edges that extend beyond the opposed edges of the outer plates to define a mounting feature. The
(Continued)

inner plate may also define a reference feature configured to register and/or verify the pose of the cartridge with a navigation system.

20 Claims, 34 Drawing Sheets

(56)                References Cited

U.S. PATENT DOCUMENTS

| | | |
|---|---|---|
| 1,201,467 A | 10/1916 | Hogland |
| 1,543,195 A | 6/1925 | Thugesen et al. |
| 1,708,133 A | 4/1929 | Comparetto |
| 2,138,862 A | 12/1938 | Johnston |
| 2,702,550 A | 2/1955 | Rowe et al. |
| 2,854,981 A | 10/1958 | Morrison |
| 3,495,590 A | 2/1970 | Zeiller |
| 3,554,197 A | 1/1971 | Dobbie |
| 3,642,002 A | 2/1972 | Otterstrom |
| 3,678,934 A | 7/1972 | Warfield et al. |
| 3,734,652 A | 5/1973 | Barnett |
| 3,797,497 A | 3/1974 | Crim et al. |
| 3,835,859 A | 9/1974 | Roberts et al. |
| 3,882,737 A | 5/1975 | Crim et al. |
| 3,905,105 A | 9/1975 | Tuke |
| 3,978,862 A | 9/1976 | Morrison |
| 4,019,408 A | 4/1977 | Idel |
| 4,184,804 A | 1/1980 | Inagaki et al. |
| 4,203,444 A | 5/1980 | Bonnell et al. |
| 4,217,964 A | 8/1980 | Eaton |
| 4,246,902 A | 1/1981 | Martinez |
| 4,273,169 A | 6/1981 | Baenen |
| 4,274,414 A | 6/1981 | Johnson et al. |
| 4,461,296 A | 7/1984 | Hodge |
| 4,502,184 A | 3/1985 | Karubian |
| 4,513,742 A | 4/1985 | Arnegger |
| 4,584,999 A | 4/1986 | Amegger |
| 4,637,391 A | 1/1987 | Schlein |
| 4,683,924 A | 8/1987 | Cornelius |
| 4,700,702 A | 10/1987 | Nilsson |
| 4,708,133 A | 11/1987 | Comparetto |
| 4,892,093 A | 1/1990 | Zarnowski et al. |
| 4,941,466 A | 7/1990 | Romano |
| 5,014,430 A | 5/1991 | Wortham |
| 5,092,869 A | 3/1992 | Waldron |
| 5,100,506 A | 3/1992 | Sturtevant et al. |
| 5,122,142 A | 6/1992 | Pascaloff |
| 5,133,728 A | 7/1992 | Petersen |
| 5,135,533 A | 8/1992 | Petersen et al. |
| 5,178,626 A | 1/1993 | Pappas |
| 5,265,343 A | 11/1993 | Pascaloff |
| 5,306,285 A | 4/1994 | Miller et al. |
| 5,349,754 A | 9/1994 | Wuensch et al. |
| 5,403,318 A | 4/1995 | Boehringer et al. |
| 5,423,822 A | 6/1995 | Hershberger et al. |
| 5,439,472 A | 8/1995 | Evans et al. |
| 5,468,247 A | 11/1995 | Matthai et al. |
| 5,496,325 A | 3/1996 | McLees |
| 5,591,170 A | 1/1997 | Spievack et al. |
| 5,609,603 A | 3/1997 | Linden |
| 5,697,158 A | 12/1997 | Klinzing et al. |
| 5,725,530 A | 3/1998 | Popken |
| 5,735,866 A | 4/1998 | Adams et al. |
| 5,817,097 A | 10/1998 | Howard et al. |
| 5,846,244 A | 12/1998 | Cripe |
| 5,897,570 A | 4/1999 | Palleva et al. |
| 6,001,115 A | 12/1999 | Ahola et al. |
| 6,105,535 A | 8/2000 | Atamian et al. |
| 6,106,535 A | 8/2000 | Dross et al. |
| 6,113,618 A | 9/2000 | Nic |
| 6,860,886 B1 | 3/2005 | Lee |
| 6,875,222 B2 | 4/2005 | Long et al. |
| 6,949,110 B2 | 9/2005 | Ark et al. |
| 6,960,894 B2 | 11/2005 | Carusillo et al. |
| 7,362,228 B2 | 4/2008 | Nycz et al. |
| 7,497,860 B2 | 3/2009 | Carusillo et al. |
| 7,638,958 B2 | 12/2009 | Philipp et al. |
| 7,691,106 B2 | 4/2010 | Schenberger et al. |
| 7,704,254 B2 | 4/2010 | Walen |
| 7,744,616 B2 | 6/2010 | O'Donoghue |
| 7,748,308 B2 | 7/2010 | Anderson et al. |
| 8,043,292 B2 | 10/2011 | Carusillo |
| 8,323,285 B2 * | 12/2012 | Walen ................. A61B 17/142 |
| | | 606/82 |
| 8,403,932 B2 | 3/2013 | Carusillo et al. |
| 8,444,647 B2 | 5/2013 | Walen et al. |
| 8,672,943 B2 | 3/2014 | Fisher et al. |
| 8,685,028 B2 | 4/2014 | Kim |
| 8,696,673 B2 | 4/2014 | Walen et al. |
| 8,702,710 B2 | 4/2014 | Carusillo |
| 9,060,783 B2 | 6/2015 | Walen et al. |
| 9,072,526 B2 | 7/2015 | Carusillo |
| 9,192,390 B2 | 11/2015 | delRio et al. |
| 9,439,655 B2 | 9/2016 | Cosgrove et al. |
| 9,445,822 B2 | 9/2016 | Walen |
| 9,554,808 B2 | 1/2017 | Carusillo |
| 9,820,753 B2 | 11/2017 | Walen et al. |
| 9,848,887 B2 | 12/2017 | Carusillo et al. |
| 10,251,651 B2 | 4/2019 | Carusillo |
| 10,278,710 B2 | 5/2019 | Walen et al. |
| 10,687,823 B2 | 6/2020 | Mac an Tuile et al. |
| 10,932,794 B2 | 3/2021 | Carusillo |
| 11,083,468 B2 | 8/2021 | Carusillo |
| 11,090,061 B2 | 8/2021 | Walen et al. |
| 11,160,561 B2 | 11/2021 | MacAn Tuile et al. |
| 11,179,163 B2 | 11/2021 | Walen et al. |
| 11,241,240 B2 | 2/2022 | Mac An Tuile et al. |
| 2002/0116022 A1 | 8/2002 | Lebouitz et al. |
| 2002/0198556 A1 | 12/2002 | Ark |
| 2003/0093103 A1 | 5/2003 | Malackowski et al. |
| 2005/0020909 A1 | 1/2005 | Moctezuma de la Barrera et al. |
| 2006/0009796 A1 | 1/2006 | Carusillo et al. |
| 2006/0111723 A1 | 5/2006 | Chapolini et al. |
| 2007/0068399 A1 | 3/2007 | Anderson et al. |
| 2007/0083209 A1 | 4/2007 | Schenberger et al. |
| 2007/0085496 A1 | 4/2007 | Philipp et al. |
| 2007/0119055 A1 | 5/2007 | Walen et al. |
| 2008/0119860 A1 | 5/2008 | McCarthy |
| 2010/0292701 A1 | 11/2010 | Fisher et al. |
| 2014/0163558 A1 | 6/2014 | Cosgrove et al. |
| 2014/0194882 A1 | 7/2014 | Walen et al. |
| 2017/0348007 A1 | 12/2017 | Shiels |
| 2018/0303561 A1 | 10/2018 | McCabe et al. |
| 2019/0201003 A1 | 7/2019 | Carusillo |
| 2019/0231364 A1 | 8/2019 | Walen et al. |
| 2020/0315632 A1 | 10/2020 | Mac An Tuile et al. |
| 2021/0100561 A1 | 4/2021 | Sieh et al. |
| 2021/0113215 A1 | 4/2021 | Gisler |
| 2021/0137533 A1 | 5/2021 | Carusillo |
| 2022/0047274 A1 | 2/2022 | Walen et al. |

FOREIGN PATENT DOCUMENTS

| | | |
|---|---|---|
| CN | 1045026 A | 9/1990 |
| CN | 101791235 A | 8/2010 |
| CN | 102826549 A | 12/2012 |
| CN | 103505259 A | 1/2014 |
| CN | 103860232 A | 6/2014 |
| CN | 103505259 B | 12/2015 |
| DE | 354343 C | 6/1922 |
| DE | 478354 C | 6/1929 |
| DE | 2400696 B2 | 8/1976 |
| DE | 2615301 A1 | 10/1977 |
| DE | 2628131 A1 | 12/1977 |
| DE | 2611720 B2 | 5/1978 |
| DE | 2640267 A1 | 5/1978 |
| DE | 2935732 A1 | 3/1981 |
| DE | 2935731 A1 | 4/1981 |
| DE | 3640516 C1 | 4/1988 |
| DE | 3638404 A1 | 5/1988 |
| DE | 8906511 U1 | 7/1989 |
| DE | 4140395 A1 | 6/1993 |
| DE | 102008062880 A1 | 6/2010 |
| EP | 1880682 A2 | 1/2008 |
| FR | 2651114 B1 | 10/1991 |

(56)                   References Cited

FOREIGN PATENT DOCUMENTS

| GB | 2317510 A | 3/1998 |
| RU | 2218112 C2 | 12/2003 |
| WO | 03013371 A1 | 2/2003 |
| WO | 2004105623 A1 | 12/2004 |
| WO | 2006017066 A2 | 2/2006 |
| WO | 2006063156 A1 | 6/2006 |
| WO | 2007030793 A2 | 3/2007 |
| WO | 2007045993 A2 | 4/2007 |
| WO | 2008024717 A2 | 2/2008 |
| WO | 2013016472 A1 | 1/2013 |
| WO | 2016182981 A2 | 11/2016 |
| WO | 2017155821 A1 | 9/2017 |

OTHER PUBLICATIONS

English language abstract and machine-assisted English translation for CN 101791235 extracted from espacenet.com database on Jul. 20, 2020, 6 pages.

English language abstract and machine-assisted English translation for CN 102826549 extracted from espacenet.com database on Jul. 20, 2020, 5 pages.

English language abstract and machine-assisted English translation for CN 103505259 B extracted from espacenet.com database on Jun. 19, 2023, 9 pages.

English language abstract and machine-assisted English translation for CN 1045026 extracted from espacenet.com database on Jul. 20, 2020, 5 pages.

English language abstract and machine-assisted English translation for DE 10 2008 062 880 extracted from espacenet.com database on Dec. 11, 2017, 28 pages.

English language abstract and machine-assisted English translation for DE 2611720 B2 extracted from espacenet.com database on Feb. 17, 2021, 6 pages.

English language abstract and machine-assisted English translation for DE 2628131 A1 extracted from espacenet.com database on Feb. 17, 2021, 5 pages.

English language abstract and machine-assisted English translation for DE 2640267 A1 extracted from espacenet.com database on Feb. 17, 2021, 4 pages.

English language abstract and machine-assisted English translation for DE 2935732 A1 extracted from espace523net.com database on Feb. 17, 2021, 10 pages.

English language abstract and machine-assisted English translation for DE 3638404 A1 extracted from espacenet.com database on Feb. 17, 2021, 9 pages.

English language abstract and machine-assisted English translation for DE 3640516 C1 extracted from espacenet.com database on Feb. 17, 2021, 6 pages.

English language abstract and machine-assisted English translation for EP 1 880 682 A2 extracted from espacenet.com database on Aug. 29, 2018, 33 pages.

English language abstract and machine-assisted English translation for RU 2218112 C2 extracted from espacenet.com database on Feb. 17, 2021, 5 pages.

English language abstract and machine-assisted English translation for WO 2004/105623 A1 extracted from espacenet.com database on Feb. 17, 2021, 14 pages.

English language abstract for CN 103860232 extracted from espacenet.com database on Jul. 20, 2020, 1 page.

English language abstract for DE 4140395 A1 extracted from espacenet.com database on Feb. 17, 2021, 2 pages.

English language abstract for WO 03/013771 A1 extracted from espacenet.com databa523se on Feb. 17, 2021, 1 page.

English language abstract not found for CH 654196 A5; however, see English language equivalent U.S. Pat. No. 4,513,742. Original document extracted from espacenet.com database on Feb. 17, 2021, 4 pages. cited 523by applicant.

English language abstract not found for DE 2400696 B2; however, see English language equivalent U.S. Pat. No. 3,905,105. Original document extracted from espacenet.com database on Feb. 17, 2021, 20 pages.

International Search Report for Application No. PCT/US2016/031407 dated Jan. 10, 2017, 6 pages.

International Search Report for Application No. PCT/US2021/064328 dated Jun. 13, 2022, 3 pages.

International Search Report for PCT App. No. PCT/US2006/035204, dated Jul. 2007.

International Search Report for PCT/US2005/023769, dated Feb. 22, 2006.

Machine-Assisted English translation for DE 2615301 A1 extracted from the espacenet.com database on Feb. 17, 2021, 6 pages.

Machine-Assisted English translation for DE 354343 C extracted from the espacenet.com database on Feb. 17, 2021, 3 pages.

Machine-Assisted English translation for DE 478354 C extracted from the espacenet.com database on Feb. 17, 2021, 4 pages.

Machine-Assisted English translation for DE 8906511 U1 extracted from the espacenet.com database on Feb. 17, 2021, 10 pages.

Partial International Search Report for Application No. PCT/US2021/064328 dated Mar. 21, 2022, 2 pages.

Stryker Corporation, Opposition Against EP Pat. No. 1 880 682 B1, dated Jan. 2011, 10 pages.

EPO, "Invitation to Pay Additional Fees, dated Nov. 17, 2005, in PCT/US2005/023769, with Communication Relating to the Results of the Partial International Search (7 pages)."

* cited by examiner

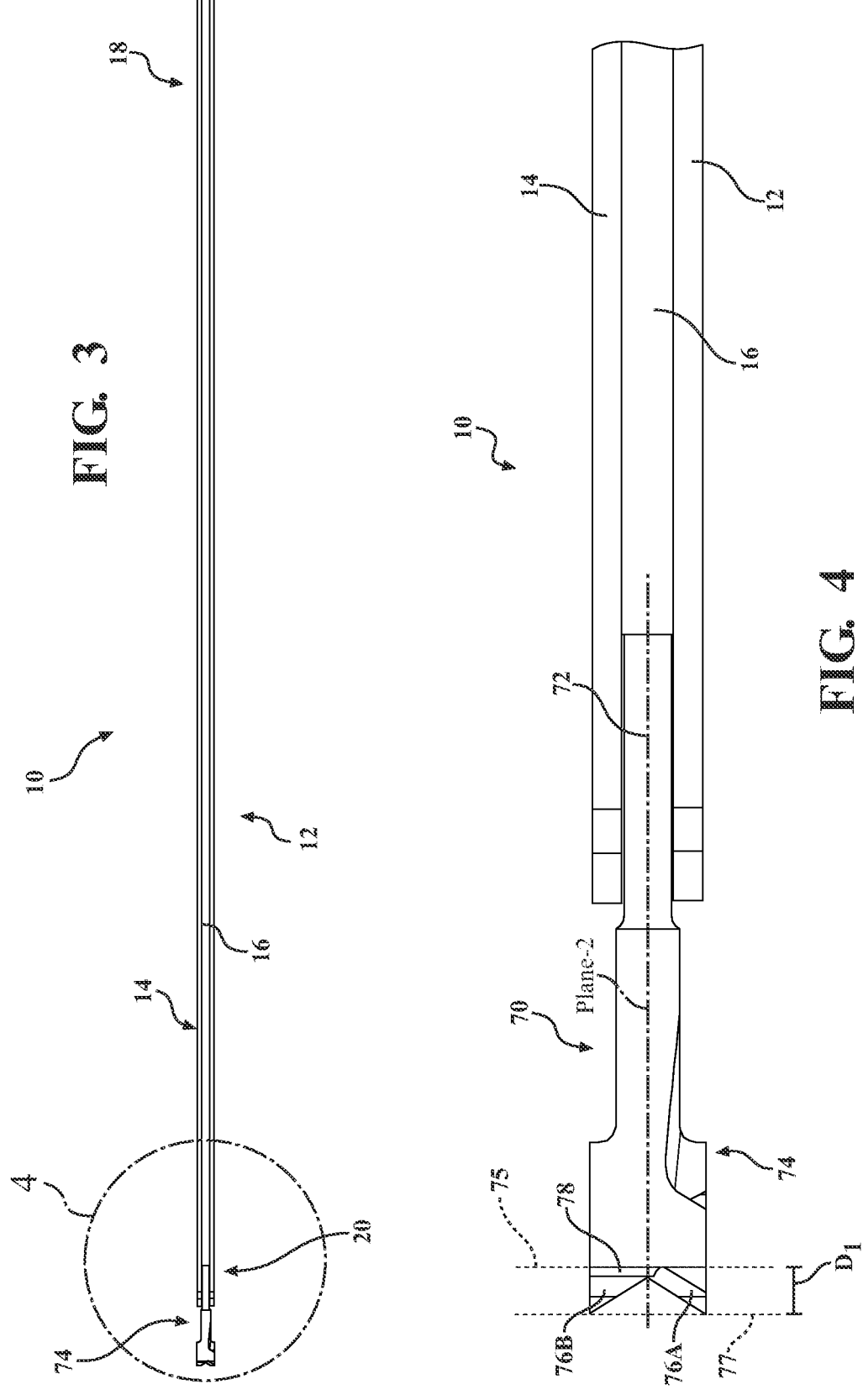

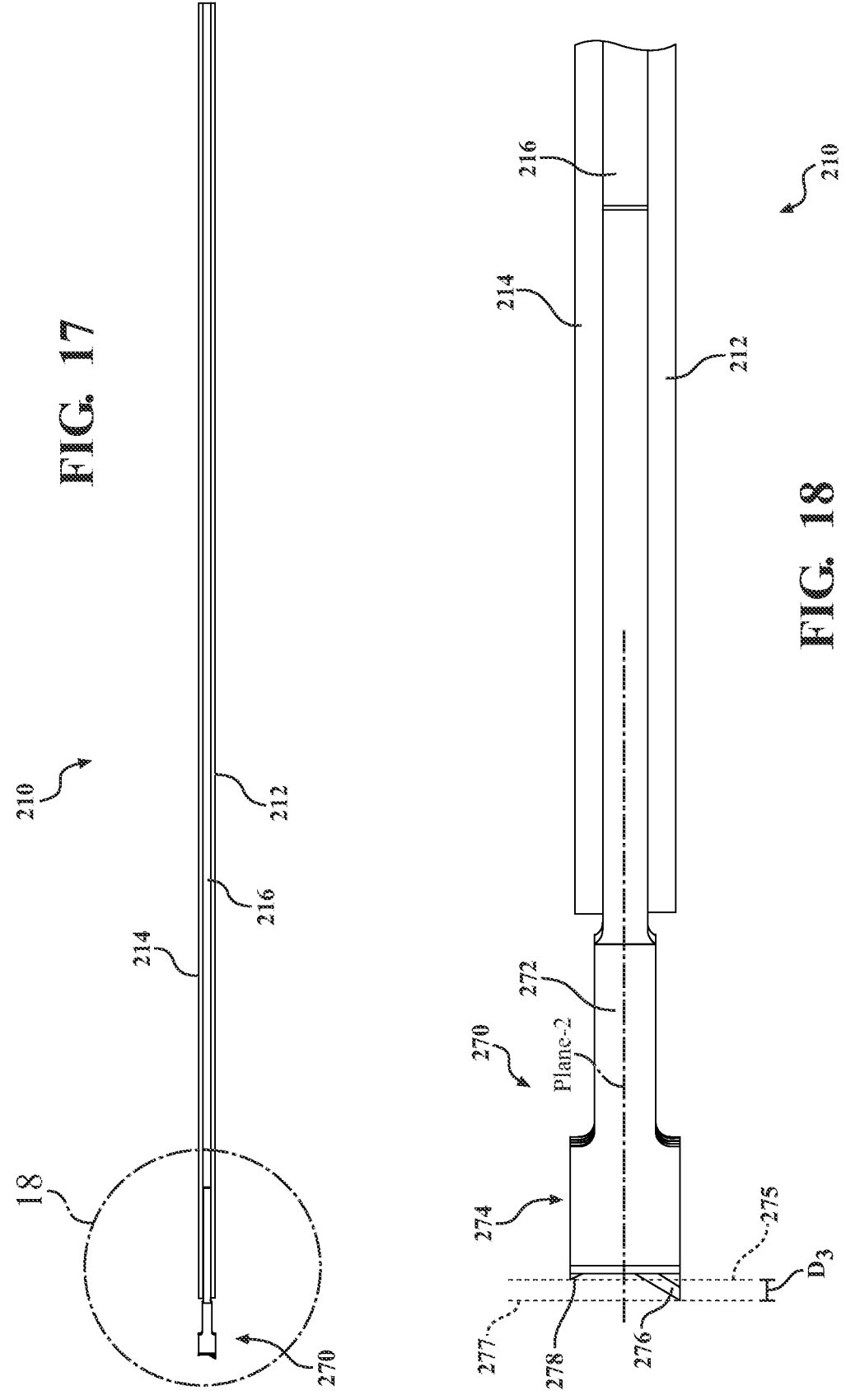

SURGICAL SAGITTAL BLADE CARTRIDGE

CROSS-REFERENCES TO RELATED APPLICATIONS

This application is a national stage of PCT International Application No. PCT/US2021/064328, filed Dec. 20, 2021, which claims the benefit of priority to U.S. Provisional Application No. 63/127,727, filed Dec. 18, 2020, and the benefit of priority to U.S. Provisional Application No. 63/251,898, filed Oct. 4, 2021, the disclosures of which are incorporated herein by reference in their entirety.

BACKGROUND

A sagittal saw blade is a surgical saw with a head that pivots around an axis that is perpendicular to the blade. PCT Pub. No. WO 2006/017066A2/U.S. Pat. No. 7,497,860, PCT Pub. No. WO 2007/030793A2/U.S. Pat. No. 7,704,254, and PCT Pub. No. WO2016/182981A2/U.S. Pat. No. 10,687,823, the contents of which are each incorporated herein by reference, each disclose a sagittal saw blade cartridge. A sagittal saw blade cartridge includes a static guide bar and a blade head. The guide bar is an elongated member that is releasably attached to the handpiece, the saw that actuates the cartridge. The blade head is pivotally mounted to the guide bar and has teeth that extend forward from the guide bar. One or more drive links extend from the blade head towards the proximal end of the guide bar. The drive links are reciprocated back and forth by a drive assembly internal to the saw. The reciprocation of the drive links causes the blade head to pivot back and forth. The pivoting of the blade head is what enables the teeth to cut the tissue against which the blade head is pressed. Sometimes, this type of cartridge is referred to as an oscillating tip saw blade cartridge.

An advantage of the sagittal blade cartridge is that the only portion of the cartridge that pivots is the distally located blade head. By way of comparison, a conventional sagittal saw blade pivots from its point of attachment to the saw to which the blade is attached. A cartridge, when actuated, vibrates less in the hands of the surgeon holding the handpiece and/or a robotic arm. Also, it is common practice to use a cutting guide to properly position a sagittal saw blade relative to the tissue the blade is intended to cut. When a conventional blade is actuated, the oscillating movement of the blade imposes significant wear on the surfaces of the cutting guide defining the slot in which the blade is seated. The guide bar of a surgical sagittal blade cartridge only minimally moves in this slot. Thus, by using a cartridge, instead of a conventional blade, less of the material forming the cutting guide is rubbed off the guide.

When either a conventional sagittal blade or a sagittal blade cartridge advances through bone, the blade head is exposed to resistance and/or curved, angled, or shape surfaces. This resistance can be appreciable when the cut has a depth of 5 cm or more. Often the bone located adjacent the underside of the cartridge is more resistive to cutting than the bone located immediately above the cartridge. Similarly, the curve, angle, and/or shape of the bones surface can cause the sagittal blade cartridge to deflect in a certain direction. The cartridge, like most mechanical devices, will when advanced forward, advance along the path of least resistance. Since the bone above the cartridge can be less resistance to cutting than the bone below the cartridge, a cartridge when advanced, can flex upwardly out of the plane of the desired cut. This upwardly flexing or drifting of the blade is known as skiving. There can also be situations when owing to the density of the bone and to the shape of the bone as the point that the device enters, the cartridge, when advanced, flexes below the plane of the cut. This type of flexure or drifting of the blade is known as diving.

Regardless of the direction the blade flexes or drifts, it is undesirable. This is because a sagittal saw blade cartridge is typically used to remove bone so an artificial implant can be fitted in the space previously occupied by the removed bone. An implant is formed with surfaces designed to precisely seat against the complementary surfaces of the bone against which the implant is mounted. If the cut does not leave the bone with surfaces that have the desired shape, the results of the implant fitting procedure may be less than optimal.

In theory, one could increase the rigidity of a surgical sagittal blade cartridge by increasing the thickness of the guide bar. It should be appreciated that the slots of cutting guide through which the cartridge is inserted tend to be relatively narrow. Often the height of this slot is around 1.5 mm or less. This height limit imposes a limit of the thickness of the cartridge guide bar that can be inserted in this slot. Furthermore, if thickness of the guide bar is increased, by extension it is necessary to increase the thickness of the cut that will be formed by the cartridge. Increasing cut thickness can also lead to the cartridge leaving a cut surface that does not have the desired degree of planar smoothness. Increasing guide bar thickness is therefore typically not a viable solution for reducing the incidence of cartridge flexure. In robotic application cut guide thickness is not a limiting factor, but increasing the guide bar thickness thus requires an increase in the blade tip thickness, which also increase the amount of bone to be removed (more work to be done) which can be undesirable.

SUMMARY OF THE INVENTION

This invention is related to a new and useful surgical sagittal blade cartridge. The surgical sagittal blade cartridge includes a guide bar designed to resist deformation when subjected to uneven resistance.

The surgical sagittal blade cartridge of this invention includes a guide bar that is formed with three plates. There is a top plate and a bottom plate opposite the top plate. Between the top and bottom plate there is an inner plate. The inner plate is formed to have a curved head. The curved head functions as the boss around which the cartridge blade head pivots.

This Summary introduces a selection of concepts in a simplified form that are further described below in the Detailed Description below. This Summary is not intended to limit the scope of the claimed subject matter nor identify key features or essential features of the claimed subject matter.

In one aspect, a saw blade cartridge (10) for use with a surgical manipulator (1) is disclosed. The saw blade cartridge also includes a guide bar including a distal portion and a proximal portion, the guide bar may include: a first plate; a second plate; and an inner plate disposed partially between the first and the second plates, the inner plate defining a pivot surface. The cartridge also includes a blade at least partially disposed between the first and the second plates, the blade may include: The cartridge also includes a blade body including a proximal end and a distal end. The cartridge also includes a blade head disposed on the distal end of the blade body, the blade head formed with teeth, where the proximal end of the blade body abuts the pivot surface. The cartridge also includes where the proximal portion defines a proximal end. The cartridge also includes where one of the first and second plates define a first outer edge. The cartridge also includes where the inner plate defines a second outer edge, the second outer edge extends beyond the first outer edge defined by one of the first and second plates and where the second outer edge tapers outwardly from the proximal end to the distal end of the proximal portion such that the second outer edge assists in aligning the saw blade cartridge with the surgical device.

In a second aspect a surgical blade cartridge for use with a surgical manipulator is disclosed. The surgical blade cartridge also includes a first plate. The cartridge also includes a second plate. The cartridge also includes an inner plate, the inner plate defining a pivot surface. The cartridge also includes a blade at least partially disposed between the first and the second plates. The cartridge also includes a blade body including a proximal end and a distal end. The cartridge also includes a blade head disposed on the distal end of the blade body, the blade head formed with teeth, where the proximal end of the blade body abuts the pivot surface. The cartridge also includes the inner plate including a reference feature configured to facilitate determination of at least one of a position and/or orientation of the surgical blade to a navigation system. The cartridge also includes where the first plate, the second plate, and the inner plate are shaped to allow access to the reference feature on the inner plate.

In a third aspect, a method of registering a surgical saw blade with a navigation system is disclosed. The method also includes positioning an instrument including a first tracking device such that distal end of the instrument abuts the reference feature on the inner plate by inserting a distal end of the instrument through the opening in one of the first plate or the second plate. The method also includes determining an actual position and/or orientation of the reference feature based on the step of positioning. The method also includes determining an expected position and/or orientation of the reference feature based on predetermined geometrical data corresponding to the relationship between a mounting feature of a surgical manipulator and the reference feature of the surgical saw blade. The method also includes comparing the expected position and/or orientation of the reference feature with the actual position and orientation of the reference feature.

In a fourth aspect, a surgical sagittal saw blade cartridge is disclosed. The cartridge also includes a blade at least partially disposed between the first plate and the second plate at a distal end of the guide bar, the blade may include: a blade body including a proximal end and a distal end; and a blade head disposed on the distal end of the blade body and extending from the distal end of the guide bar, the blade head formed with teeth, the teeth may include: a plurality of base teeth; and a first pilot tooth. The cartridge also includes at least one drive link moveably disposed within a space defined between the first plate and the second plate of the guide bar, the at least one drive link having opposed proximal and distal ends, the proximal end adapted to be attached to a drive element of a surgical device and the distal end being connected to the proximal end of the blade body so that reciprocation of the at least one drive link results in pivoting of the blade about a pivot surface. The cartridge also includes where the base teeth are configured to move along a first arc when the blade pivots, and the first pilot tooth is configured to move along a second arc. The cartridge also includes where the second arc is distal to the first arc.

In a fifth aspect, a surgical blade of a sagittal saw blade cartridge including a proximal end and a distal end and defining a pivot surface between the proximal end and the distal end is disclosed. The surgical blade also includes a blade body including a proximal end a distal end, the blade body configured to pivot about the pivot surface. The blade also includes a blade head disposed on the distal end of the blade body and extends from the distal end of the sagittal saw blade cartridge, the blade head formed with teeth, the teeth may include: a plurality of base teeth, a first pilot tooth, and a second pilot tooth. The blade also includes a first plane (plane-1) extending between the proximal end the distal end of the blade body, the first plane oriented generally orthogonal to a top surface of the blade body and bisects the blade body; a second plane (plane-2) perpendicular to the first plane, the second plane bisecting the blade body to define a top portion and a bottom portion; where the intersection of the first plane (plane-1) and the second plane (plane-2) defines a central axis of the blade body; and a mirroring plane (plane-3) configured to intersect the central axis and oriented at a mirror angle (θ) measured from the second plane (plane-2). The blade also includes where the blade head is configured such that the second pilot tooth is a mirrored representation of the first pilot tooth mirrored about the mirroring plane (plane-3).

In a sixth aspect, a surgical blade including a proximal end and a distal end and defining a pivot surface between the proximal end and the distal end is disclosed. The surgical blade also includes a blade body including a proximal end a distal end, the blade body configured to pivot about the pivot surface. The blade also includes a blade head disposed on the distal end of the blade body, the blade head formed with teeth, the teeth may include: a plurality of base teeth, and a first pilot tooth. The blade also includes a first plane extending between the proximal end the distal end of the blade body, the first plane oriented generally orthogonal to a top surface of the blade body and bisects the blade body; a second plane perpendicular to the first plane, the second plane bisecting the blade body to define a first portion and a second portion; where the first pilot tooth defines a first apex relative to the pivot surface. The blade also includes where the base teeth define a second apex relative to the pivot surface. The blade also includes the first apex of the first pilot tooth is distal to the second apex of the base teeth.

In a seventh aspect, a method of cutting biological tissue using a surgical blade including a blade head may include a pilot tooth that extends distally beyond a plurality of adjacent base teeth. The method of cutting biological tissue also includes automatically controlling a surgical manipulator to position the surgical blade on a target plane relative to the biological tissue such that the first pilot tooth will contact the biological tissue prior to any of the plurality of base teeth contacting the biological tissue; actuating the surgical blade using a surgical manipulator while the blade is on the target plane.

In an eighth aspect, a surgical sagittal saw blade cartridge for use with a surgical device is disclosed. The surgical sagittal saw blade cartridge also includes a guide bar including a distal portion and a proximal portion, the guide bar may include: a first plate; a second plate; and an inner plate disposed between the first and the second plates, the inner plate defining a pivot surface, a first opening. The cartridge also includes a blade at least partially disposed between the first plate and the second plate at a distal end of the guide bar, the blade having a blade body defining a second pivot surface face to pivot about the pivot surface of the inner plate. The cartridge also includes where one of the first and second plates define a first outer edge of the proximal portion of the guide bar. The cartridge also includes where the inner plate defines a second outer edge of the proximal portion of the guide bar and the guide bar is formed such that the second outer edge extends beyond the first outer edge defined by one of the first and second plates. The cartridge also includes where the combination of the first opening of the inner plate and the second outer edge of the proximal portion of the guide bar defined by the inner plate are configured to axially align the saw blade cartridge relative to the surgical device.

In a ninth aspect, a surgical sagittal saw blade cartridge for use with a surgical device is disclosed. The surgical sagittal saw blade cartridge also includes a guide bar including a distal portion and a proximal portion, the guide bar may include: a first plate; a second plate; and an inner plate disposed between the first and the second plates, the inner plate defining a pivot surface, a first opening, and a second opening. The cartridge also includes a longitudinal axis extending between the distal portion and the proximal portion of the guide bar, the longitudinal axis configured to bisect the guide bar. The cartridge also includes a blade at least partially disposed between the first plate and the second plate at a distal end of the guide bar, the blade having a blade body defining a pivot surface to pivot about the pivot surface of the inner plate. The cartridge also includes where one of the first and second plates define a first outer edge of the proximal portion of the guide bar. The cartridge also includes where the inner plate defines a second outer edge of the proximal portion of the guide bar and the guide bar is formed such that the second outer edge extends beyond the first outer edge defined by one of the first and second plates. The cartridge also includes where each of the first opening, and the second opening are positioned along the longitudinal axis. The cartridge also includes where the combination of the first opening and the second opening of the inner plate are configured to axially align the saw blade cartridge relative to the surgical device.

In a tenth aspect, a surgical blade cartridge for use with a surgical device is disclosed. The cartridge also includes a second plate. The cartridge also includes an inner plate, the inner plate defining a pivot surface, a first opening, and a reference feature, the reference feature configured to facilitate determination of at least one of a position and/or orientation of the surgical blade to a navigation system. The cartridge also includes where at least of the first plate or the second plate defines an opening configured to provide access to the reference feature on the inner plate. The cartridge also includes where the first opening in the inner plate is configured to axially align a center of a radius of the pivot surface relative to the surgical device.

In an eleventh aspect, a method of validating installation of a surgical saw blade relative to a surgical manipulator to which the surgical saw blade is coupled through a mounting feature is disclosed. The method of validating installation also includes tracking, with the navigation system, the first tracking device as the distal tip of the instrument is placed to abut the reference feature. The installation also includes determining, with the navigation system, an actual position and orientation of the reference feature based on the step of tracking. The installation also includes comparing, with the navigation system, the actual position and orientation of the reference feature to an expected position and orientation of the reference feature, the expected position and orientation based on predetermined geometrical data corresponding to a relationship between the mounting feature of the surgical manipulator and the reference feature of the surgical saw blade.

In a twelfth aspect, a method of attaching a surgical saw blade to a surgical manipulator is disclosed. The method also includes positioning the surgical saw blade such that an alignment post of the surgical manipulator is located the first opening and a coupling post of the surgical manipulator is located in the second opening of the inner plate. The method also includes axially aligning the inner plate relative to the surgical manipulator by sliding the inner plate proximally toward the surgical manipulator causing each of the alignment post and the coupling post to move from a proximal position within each of the first opening and the second opening respectively to a distal position within each of the first opening and the second opening.

In a thirteenth aspect, a method assembling a surgical sagittal saw is disclosed. The method also includes attaching a surgical saw blade to a surgical manipulator by positioning the saw surgical saw blade such that an alignment post of the surgical manipulator is located in a first opening of the surgical saw blade and the coupling post of the surgical manipulator is located in a second opening of the surgical saw blade. The method also includes sliding the surgical saw blade proximally toward the surgical manipulator causing each of the alignment post and the coupling post to move from a proximal position within each of the first opening and the second opening respectively to a distal position within each of the first opening and the second opening. The method also includes where the alignment post is sized to simultaneously engage opposing lateral surfaces of the first opening when positioned within the distal position of the first opening to axially align the surgical saw blade relative to the surgical manipulator as the surgical saw blade is slid proximally toward the surgical manipulator.

In a fourteenth aspect, a surgical sagittal saw blade cartridge for use with a surgical device is disclosed. The surgical sagittal saw blade cartridge also includes a guide bar including a distal portion and a proximal portion, the guide bar may include: a first plate; a second plate; and an inner plate disposed between the first and the second plates, the inner plate including an inner tine defining a pivot surface. The cartridge also includes a longitudinal axis extending between the distal portion and the proximal portion of the guide bar, the longitudinal axis configured to bisect the guide bar. The cartridge also includes a blade at least partially disposed between the first plate and the second plate at a distal end of the guide bar, the blade having a blade body defining a pivot face to pivot about the pivot surface of the inner tine. The cartridge also includes where one of the first and second plates define a first outer edge of the proximal portion of the guide bar. The cartridge also includes where the inner plate defines a second outer edge of the proximal portion of the guide bar and the guide bar is formed such that the second outer edge extends laterally beyond the first outer edge defined by one of the first and second plates relative to the longitudinal axis. The cartridge also includes where at least one of the first and the second plates are coupled to the inner plate by a weld formed between the inner tine the first and/or the second plates.

In a fifteenth aspect, a saw blade cartridge for use with a surgical device is disclosed. The saw blade cartridge also includes a guide bar including a distal portion and a proximal portion, the guide bar may include: a first plate, a second plate, the first plate coupled to the second plate and the first plate including a pivot surface. The cartridge also includes a blade at least partially disposed between the first and the second plates, the blade may include: a blade body including a proximal end and a distal end; and a blade head disposed on the distal end of the blade body and configured to extend from the distal portion of the guide bar, the blade head formed with teeth, where the proximal end of the blade body abuts the pivot surface. The cartridge also includes where the proximal portion defines a proximal end. The cartridge also includes where the first plate defines a first outer edge. The cartridge also includes where the second plate defines a second outer edge. The cartridge also includes the guide bar is configured such that the first outer edge extends beyond the second outer edge. The cartridge also includes where the first outer edge tapers outwardly from the proximal end to the distal end of the proximal portion of the guide bar such that the first outer edge assists in aligning the saw blade cartridge with the surgical device.

In a sixteenth aspect, a saw blade cartridge for use with a surgical device is disclosed. The saw blade cartridge also includes a guide bar including a distal portion and a proximal portion, the guide bar may include: a first plate; a second plate; and an inner plate disposed partially between the first and the second plates, the inner plate defining a pivot surface. The cartridge also includes a blade at least partially disposed between the first and the second plates, the blade may include: The cartridge also includes a blade body including a proximal end and a distal end. The cartridge also includes a blade head disposed on the distal end of the blade body and configured to extend from the distal portion of the guide bar, the blade head formed with teeth, where the proximal end of the blade body abuts the pivot surface. The cartridge also includes a longitudinal axis extending between the distal portion and the proximal portion of the guide bar. The cartridge also includes where the proximal portion defines a proximal end. The cartridge also includes where one of the first and second plates define a first outer edge of the proximal portion of the guide bar. The cartridge also includes where the inner plate is configured to define a second outer edge of the proximal portion of the guide bar, the second outer edge extends beyond the first outer edge defined by one of the first and second plates.

In a seventeenth aspect, a saw blade cartridge for use with a surgical device is disclosed. The saw blade cartridge also includes a guide bar including a distal portion and a proximal portion, the guide bar may include: a first plate; a second plate; and an inner plate disposed partially between the first and the second plates, the inner plate configured to define a pivot surface. The cartridge also includes a blade at least partially disposed between the first and the second plates. The cartridge also includes a longitudinal axis extending between the distal portion and the proximal portion of the guide bar. The cartridge also includes where the proximal portion defines a proximal end. The cartridge also includes where one of the first and second plates define a first outer edge. The cartridge also includes where the inner plate defines a second outer edge, the second outer edge extends beyond the first outer edge defined by one of the first and second plates and where the second outer edge tapers outwardly from the proximal end to the distal end of the proximal portion such that the second outer edge assists in aligning the saw blade cartridge with the surgical device. The cartridge also includes where the inner plate further may include a reference feature configured to facilitate determination of at least one of a position and/or orientation of the surgical blade with a navigation system. The cartridge also includes where at least one of the first plate or the second plate is shaped to provide access to the reference feature of the inner plate.

In an eighteenth aspect, a surgical saw system is disclosed. The surgical saw system also includes a surgical device including a mount, the mount defining a mount surface, and the mount may include: a coupling post, and an alignment post. The system also includes a saw blade cartridge removably couplable to the mount of the surgical device, the saw blade cartridge may include: a guide bar including a distal portion and a proximal portion, the guide bar may include: an inner plate defining a pivot surface, a first opening, and a second opening. The system also includes a blade disposed at a distal end of the guide bar, the blade having a blade body defining a pivot face to pivot about the pivot surface of the inner plate. The system also includes where the first opening is sized to receive and slidably engage the alignment post of the mount to axially align the saw blade cartridge relative to the surgical device. The system also includes where the second opening is sized to receive the coupling post of the mount to removably couple the saw blade cartridge to the surgical device.

In a nineteenth aspect, a surgical saw system is disclosed. The surgical saw system also includes a surgical device including a mount, the mount defining a mount surface, and the mount may include: a first wall and a second wall extending above the mounting surface, the first and second wall positioned on opposing sides of a longitudinal axis of the mount; the first and second wall are tapered relative to the longitudinal axis of the mount to facilitate alignment of the saw blade cartridge along the longitudinal axis; at least one tab disposed on each of the first and second walls, each of the at least one tabs positioned above and extending over the mounting surface. The system also includes a saw blade cartridge removably couplable to the mount of the surgical device, the saw blade cartridge may include: a guide bar including a distal portion and a proximal portion, the guide bar may include: a first plate; a second plate; and an inner plate disposed partially between the first and the second plates. The system also includes where one of the first and second plates define a first outer edge. The system also includes where the inner plate is configured to define a second outer edge, the second outer edge extends beyond the first outer edge defined by one of the first and second plates; where each of the first and second walls engage the second outer edge of the inner plate and an under surface of each of the at least one tabs engage a top surface of the inner plate.

In a twentieth aspect, a saw blade cartridge for use with a surgical device. The saw blade cartridge also includes a guide bar including a distal portion and a proximal portion, the guide bar may include: a first plate, a second plate. The cartridge also includes a blade at least partially disposed between the first and the second plates. The cartridge also includes a blade body including a proximal end and a distal end. The cartridge also includes a blade head disposed on the distal end of the blade body and configured to extend from the distal portion of the guide bar, the blade head formed with teeth; where the blade head defines one or more apertures for allowing debris to exit.

In a twenty-first aspect, a method of manufacturing a saw blade cartridge for use with a surgical manipulator is disclosed. The method also includes forming one or more apertures in a blank piece of material to be a blade head of the saw blade cartridge; and machining the blank to form one or more teeth at a location on the blank based on the location and/or position of the one or more apertures.

In a twenty-second aspect, a surgical sagittal saw blade cartridge for use with a surgical device is disclosed. The surgical sagittal saw blade cartridge also includes a guide bar including a distal portion and a proximal portion, the guide bar may include: a first plate, a second plate, and one of the first and second plate defining a pivot member. The cartridge also includes a longitudinal axis extending between the distal portion and the proximal portion of the guide bar, the longitudinal axis configured to bisect the guide bar. The cartridge also includes a blade at least partially disposed between the first plate and the second plate at a distal end of the guide bar, the blade having a blade body defining a pivot surface to pivot about the pivot surface. The cartridge also includes where the guide bar has a first outer edge of the proximal portion of the guide bar and a second outer edge of the proximal portion of the guide bar and the guide bar is formed such that the second outer edge extends beyond the first outer edge. The cartridge also includes the one of the plates that defines the pivot member include a first opening positioned along the longitudinal axis. The cartridge also includes where the combination of the first opening and the second outer edge are configured to axially align the saw blade cartridge relative to the surgical device.

In a twenty-third aspect, a surgical sagittal saw blade cartridge for use with a surgical device is disclosed. The surgical sagittal saw blade cartridge also includes a guide bar including a distal portion and a proximal portion, the guide bar may include: a first plate, a second plate, and one of the first and second plate defining a pivot member. The cartridge also includes a longitudinal axis extending between the distal portion and the proximal portion of the guide bar, the longitudinal axis configured to bisect the guide bar. The cartridge also includes a blade at least partially disposed between the first plate and the second plate at a distal end of the guide bar, the blade having a blade body defining a pivot surface to pivot about the pivot surface. The cartridge also includes where the guide bar has a first outer edge of the proximal portion of the guide bar and a second outer edge of the proximal portion of the guide bar and the guide bar is formed such that the second outer edge extends beyond the first outer edge. The cartridge also includes where the second outer edge is configured to axially align the saw blade cartridge relative to the surgical device.

In a twenty-fourth aspect, a saw blade cartridge for use with a surgical device and registration with a surgical navigation system using a registration tool is disclosed. The saw blade cartridge also includes a guide bar including a distal portion and a proximal portion, the guide bar may include: a first plate; a second plate; and an inner plate disposed partially between the first and the second plates; one of the first and second plates defining an opening to provide access to a surface of the inner plate, the opening shaped to define a first region and a second region; the first region having a first size and being configured to receive insertion of a registration tool; and the second region having a second size that is less than the first size and configured to position the registration tool at a reference feature on the guide bar and/or the inner plate. The cartridge also includes a blade at least partially disposed between the first and the second plates.

In a twenty-fifth aspect, a saw blade cartridge for use with a surgical device is disclosed. The saw blade cartridge also includes a guide bar including a distal portion and a proximal portion, the guide bar may include: a first plate; a second plate; and an inner plate disposed partially between the first and the second plates, the inner plate configured to define a pivot surface. The cartridge also includes a blade at least partially disposed between the first and the second plates. The cartridge also includes a blade body including a proximal end and a distal end. The cartridge also includes a blade head disposed on the distal end of the blade body and configured to extend from the distal portion of the guide bar, the blade head formed with teeth, where the proximal end of the blade body abuts the pivot surface. The cartridge also includes where a surface of the inner plate defines a contact point to removably engage the surgical device. The cartridge also includes where one of the first and second plates is shaped to provide access to the contact point on the inner plate, such that the contact point on the inner plate assists in aligning the saw blade cartridge with the surgical device.

In a twenty-sixth aspect, a surgical sagittal saw blade cartridge for use with a surgical device is disclosed. The surgical sagittal saw blade cartridge also includes a guide bar including a distal portion and a proximal portion, the guide bar may include: a first plate; a second plate; and an inner plate disposed between the first and the second plates, the inner plate defining a pivot surface, a first opening. The cartridge also includes a blade at least partially disposed between the first plate and the second plate at a distal end of the guide bar, the blade having a blade body defining a second pivot surface face to pivot about the pivot surface of the inner plate. The cartridge also includes where one of the first and second plates define a first outer edge of the proximal portion of the guide bar. The cartridge also includes where the inner plate defines a second outer edge of the proximal portion of the guide bar and the guide bar is formed such that the second outer edge extends beyond the first outer edge defined by one of the first and second plates. The cartridge also includes where at least one of the first opening of the inner plate and the second outer edge of the proximal portion of the guide bar defined by the inner plate are configured to orient the saw blade cartridge relative to the surgical device.

In some of the implementations described above, the guide bar may further defines a longitudinal axis extending between the distal portion and the proximal portion of the guide bar; and wherein the second outer edge defines a first taper angle relative to the longitudinal axis between a first point and a second point on the second outer edge; and wherein the second outer edge defines a second taper angle relative to the longitudinal axis between the second point and a third point on the second outer edge, the first point being closer to a proximal end of the cartridge than the third point and the second point being disposed between the first point and the third point.

In some of the implementations described above, the second outer edge defines a third taper angle relative to the longitudinal axis between the third point and a fourth point on the second outer edge.

In some of the implementations described above, the pivot surface may comprise an arcuate surface, and the proximal end of the blade body defining a recess that abuts the pivot surface, such that the blade body is configured to pivot about the pivot surface defined by the inner plate when the blade body is actuated.

In some of the implementations described above, the inner plate may further define a slot configured to axially align the guide bar relative to the surgical device, and the axial slot may be oriented such that the longitudinal axis of the slot is parallel to the longitudinal axis of the guide bar.

In some of the implementations described above, at least one of the plates may define a reference feature configured to facilitate determination of a position and/or orientation of the surgical blade with a navigation system, and the inner plate further comprises a reference feature configured to facilitate determination of a position and/or orientation of the surgical blade with a navigation system.

In some of the implementations described above, the reference feature is selected from the group comprising an optical marking, a divot, or an aperture, the reference feature comprises a plurality of laser markings, and wherein at least one of the plurality of laser markings is positioned on each side of the longitudinal axis.

In some of the implementations described above, at least one of the first plate or the second plate is shaped to provide access to the reference feature of the inner plate, and the reference features is disposed on a surface of the inner plate that is exposed by the second outer edge of the inner plate extending beyond the first outer edge defined by one of the first and second plates.

In some of the implementations described above, the reference feature is configured to identify the saw blade cartridge to the navigation system, including one or more characteristics of the saw blade cartridge, and the characteristic including at least one of the following: a type of the blade, a blade thickness of the blade head, a tooth configuration of the blade head, a length of the guide bar, and/or a width of the guide bar.

In some of the implementations described above, the surgical manipulator and/or the surgical device is one of a hand-held tool, a robotic arm, or a hand-held robot.

In some of the implementations described above, the guide bar is further formed such that the second outer edge extends laterally beyond the first outer edge defined by one of the first and second plates relative to a longitudinal axis extending between the distal portion and the proximal portion of the guide bar.

In some of the implementations described above, the inner tine further defines a first opening, the first opening configured to align the pivot surface relative to the surgical device.

In some of the implementations described above, the guide bar may be configured such at least one of the first opening of the inner plate and the second outer edge of the proximal portion of the guide bar defined by the inner plate are configured to orient the saw blade cartridge relative to the surgical device.

In some of the implementations described above, wherein a surface of the inner plate defines a contact point to removably engage the surgical device; wherein one of the first and second plates is shaped to provide access to the contact point on the inner plate, such that the contact point on the inner plate assists in aligning the saw blade cartridge with the surgical device.

In some of the implementations described above, the guide bar may be configured one of the first and second plates defining an opening to provide access to a surface of the inner plate, the opening shaped to define a first region and a second region; the first region having a first size and being configured to receive insertion of a registration tool; and the second region having a second size that is less than the first size and configured to position the registration tool at a reference feature on the guide bar and/or the inner plate.

In some of the implementations described above, the blade head may define one or more apertures for allowing debris to exit and or to be used as a reference point when manufacturing the blade.

Any of the above aspects can be combined in full or in part. Any features of the above aspects can be combined in full or in part. Any of the above implementations for any aspect can be combined with any other aspect. Any of the above implementations can be combined with any other implementation whether for the same aspect or different aspect.

BRIEF DESCRIPTION OF THE DRAWINGS

The invention is pointed out with particularity in the claims. The above and further features and benefits of this invention are understood from the following Detailed Description taken in conjunction with the accompanying drawings in which:

FIG. 3 is a side view of the saw blade cartridge of FIG. 1.

FIG. 4 is a side view of the distal portion of the saw blade cartridge of FIG. 1 illustrating a side profile of blade head and the pilot teeth.

FIG. 17 is a side view of the saw blade cartridge of FIG. 16.

FIG. 18 is a side view of the distal portion of the saw blade cartridge of FIG. 16 illustrating a side profile of blade head including the single pilot tooth.

DETAILED DESCRIPTION

Figure 1:
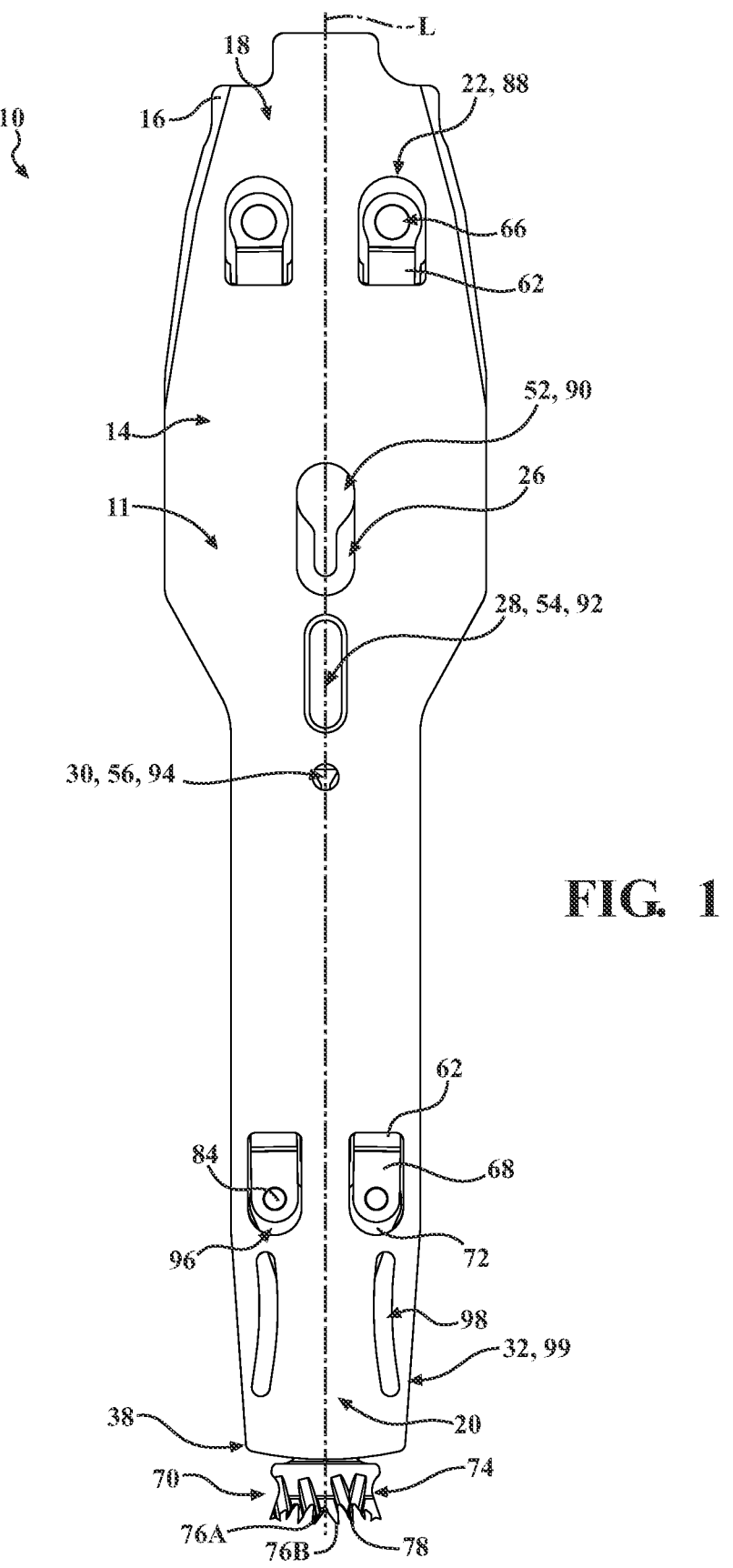
FIG. 1 is a top view of a first configuration of a saw blade cartridge including a distal portion with a single taper.

FIGS. 1 through 11 depict a first configuration of a blade cartridge 10. The sagittal blade cartridge may also be referred to as a sagittal blade cartridge, surgical blade cartridge, or cartridge. The blade cartridge 10 may comprises a guide bar 11. The guide bar 11 may comprises a plurality of plates 12, 14, 16, including a first plate 12, a second plate 14, and a third plate 16. The guide bar 11 may be configured such that the third plate 16 may be disposed between the first plate 12 and the second 14. As such, the first plate 12 may also be referred to as the bottom plate, the second plate 14 may be referred to as a top plate, and the third plate 16 may be referred to as an inner plate, center plate, inner member, center layer, and/or center member. While the guide bar 11 is illustrated as only including three plates layered in a laminate type arrangement, it is contemplated that the guide bar 11 may comprise any number of plates and/or layers.

Collectively, the plates are formed so that the guide bar 11 has a proximal portion 18 that forms the proximal end 18A, 18B, 18C of the plates 12, 14, 16, The proximal portion 18 of the guide bar 11 may be configured to initially taper outwardly as you move distally along the guide bar 11, and then eventually taper inwardly as you move further distally along the guide bar 11. The outward taper of the proximal portion 18 of the guide bar 11 may configured to as a mounting feature to assist in mounting and/or securing the saw blade cartridge 10 to a surgical manipulator 301, such as a surgical robot or medical handpiece. For example, as illustrated in FIG. 1, opposed outer edges of the proximal portion 18B of the third plate 16 may extend beyond the opposed outer edges 36, 86 of the proximal portion 18A, 18C of the first and/or second plates 12, 14. It is a contemplated that the entire length of the opposed outer edges of the of the proximal portion 18B of the third plate 16 may extend beyond on the opposed outer edges 36, 86 defined by the proximal portion 18A, 18C of the first and/or second plates 12, 14. Alternatively, it is also contemplated that the guide bar 11 may be configured such that only a portion of the opposed outer edges of the of the proximal portion 18B of the third plate 16 may extend beyond on the opposed outer edges 36, 86 defined by the proximal portion 18A, 18C of the first and/or second plates 12, 14. For example, referring back to FIG. 1, only a portion of the opposed outer edges of the of the proximal portion 18B of the third plate 16 extend beyond on the opposed outer edges 36, 86 defined by the proximal portion 18A, 18C of the first and/or second plates 12, 14. While not illustrated in the figures, it is further contemplated that one or both of the proximal portion(s) 18A, 18C of the first and/or second plates 12, 14 may be shaped to define a recess or include a cutout defined in the outer edges 36, 86 of the proximal portion 18A, 18C of the first and/or second plates 12, 14 that exposes a portion of the proximal portion 18B of the third plate 16 to be engaged by and/or contact the mount 303 of the surgical manipulator 301. It is also contemplated that only one of the outer edges 36, 86 of the proximal portion 18A, 18C of the first and/or second plates 12, 14 may be shaped to expose a portion of the proximal portion 18B of the third plate 16 to be engaged by and/or contact the mount 303 of the surgical manipulator 301. In this configuration, the other of the outer edges 36, 86 of the proximal portion 18A, 18C of the first and/or second plates 12, 14 may be generally sized and/or shaped to mimic the size and shape of the outer edge of the proximal portion 18B of the third plate 16. The opposed edges of the proximal portion 18B of the third plate 16 extending beyond the opposed outer edges 36, 86 of the proximal portion 18A, 18C of the first and/or second plates 12, 14 may allow for the outer edge of the proximal end 18B of the third plate to be the portion of the guide bar that contacts and/or interacts with the mount 303 of the surgical manipulator 301 for the purpose of mounting and/or aligning of the saw blade cartridge 10 relative to the surgical manipulator 301. This will be described in greater detail below.

Figure 8:
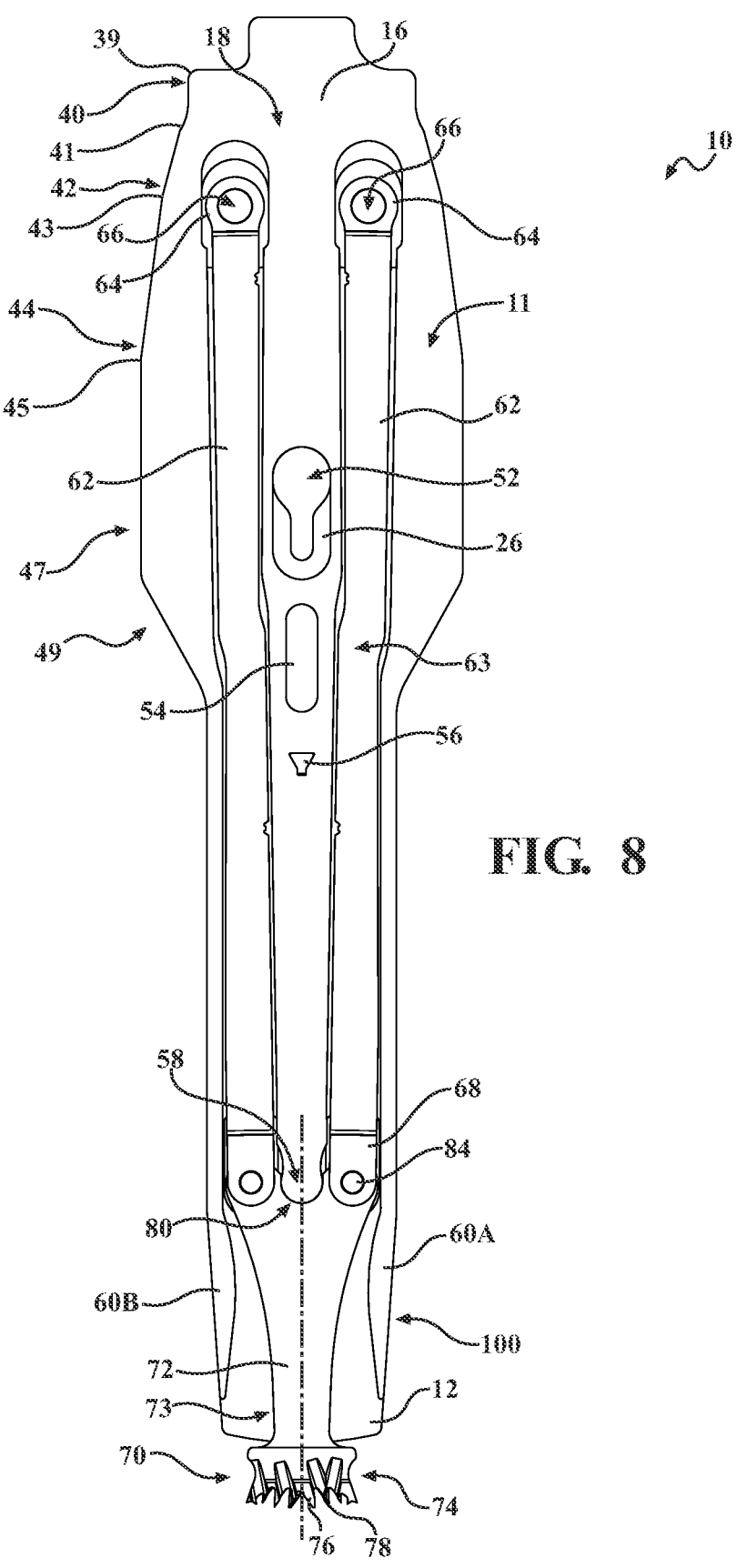
FIG. 8 is a top sectional view illustrating the interior features of the saw blade cartridge of FIG. 1.

Referring to FIG. 8, the opposed outer edges of the proximal portion 18B of the third plate 16 may comprise a number of points 39, 41, 43, 45 spaced along the outer edge of the proximal portion 18. The points 39, 41, 43, 45 along the edge of the proximal portion 18 of the third plate 16 may define a plurality of segments 40, 42, 44 of the edge of the proximal portion 18 of the third plate 16, each of which may comprise varying degrees of taper relative to a longitudinal axis L that extends from the proximal to the distal end of the guide bar 11. For example, the edge of the proximal portion 18B of the third plate 16 may comprise a first segment 40 defined between a first point 39 and a second point 41. The first segment 40 may be generally parallel to the longitudinal axis L of the guide bar 11. Alternatively, the first segment 40 may comprise a first outward directed taper such that the second point 41 is further from the longitudinal axis L of the guide bar 11 than the first point 39.

The outer edge of the proximal portion 18B of the third plate 16 may comprise a second segment 42 defined between the second point 41 and a third point 43. The second segment 42 may comprise a second outward directed taper such that the third point 43 is further from the longitudinal axis L of the guide bar 11 than the second point 41. The outer edge of the proximal portion 18 of the third plate 16 may comprise a third segment 44 defined between the third point 43 and a fourth point 45. The third segment 44 may comprise a third outward directed taper such that the fourth point 45 is further from the longitudinal axis L of the guide bar 11 than the third point 43. The outer edge of the proximal portion 18B of the third plate 16 may comprise a second segment 42 defined between the second point 41 and a third point 43. The second segment 42 may comprise a second outward directed taper such that the third point 43 is further from the longitudinal axis L of the guide bar 11 than the second point 41. The proximal portion 18B of the third plate 16 may be configured such that each of the first, second, and third segments 40, 42, 44 comprise a different taper relative to the longitudinal axis L of the guide bar 11. For example, the first segment 40 may be generally parallel to the longitudinal axis L, the second segment 42 may comprise the second taper, and the third segment 44 may comprise the third taper wherein the second taper extends outward at a larger angle relative to the longitudinal axis L than the third taper. The taper and/or orientation of each of the segment 40, 42, 44 of the opposed outer edges of the proximal portion 18B of the third plate 16 may be correspond to and/or be matched to an angle and/or taper of a surface of a bracket 317 of a mount 303 for securing the saw blade cartridge 10 to the surgical manipulator 301, which will be described in greater detail below.

The proximal portion 18B of the third plate 16 may further comprise a fourth segment 47 of the opposed outer edges that is distal of the third segment 44. The fourth segment 47 of the opposed outer edges of the proximal portion 18B may be configured to be generally parallel to the longitudinal axis L of the guide bar. It is also contemplated that the fourth segment 47 of the opposed edges of the proximal portion 18B may be tapered outwardly as you move distally along the guide bar 11, or it may be tapered inwardly as you move distally along the guide bar 11. The proximal portion 18B of the third plate 16 may further comprise a fifth segment 49 of the opposed edges that is distal of the fourth segment 44. The fifth segment 49 of the opposed edges of the proximal portion 18B may be configured to be tapered inwardly as you move distally along the guide bar 11.

Forward of the proximal portion 18 of the guide bar 11 is a middle portion and a distal portion 20. The plates 12, 14, 16 are formed so that the opposed sides of the guide bar that form the sides of the middle portion are generally parallel. The opposed sides of the distal portion 20 of the guide bar 11 may be tapered in some configurations. As illustrated in the figures, opposed edges 32, 99 of the distal portion 20A, 20B, 20C of the guide bar 11 may be tapered inwardly toward the center of the plates 12, 14, 16. It is also contemplated that the opposed edges of the distal portion 20A, 20B, 20C of the guide bar 11 may be generally parallel to one another. The width across the middle portion and/or the distal portion 20 of the guide bar 11 may be less that the width of the proximal portion 18 at the widest point between the opposed edges of the proximal portion 18 of the guide bar 11.

The proximal portion 18 of each of the plates 12, 14, 16 may further comprise two laterally spaced apart openings 22, 88 (one identified). As illustrated in the figures, the first plate may comprise a pair of openings 22, and the second plate 14 may comprise a pair of openings 88. The third plate 16, depending on the shape of the plate 16 may or may not define an opening. As illustrated in the figures, the third plate 16 is shaped to define a channel 50A, 50B that cooperates with the openings 22, 88 defined in the first and second plates 12, 14. While the plates are illustrated including a pair of openings 22, 88 defined in the first and second plates 12, 14, and a pair of channels 50A, 50B defined by the third plate 16, it is contemplated that the guide bar 11 may be formed with a single opening in each of the plates 22, 88, as well as with more than two opening 22, 88 defined in each of the plates 12, 14, 16. The openings 22, 88 may formed to have a semi-oval shape. Each opening 22, 88 has a curved portion towards the proximal end of the plate 12, 14, 16 and a straight portion towards the distal end of the guide bar 11.

Figure 9:
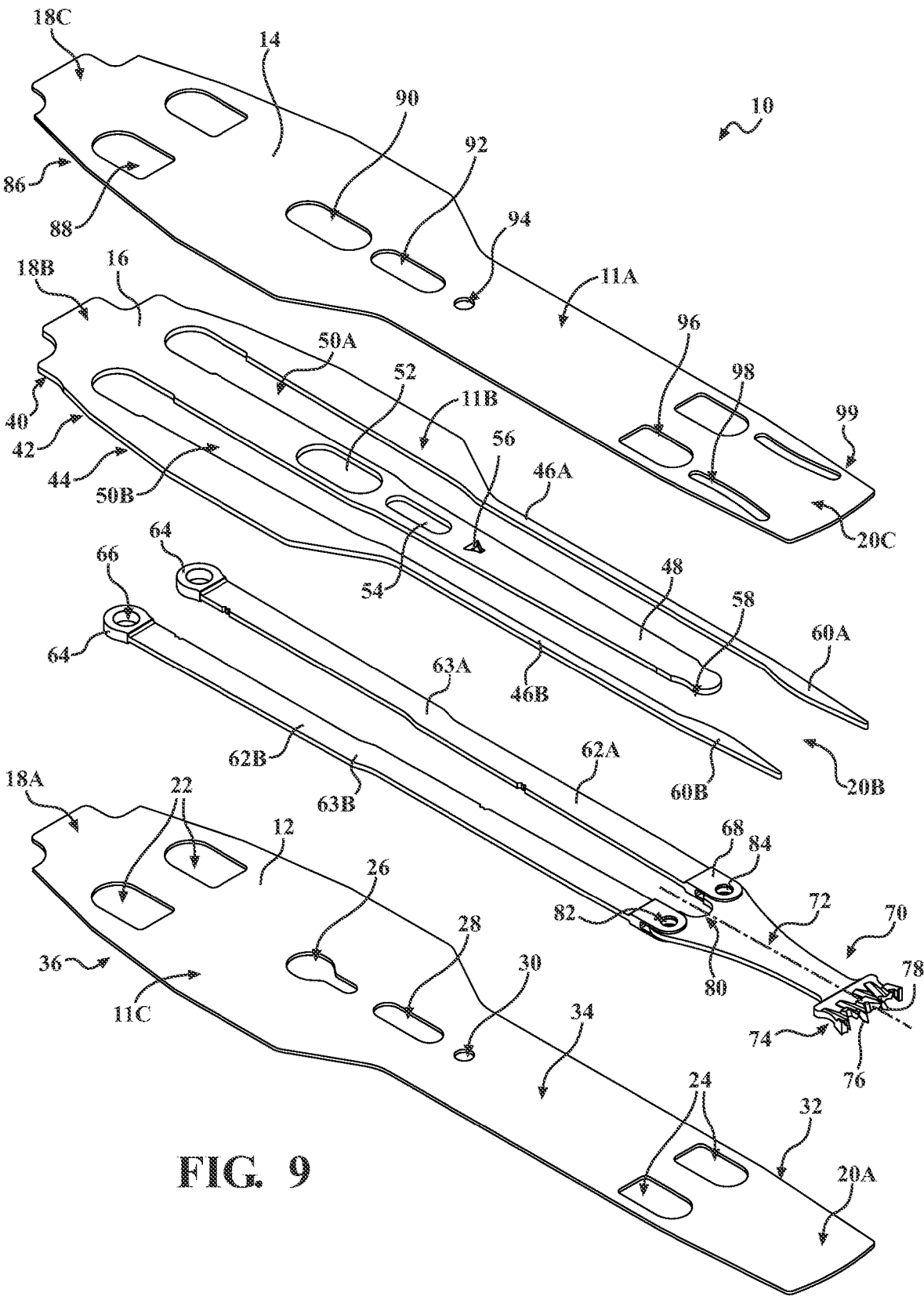
FIG. 9 is an exploded view of the saw blade cartridge of FIG. 1.

Forward of the openings 22, 88, at least one of the plates 12, 14, 16 may be configured to define a keyhole shaped opening 26, 52, 90. As illustrated in the figures, the first plate 12 may define a keyhole shaped opening 26 and the second and third plates 14, 16 define openings 52, 90 that cooperate with the keyhole shaped opening 26 of the first plate 12. While the figures only show the first plate 12 with a keyhole shaped opening 26, it is contemplated that one, two, or all three of the plates 12, 14, 16 may define a keyhole shaped opening 26, 52, 90. For example, it is contemplated that the third plate 16 may define a keyhole shaped opening 52, and the first and second plates 12, 14 may define general openings 26, 90, such as openings in the shape of a square, circle, oval, or the like. Referring to FIG. 9, the keyhole shaped opening 26 is shaped so the widest width portion of the opening 26 can receive a fastening feature of a mount for the saw blade cartridge 10. The openings 26, 52, 90 defined in the respective plates 12, 14, 16 may be centered between the opposed edges of the guide bar 11, such that the openings 26, 52, 90 are positioned on the longitudinal axis L extending between the proximal end 18 and the distal end 20 of the guide bar 11 such that the longitudinal axis L bisects the guide bar 11. The keyhole shaped opening 26 may further be formed so the narrower portion of the opening 26 is located distally forward of the wide width portion of the opening 26 to allow the fastening feature 305 of the mount 303 to slide within the opening 26.

The guide bar 11 may further comprise additional openings 28, 54, 92, formed in the first, second, and/or third plates 12, 14, 16 distal of the keyhole shaped openings 26, 52, 90 configured for alignment and/or mounting of the saw blade cartridge. For example, each of the first, second, and/or third plates 12, 14, 16 may define an opening 28, 54, 92 centered on the longitudinal axis L of the guide bar 11. As illustrated in the figures, the opening 28, 54, 92 may be positioned distal of the keyhole shaped openings 26, 52, 90 on the guide bar 11. However, it is also contemplated that the opening 28, 54, 92 may be positioned proximally of the keyhole shaped openings 26, 52, 90 on the guide bar 11. The opening 28, 54, 92 may be configured for alignment and/or mounting of the saw blade cartridge 10 to a surgical manipulator 301, such as a robot or handpiece. The opening 28, 54, 92 in each of the first, second, and/or third plates 12, 14, 16 may be oriented and/or positioned on the respective plate 12, 14, 16 such that the opening are generally aligned and or concentric with one another when the first, second, and/or third plates 12, 14, 16 are layered upon one another to define a through-hole through the guide bar 11. The opening 28, 54, 92 may be formed as a circle, oval, square, rectangle, or other similar shape. Furthermore, it is also contemplated that each of the respective openings 28, 54, 92 may define a different shape in the respective plates 12, 14, 16 and/or define openings of varying sizes. Only one of the openings 28, 54, 92 may be required for the purpose of alignment of the saw blade cartridge 10 within the surgical manipulator 301. Therefore, only one of the openings 28, 54, 92 may need to be sized and/or shaped to engage an alignment feature 309 of the mount 303 (explained in greater detail below). The remaining openings 28, 54, 92 that do not engage the alignment feature 309 may then be sized and/or shaped such the openings 28, 54, 92 do not contact the alignment feature 309 and/or do not interfere with the opening(s) 28, 54, 92 that is sized and/or shaped to engage the alignment feature 309. For example, as illustrated in FIG. 1, it can be seen that the combination of the openings 28, 54, 92 in the respective plates 12, 14, 16 define a through-hole through the guide bar 11. However, it can also be seen that the opening 54 in the third plate 16 is defined to be slightly smaller than the openings 28, 92 of the first and second plates 12, 14 (only the opening 54 of the third plate 16 can be seen as being smaller than the opening 92 of the second plate 92 in FIG. 1). In this exemplary configuration of the guide bar 11, the opening 54 of the third plate 16 is configured to engage the alignment feature 309 of the mount 303 for the purpose of orienting the saw blade cartridge 10 relative to the surgical manipulator 301, and the opening(s) 28, 92 of the first and second plates 12, 14 are sized and shaped such that they do not contact the alignment feature 309 and/or do not interfere with the opening 54 of the third plates 16 ability to engage the alignment feature 309. As mentioned above, while the opening 54 of the third plate is illustrated as being sized and/or shaped to engage the alignment feature 309 of the mount 303, any of the opening (s) 28, 54, 92 may be sized and/or shaped to engage the alignment feature 309.

The guide bar 11 may further comprise additional openings 30, 94 formed in the first, and/or second plates 12, 14, optionally distal of the keyhole shaped openings 26, 52, 90, and configured for verification and/or registration of the saw blade cartridge 10 with a surgical navigation system. For example, at least one of the first and/or second plates 12, 14 may define an opening 30, 94, shown centered on the longitudinal axis L of the guide bar 11, and oriented and/or positioned to be aligned when the first and second plates 12, 14 are layered upon one another. The first and/or second plates 12 may comprise openings 30, 94 configured to provide access to the reference feature 56 defined in the third plate 16. The reference feature 56 may comprise an aperture defined in the third plate 16 configured as a known contact point for verification and/or registration of the pose of the saw blade cartridge with the surgical navigation system. The reference feature 56 may comprise an aperture in the shape of a triangle, such that the three edges of the aperture defining the triangle act to center a probe or similar device used to touch-off on the reference feature 56. It is contemplated that a reference feature 56 may comprise an aperture in the shape of a circle, square, rectangle, or other similar polygon. Alternatively, the reference feature 56 may comprise a divot defined in the surface of the third plate 16. This may include a divot on a first surface of the third plate that is accessible through the opening 30 in the first plate 12 and/or a divot on a second surface of the third plate that is accessible through the opening 94 defined in the second plate 14. It is further contemplated that the reference feature 56 may comprising a marking. The marking may be realized as an etch, color, engraving, or similar optical marking. The reference feature 56 may be centered on the longitudinal axis L of the guide bar 11.

As described above, the proximal portion 18 of the third plate 16 comprises a number of mounting features and/or contact points intended to facilitate alignment and/or mounting of the saw blade cartridge 10 with the surgical manipulator. Therefore, having the reference feature 56 defined and/or disposed on the third plate 16 may provide the advantage of improved accuracy in verification and/or registration of the saw blade cartridge 10 with the surgical navigation system. Furthermore, it is contemplated that the saw blade cartridge 10 may comprise a plurality of reference features 56. See FIGS. 33 and 34, which will be described in greater detail below.

It should be appreciated that the dimension of the reference feature 56 has a predetermined dimensional relationship with respect to the one or more mounting features. This enables the aforementioned registration and/or verification with the surgical navigation system. The predetermined dimensional relationship may be stored on a memory unit of the surgical navigation system and compared to the measured relationship as determined by a tracked pointer having its distal end positioned at the reference feature. By confirming that the reference feature 56 in the localizer coordinate system is at the expected position, the registration verification step can be performed.

The third plate 16, as seen best in FIGS. 8 and 9, is formed to have a proximal portion 18B of the plate. A pair of laterally spaced apart tines 46A, 46B extend forward from the proximal portion 18B of the third plate 16. The tines 46A, 46B may be referred to as the outer tines. The outer surfaces of tines 46A, 46B are the outer surfaces of the third plate 16 that form sections of the outer side surfaces of the guide bar 11. The outer tines 46A, 46B thus have proximal sections that extending forward from proximal portion 18B and taper first outwardly and then inwardly as you move distally along the third plate 16. The outer tines 46A, 46B are symmetrically located relative to the longitudinal axis L of the guide bar 11. Outer tines 46A, 46B are further shaped to be mirror images each other, mirrored about the longitudinal axis L. Furthermore, the outer tines 46A, 46B may be configured to couple the couple the first, second and third plates 12, 14, 16 together to form the guide bar 11. For example, the first and second plates 12, 14 may be welded or similarly coupled to the outer tines 46A, 46B of the third plate 16 to form the guide bar 11. Alternatively, it is also contemplated that the first and second plates 12, 14 may be welded or similarly coupled to the inner tine 48 of the third plate 16 to form the guide bar 11. By welding or similarly coupling the first and second plates 12, 14 to the inner tine 48 of the third plate 16, it may avoid any interference, unintended warping or similar disturbance to the edges of the proximal portion 18 of the third plate 16, which may utilized in aligning and/or orienting the guide bar 11 relative to the surgical manipulator.

Adjacent the distal end of each tine 46A, 46B, is shaped to have a lobe 60A, 60B, that extends inwardly towards the longitudinal axis L of the guide bar 11. Moving proximally to distally along the tine 46A, 46B, the associated lobe 60A, 60B first curves inwardly toward the longitudinal axis L of the guide bar 11 and then curves outwardly.

The third plate 16 may further comprise a third tine 48, the inner tine, that is disposed between the outer tines 46A, 46B and is centered on the longitudinal axis L of the guide bar 11. As described above, the inner tine 48 may be formed to define an opening 52 which may be a keyhole shaped opening 52. The inner tine 48 may shaped so that opening 52 is identical in shape and positioned to be in registration with opening 26 and 90 of first and second plates 12, 14, respectively. The inner tine 48 is of constant width except for the distal end of the tine. At the most distal end, the inner tine 48 may comprise a head 58 with a distally directed face that is curved and configured to define a pivot surface. While not illustrated in the figures, it is also contemplated that the head 58 may be defined a recessed surface configured to receive a rocker or curved surface that may pivot within the recessed surfaced defined by the head 58. The head 58 may include a center, the center defining a radius of the distally directed face that is curved to define the pivot surface. The center, similar to the opening 54 and the reference feature 56 of the third plate 16, may be positioned on the longitudinal axis L of the guide bar 11. This creates alignment of the head 58, opening 54, and the reference feature 56 along the longitudinal axis L of the guide bar 11, and may aid in alignment and/or registration of the blade cartridge 10 with the navigation system and or positioning of the blade cartridge 10 relative to the surgical manipulator. It can be advantageous to have the features for mounting and/or aligning the cartridge relative to the surgical manipulator, such as the opening 54 and/or keyhole shaped opening 52 on the same axis as the head 58 about which the blade is manipulated and the reference feature 56. This can lead to better alignment of the blade cartridge 10 with the surgical manipulator, which can also then lead to improved tolerances with regard to the registration of the blade cartridge 10 to the navigations system. Furthermore, in the provided exemplary configuration of the blade cartridge 10, the opposed edges of the proximal portion 18B of the third plate 16 may be configured as a mounting feature for the saw blade cartridge 10. In the exemplary configuration, all of the various mounting features, alignment features, and navigation registration features may by located and/or disposed on the third plate 16. This can result in improved tolerances and/or repeatability of positioning the blade cartridge 10 relative to the surgical manipulator, resulting in more accurate position identification and by extension, navigation of the blade cartridge 10 during a medical procedure.

While the figures illustrate an inner tine disposed between the outer tines 46A, 46B, it is contemplated that the third plate 16 may be formed without the inner tine 48, and only include the two outer tines 46A, 46B spaced apart from one another. In such a configuration, a pivot pin may be coupled adjacent the blade head. In other words, while the third plate is shown has having three tines formed as a single component, it is contemplated that the three tines may be formed separately and secured between the first and second plates.

The outer tines 46A, 46B are spaced apart from the inner tine 48, such that the third plate 16 defines a pair of elongated, closed end slot 50A, 50B between each of the outer tines 46A, 46B and the inner tine 48. The proximal end of the slot 50A, 50B is the closed end of the slot. When cartridge 10 is assembled, each slot 50A, 50B is disposed over a separate one of the openings 22, 88 in the first and second plates 12, 14, respectively. The third plate 16 is further formed so that the proximal end portion of each slot 50A, 50B has a shape substantially equal to the shape of openings 22, 88 in the first and second plates 12, 14. Thus, the lateral width of the proximal end portion of each slot 50A, 50B is greater than the width of the slot 50A, 50B distally forward of the proximal portion 18.

While the third plate 16 is generally depicted in the figures as being formed as a single solitary or unitary plate, it is contemplated that the third plate 16 may be configured as a plurality of separate pieces arranged to form the features and/or portions of the third plate 16 that are described above. For example, the proximal portion 18 of the third plate 16 may be formed as a unitary piece with the outer tines 46A, 46B, and the inner tine 48 may be a separate piece. Alternatively, the inner tine 48 may be omitted. In yet another exemplary configuration, the proximal portion 18 of the third plate 16, the outer tines 46A, 46B, and the inner tine 48 may all be formed as separate pieces.

Referring to FIG. 9, it is observed that first plate 12 is shaped to have an outer perimeter substantially identical to that of second plate 14. However, it is also contemplated that the one of the first plate 12 or the second plate 14 may be longer/shorter and/or narrower/wider than the other plate. For example, the second plate 14 may be constructed such that the outer perimeter is narrower, i.e. the perimeter edge is closer to the longitudinal axis L, than that of the first plate 12. Forward of the proximal portion 18 of the first and second plates 12, 14 is a distal portion 20. The distal portion of the first and second plates 12, 14 is shaped to have two openings 24, 96. The openings 24, 96 are identical in shape and positioned such that the openings 24 of the first plate 12 are in registration with the openings 96 of the second plate 96.

The saw blade cartridge 10 may further comprise a saw blade 70 disposed between the first and second plates 12, 14 at the distal end of the saw guide bar 11. The saw blade 70 is formed to have a blade body 72 and a blade head 74. The saw blade 70 is formed so that blade body has a thickness that is no greater than the thickness of third plate 16. The blade body 72 of the saw blade 70 seen in FIGS. 8 and 9 is generally rectangular in shape. However, it is also contemplated that the perimeter edges 73 of the blade body 72 may be tapered and/or curved. The taper and/or curve may be matched to the taper or curve of the lobes 60A, 60B of the outer tines 46A, 46B of the inner plate 16. The shape of the blade body may be configured to allow the blade body 72 to pivot about the head 58 of the inner tine 48, oscillating between the lobes 60A, 60B of the outer tines 46A, 46B.

When saw blade 70 is in the centered position within the guide bar 11 the major axis of the blade body 72 is collinear with the longitudinal axis L of the guide bar 11. The blade body 72 may be shaped to have two feet 84, one foot identified. The feet 84 have the same thickness of as the blade body 72. Each foot 84 extends to the open end of the adjacent slot 50A, 50B internal to the inner tine 48. Between the feet 84, the blade body 72 is formed to have a curved, proximally directed face 80. The blade body 72 is shaped so that face 80 can seat against and pivot around the head 58 integral with the inner tine 48. While the figures illustrate the third plate with an inner tine 48 defining a head 58 for the saw blade to pivot about, it is further contemplated that the guide bar may be configured with a pin disposed between the first and second plates 12, 14, and the saw blade 70 being configured to pivot about the pin. The blade feet 84 and blade body 72 are sometimes referred to as the base of the saw blade 70.

The distal end of the blade body 72 extends distally of the guide bar 11, such that the blade head 74 extends forward of the distal end of guide bar 11. The blade head 74 is formed with a plurality of teeth 76, 78. The saw blade 70 is further formed so that blade head 74 has a thickness greater than that of the blade body 72. More particularly, the blade head 74 is formed to have a thickness equal to or greater than the thickness of the guide bar 11 so that the kerf formed by the cutting action of saw blade 70 is sufficient to receive the guide bar 11.

Figure 2:
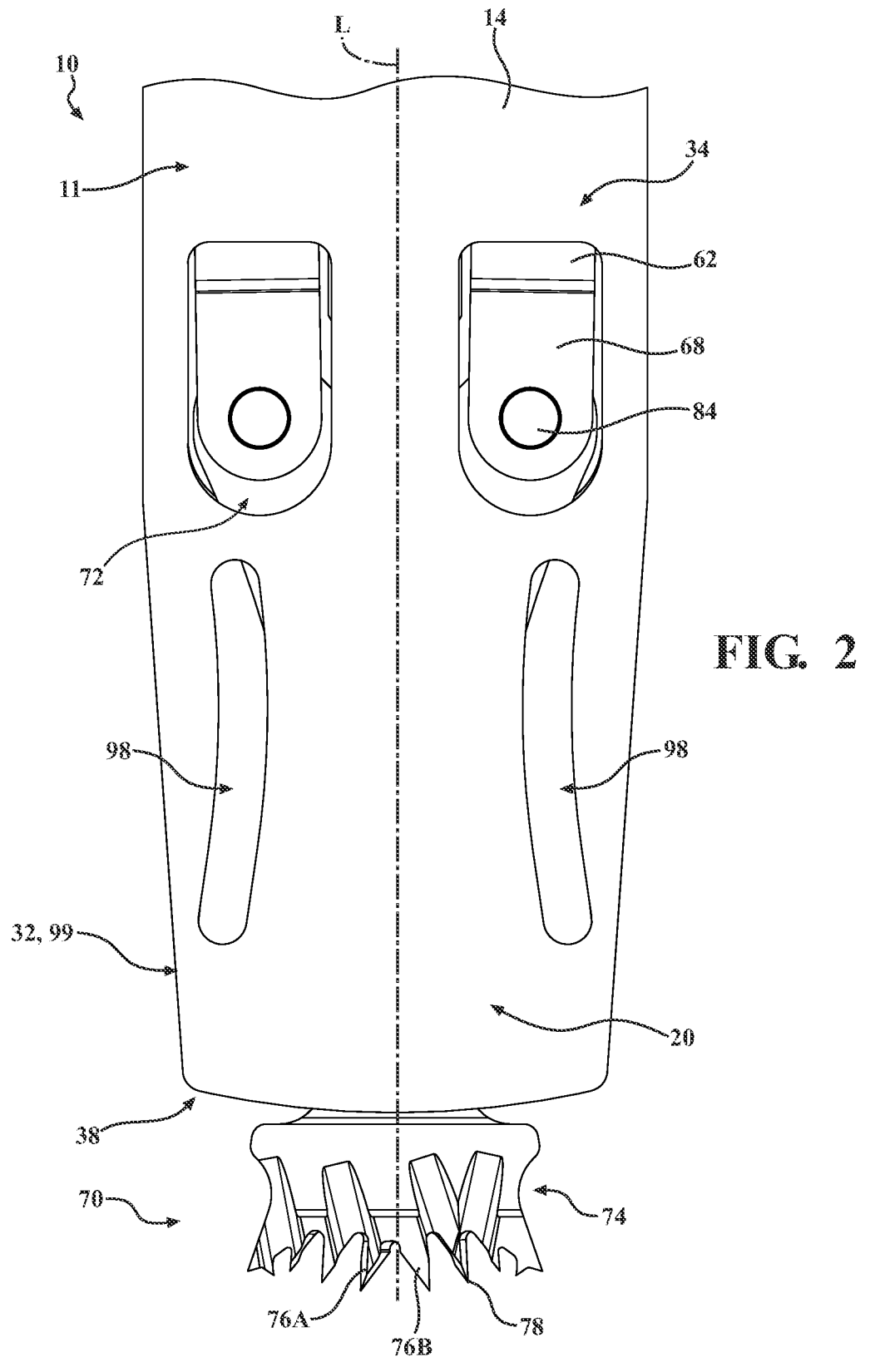
FIG. 2 is a top view of the distal portion of the saw blade cartridge of FIG. 1 including a first configuration of a saw blade, the first configuration saw blade including a blade head with a plurality of base teeth and two pilot teeth.
Figure 5:
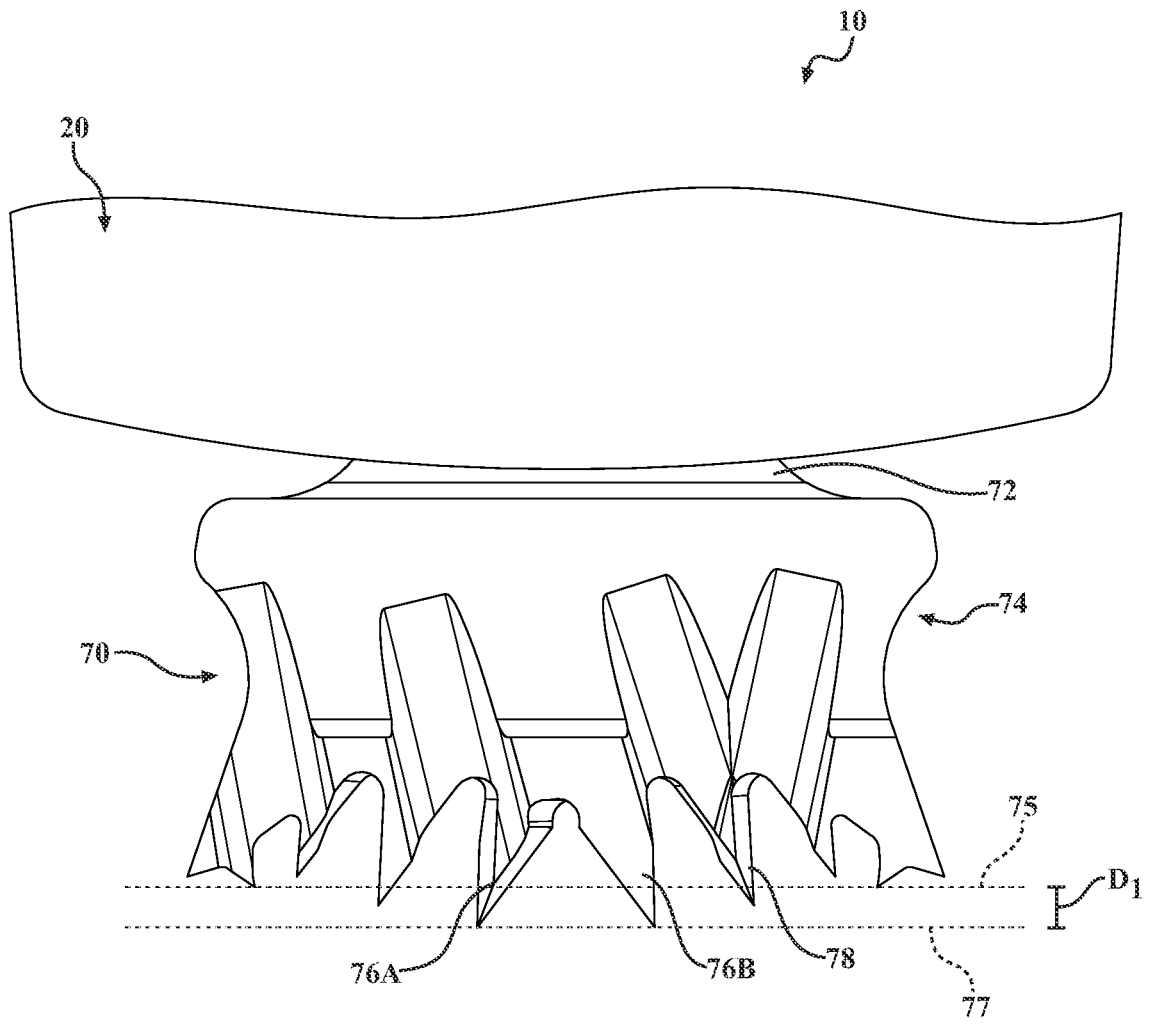
FIG. 5 is a top view of the blade head of the first configuration of the saw blade of the saw blade cartridge of FIG. 1, the blade head including two pilot teeth proximate the central axis off the saw blade and configured to extend distally of the base teeth of the blade head.

Referring to FIGS. 2 through 5, the blade head 74 may comprise two type of teeth, base teeth 78 and one or more pilot teeth 76. For example, as illustrated in FIG. 2, the blade head 74 may comprise two pilot teeth 76A, 76B. However, it is contemplated that the blade head 74 may comprise a single pilot tooth, or more than two pilot teeth. The pilot teeth 76A, 76B may be disposed proximate the center of the distal surface of the blade head 74. Furthermore, the pilot teeth 76A, 76B may be configured to extend a first distance D1 distally beyond the adjacent base teeth 78 of the blade head 74, as best seen in FIG. 5. In operation, with the pilot teeth 76A, 76B extending distally beyond the adjacent base teeth 78, the pilot teeth 76A, 76B are configured to oscillate along a first arc distance 77 as the adjacent base teeth 78 oscillate about a second arc distance 75, such that the first arc distance 77 is distal to the second arc distance 75.

Figure 6:
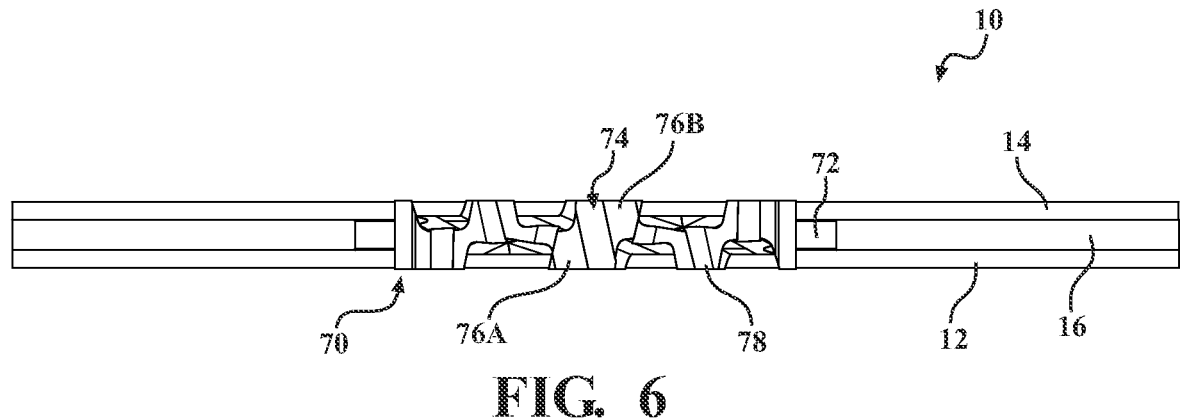
FIG. 6 is a front view of the blade head of the saw blade of the saw blade cartridge of FIG. 1.
Figure 7:
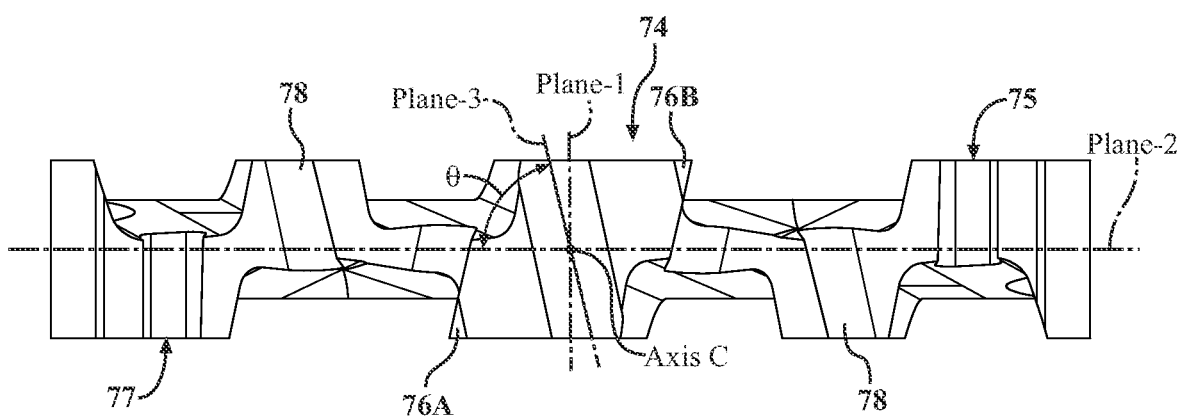
FIG. 7 is a front view of the blade head of the first configuration of the saw blade of the saw blade cartridge of FIG. 1 illustrating a front profile of the base teeth and pilot teeth.

Referring to FIGS. 5 through 7, the saw blade 70 may comprise a central axis C that extends from the proximal to the distal end of the saw blade 70. A first plane, Plane-1, may be oriented to intersect the central axis C of the saw blade 70 and bisect the saw blade into left and right halves. A second plane, Plane-2, may be oriented to intersect the central axis C of the saw blade 70 and bisect the saw blade into top and bottom halves. Plane-1 and Plane-2 may be oriented to be perpendicular to one another. The pilot teeth 76A, 76B may be configured to extend distally from the blade head 74 and positioned such that they are on opposing sided of Plane-1.

A third plane, Plane-3, may be configured to intersect the central axis C of the saw blade 70. Plane-3 may be oriented at a mirror angle, θ, relative to either of Plane-1 and/or Plane-2. For example, Plane-3 is oriented at a mirror angle, θ, that is defined relative to Plane-2. The mirror angle θ, as measured relative to plane-2, may be any angle ranging from 20 to 80 degrees. For example, plane-3 may be oriented at a mirror angle θ of 75 degrees relative to plane-2. The Plane-3 may also be referred to as the mirror-plane, as the pilot teeth 76A, 76B may be mirrored across plane-3. For example. the second pilot tooth 76B may be oriented such that it is a mirrored representation of the first pilot tooth 76A mirrored about plane-3, the mirroring plane.

It is also contemplated that each of that each of the pilot teeth 76A, 76B may be oriented in a cross-cut pattern, wherein adjacent teeth are oriented at opposing angles relative to one another. For example, referring back to FIGS. 3 and 4, a side profile of the blade head 74 is illustrated illustrating that the pilot teeth 76A, 76B are oriented in a cross-cut pattern. The first pilot tooth 76A is oriented in a generally downward direction relative to Plane-2, and the second pilot tooth 76B that is positioned adjacent the first pilot tooth 76A is oriented in a generally upward direction relative to Plane-2, with the pilot teeth 76A, 76B defining a v-shaped side at the distal end of the blade head 74.

A drive link 62A, 62B is disposed in each of the slots 50A, 50B internal to the guide bar 11. Each drive link 62A, 62B is in the form of an elongated flat strip of metal. The drive links 62A, 62B are formed so that, at the proximal end of each link, there is a foot 64. Each foot 64 is formed to have a center located through hole 66, one opening identified. Through holes 66 are dimensioned so that the associated drive link feet 64 can be fitted over the saw head drive pins. Each drive link 62A, 62B is shaped so that foot 64 has a thickness that is greater than the thickness of the metal strip forming the main body of the link 62A, 62B. The thickness of the feet 64 is typically no greater than the thickness of the guide bar 11. When the cartridge 10 is assembled, the feet 64 generally seat in the proximal end portion of the associated slot 50A, 50B. The portions of the feet 64 that project outwardly from the main body of each link 62A, 62B seat in the openings 22, 88 of the first and/or second plates 12, 14.

The drive links 62A, 62B may further comprise two fingers 68 extend distally forward from the distal end of the main body of each drive link 62A, 62B, one finger identified. Fingers 68 overlap and are spaced apart from each other. More particularly, fingers 68 are spaced apart from each a sufficient distance so that a blade foot 84 can seat between each pair of fingers. Each finger 68 is formed with a hole 82. The holes 82 of each pair of fingers 68 are in registration with each other.

As part of the process of assembly a cartridge 10, the saw blade 70 is positioned so that each blade foot 84 is disposed between a pair of drive link fingers 68. A pivot pin may then extend through the finger holes 84 and an opening blade foot to pivotally holds the foot 84 to the associated drive link 62A, 62B.

During the assembly of the cartridge 10, the third plate 16 is initially welded or otherwise secured to the first plate 12 and/or to the second plate 14. After this operation is completed, the drive links-and-blade assembly is positioned so that the drive links 62A, 62B are seated in slots 50A, 50B and the curved proximally directed face 80 of blade 70 is seated against the curved distally directed face of head 58 integral with the third plate 16. The second plate 14 and/or first plate 12 is then welded or otherwise secured to the exposed face of the third plate 16. At the completion of the process of assembling the cartridge 10, the drive link feet 64 seat in openings 22, 88 of the first and second plates 12, 14. The drive link fingers 68 seat in openings 24, 96 formed, respectively in the first and second plates 12, 14. Blade head 74 is located immediately forward of the distal end of the guide bar 11.

Figure 10:
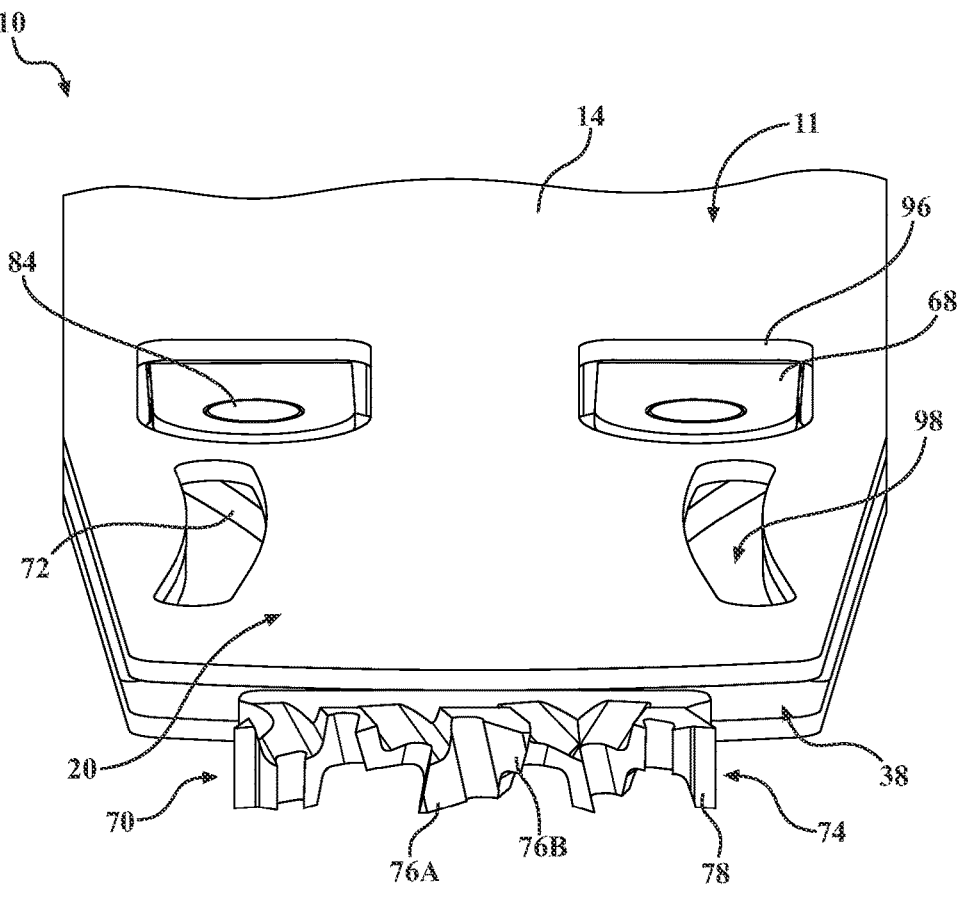
FIG. 10 is a front perspective view of the distal portion of the saw blade cartridge of FIG. 1.
Figure 11:
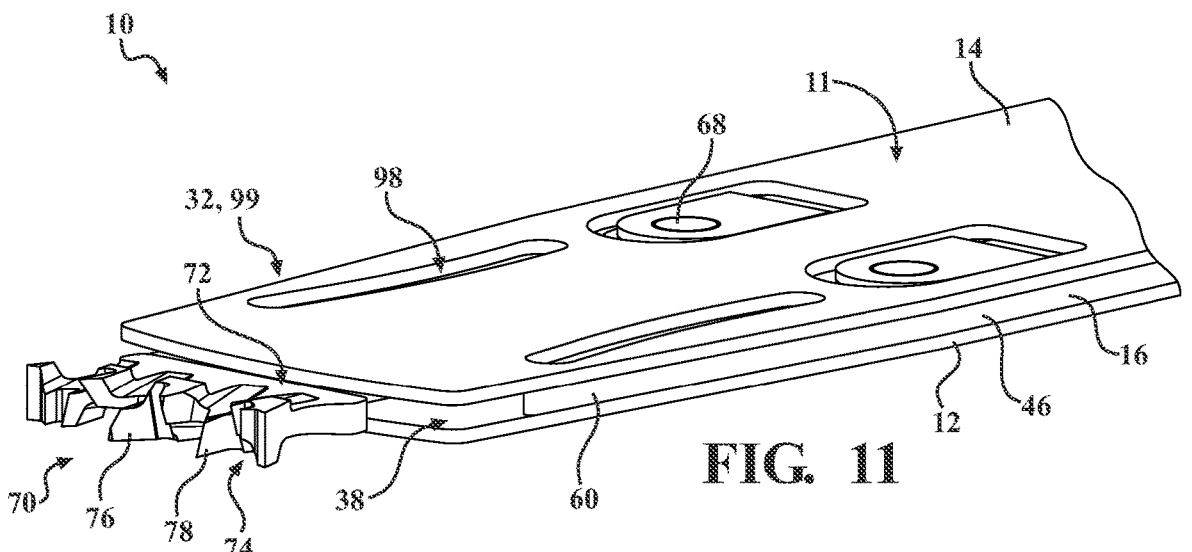
FIG. 11 is a side perspective view of the distal portion of the saw blade cartridge of FIG. 1.
Figure 12:
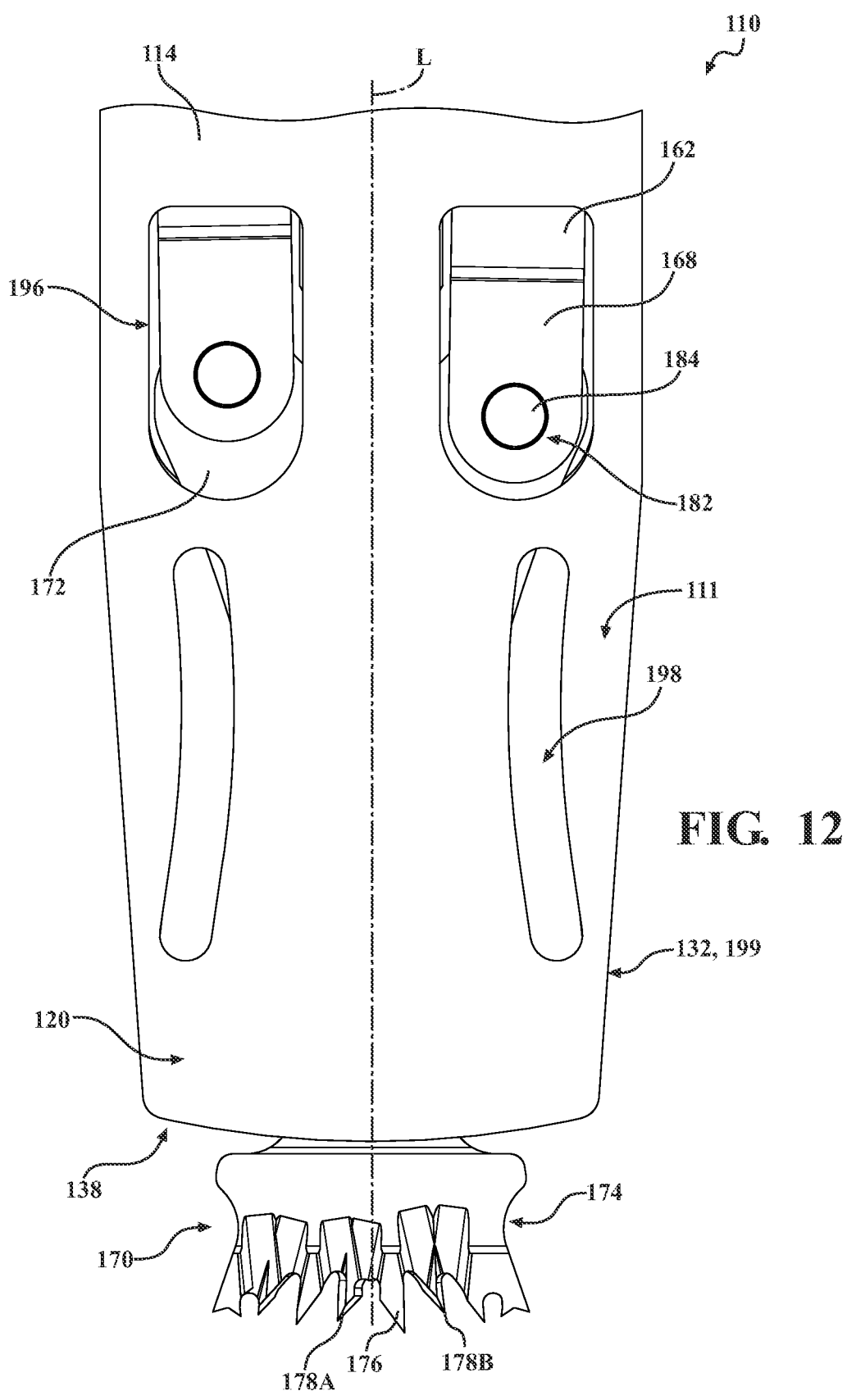
FIG. 12 is a top view of a distal portion of the saw blade cartridge of FIG. 1 including a second configuration of a saw blade, the second configuration of the saw blade including a blade head with a plurality of base teeth and a single pilot tooth.

Referring to FIGS. 10 and 11, the distal portion of the guide bar 11 may comprises a pair of generally oval shaped opening 98 in the second plate 14. While two openings 98 are illustrated in the figures, it is contemplated that guide bar may be constructed with only a single opening, or with more than two openings. Furthermore, while the openings are illustrated in the figures as being defined in the second plate 14, it is contemplated that the similar openings may also be defined in the first plate 12. The openings 98 may comprise a curve and/or bend that extends longitudinally along the length of the distal portion 20 of the second plate 14. The opening may be configured to assist with the removal of debris that may become trapped between the first and second plates 12, 14 when the saw blade cartridge 10 is utilized to cut biological tissue.

The distal portion 20 of the guide bar 11 may also be formed to define a cut-out or slot 38 between the first and second plates 12, 14. As illustrated in FIGS. 10 and 11, the outer tine 46 of the inner plate 16 is formed so that the distal most point of the lobe 60 of the outer tine 46 is positioned proximal of the distal most edge of the first and second plates 12, 14. This arrangement defines a slot 38 along the side edge of the guide bar 11 that may assist the removal of debris that may become trapped between the first and second plates 12, 14 when the saw blade cartridge 10 is utilized to cut biological tissue. The slot 38 along the side edge of the guide bar 11 that may also assist to increase the range of motion of the saw blade 70 as it is pivoted. By shortening the length of the outer tines 46, increased clearance may be provided allowing the saw blade to pivot further, and thus increasing the distance the blade head 74 may oscillate.

While not illustrated in the figures, it is further contemplated that the saw blade cartridge 10 may include ribs on the outer surface of the guide bar. The ribs may be aligned with the longitudinal axis L of the guide bar 11. The ribs may be formed separate from the first and/or second plates 12, 14, and welded or otherwise permanently secured to the rest of cartridge 10. The ribs may reduce the flexing of the guide bar 11. An exemplary configuration of a saw blade cartridge is disclosed in PCT Pub. No. WO 2013/016472A1/US Pat. Pub. No. 2014/0163558, which is explicitly incorporated herein by reference.

Referring to FIGS. 12 to 15, a second configuration of the saw blade cartridge 110 is illustrated. It should be understood that components and/or features of the second configuration of the saw blade cartridge 110 including the same base reference number increased by one hundred, i.e. 10 and 110, may operate in a similar or the exact same manner as described above.

Similar to as described above, the second configuration of the saw blade cartridge 110 may comprises a guide bar 111 including a plurality of plates (112, 114, 116), including a first plate 112, a second plate 114, and a third plate 116. The guide bar 111 may be configured such that the third plate 116 may be disposed between the first plate 112 and the second 114. The first, second, and third plates, 112, 114, 116 are constructed in the same or similar fashion as those of the saw blade cartridge 10 described above. However, the configuration of the saw blade cartridge 110 illustrated in FIGS. 12 to 15 is constructed with an alternative configuration of a saw blade 170.

Figure 13:
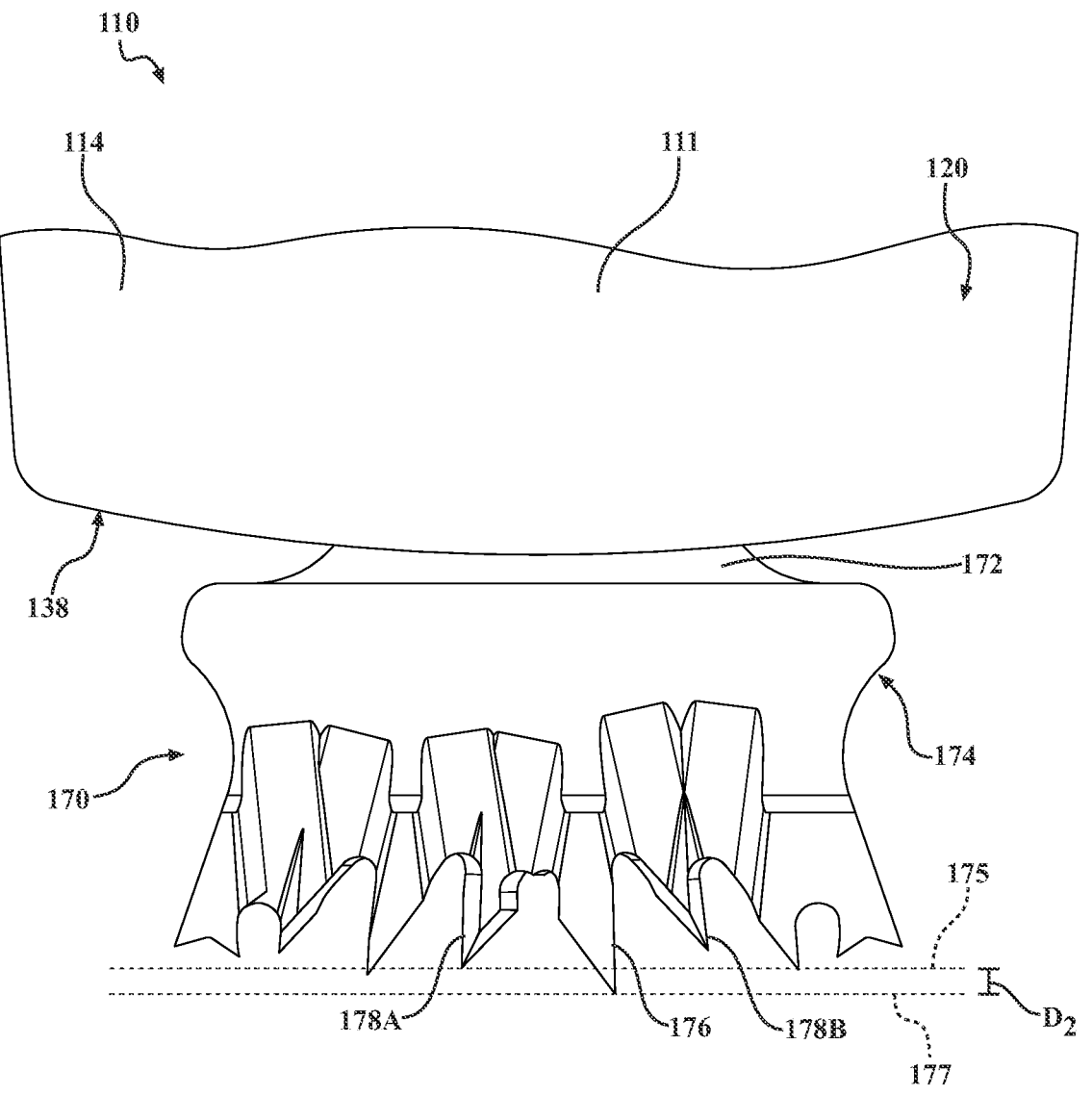
FIG. 13 is a top view of the blade head of the second configuration of the saw blade of FIG. 12, the blade head including the single pilot tooth proximate the central axis off the saw blade and configured to extend distally of the base teeth of the blade head.

Referring to FIG. 13, the saw blade 170 may comprise a blade body 172 that extends distally of the guide bar 111, such that a blade head 174 coupled to the distal end of the blade body 172 extends forward of the distal end of guide bar 111. The blade head 174 is formed with a plurality of teeth 176, 178. The saw blade 170 is further formed so that blade head 174 has a thickness greater than that of the blade body 172. More particularly, the blade head 174 is formed to have a thickness equal to or greater than the thickness of the guide bar 111 so that the kerf formed by the cutting action of saw blade 170 is sufficient to receive the guide bar 111.

The blade head 174 may comprise two type of teeth, base teeth 178 and one or more pilot teeth 176. For example, as illustrated in FIG. 13, the blade head 74 may comprises a single pilot tooth 176. As described above, the blade head 174 may also comprise two or more pilot teeth. The pilot tooth 176 may be disposed proximate the center of the distal surface of the blade head 174. Furthermore, the pilot tooth 176 may be configured to extend a second distance D2 distally beyond the adjacent base teeth 178A, 178B of the blade head 174, as best seen in FIG. 13. In operation, with the pilot tooth 176 extends distally beyond the adjacent base teeth 178A, 178B, the pilot tooth 176 is configured to oscillate along a first arc 177 as the adjacent base teeth 78 oscillate about a second arc distance 175, such that the first arc distance 177 is distal to the second arc distance 175.

Figure 14:
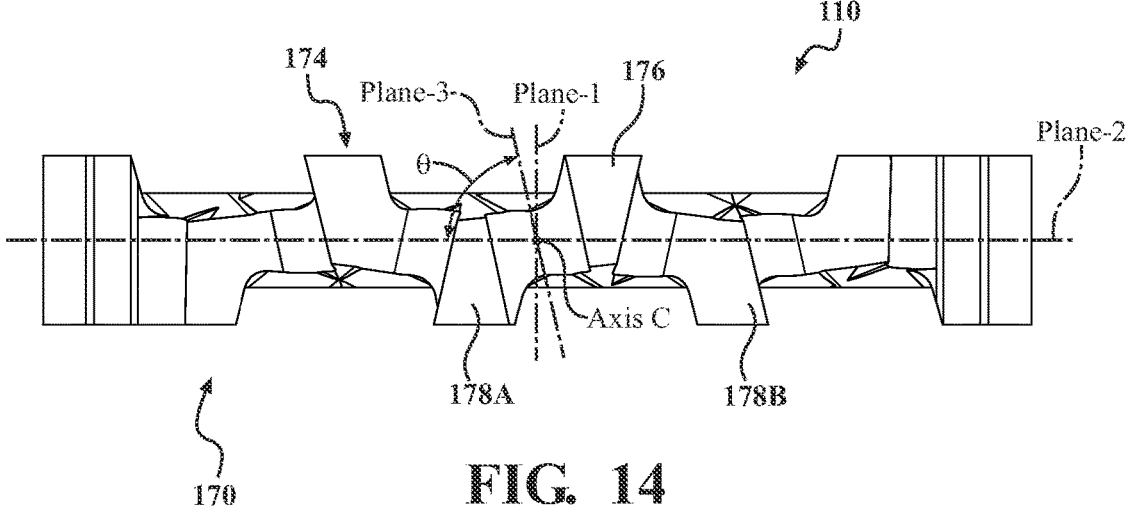
FIG. 14 is a front view of the blade head of the second configuration of the saw blade of FIG. 12 illustrating a front profile of the base teeth and pilot tooth.
Figure 15:
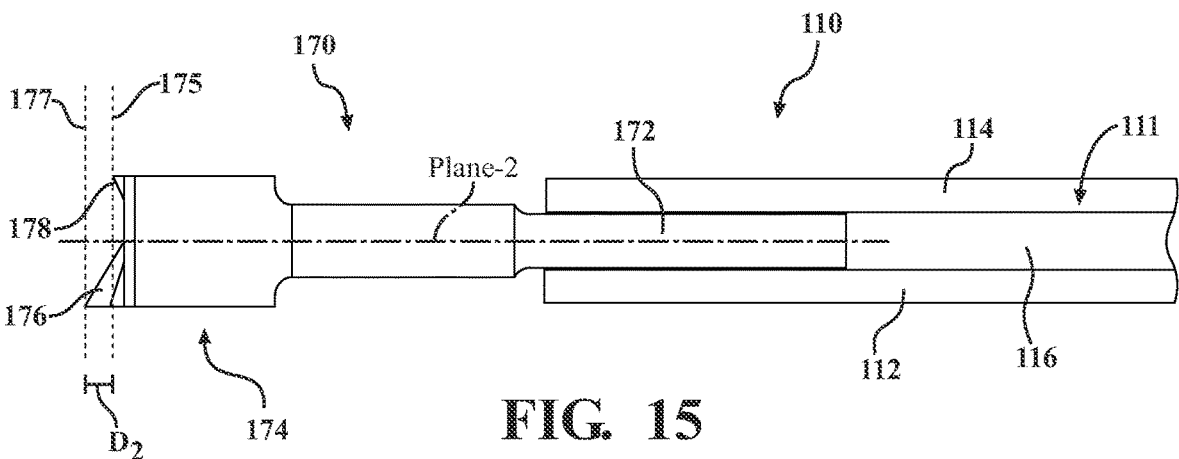
FIG. 15 is a side view of the distal portion of the second configuration of the saw blade of FIG. 12 illustrating a side profile of the blade head and the pilot tooth.

Referring to FIGS. 14 and 15, the saw blade 170 may comprise a central axis C that extends from the proximal to the distal end of the saw blade 170. A first plane, Plane-1, may be oriented to intersect the central axis C of the saw blade 170 and bisect the saw blade into left and right halves. A second plane, Plane-2, may be oriented to intersect the central axis C of the saw blade 170 and bisect the saw blade into top and bottom halves. Plane-1 and Plane-2 may be oriented to be perpendicular to one another. The pilot tooth 76 may be configured to extend distally from the blade head 174 and on one side of Plane-1, with an adjacent base tooth 178B disposed on the opposing side of Plane-1.

A third plane, Plane-3, may be configured to intersect the central axis C of the saw blade 170. Plane-3 may be oriented at a mirror angle, $\theta$, relative to either of Plane-1 and/or Plane-2. For example, Plane-3 is oriented at a mirror angle, $\theta$, that is defined relative to Plane-2. The mirror angle $\theta$, as measured relative to plane-2, may be any angle ranging from 20 to 80 degrees. For example, plane-3 may be oriented at a mirror angle $\theta$ of 75 degrees relative to plane-2. The plane-3 may also be referred to as the mirror-plane, as the pilot tooth 176 and the adjacent, shorter base tooth 178B each have surfaces that define a cutting edge that is mirrored across plane-3. For example. the adjacent, shorter base tooth 178B may be oriented such that it has a face that is a mirrored representation of the pilot tooth 176 mirrored about plane-3, the mirroring plane.

It is also contemplated that each of that each of the pilot tooth 176 and adjacent base teeth 178A, 178B may be oriented in a cross-cut pattern, wherein adjacent teeth are oriented at opposing angles relative to one another. For example, referring back to FIG. 15, a side profile of the blade head 174 is illustrated illustrating that the pilot tooth 176 and adjacent base teeth 178A, 178B are oriented in a cross-cut pattern. The first pilot tooth 176 is oriented to point in a generally downward direction relative to Plane-2, and adjacent base teeth 178A, 178B are each oriented in a generally upward direction relative to Plane-2. The combination of the pilot tooth 176 and adjacent base teeth 178A, 178B being arranged in this configuration results in the side of the blade head 174 (i.e. top or bottom) that the pilot tooth 176 is oriented toward having a leading edge that is distal to the edge defined by the adjacent base teeth 178A, 178B. This particular shape of leading edge may be utilized to reduce skiving or diving when approaching a cutting surface at an angle. For example, it may be advantageous to orient the saw blade cartridge 110 relative to the cutting surface, such as a bone or other biological tissue, such the forward most leading edge defined by the pilot tooth 176 contact the cutting surface first.

Referring to FIGS. 16 to 24, a third configuration of the saw blade cartridge 210 is illustrated. It should be understood that components and/or features of the second configuration of the saw blade cartridge 110 including the same base reference number increased by one hundred, i.e. 10, 110, 210, may operate in a similar or the exact same manner as described above.

Similar to as described above, the third configuration of the saw blade cartridge 210 may comprises a guide bar 211 including a plurality of plates (212, 214, 216), including a first plate 212, a second plate 214, and a third plate 216. The guide bar 211 may be configured such that the third plate 216 may be disposed between the first plate 212 and the second 214. The first, second, and third plates, 212, 214, 216 are constructed in a generally similar fashion as those of the saw blade cartridges 10, 110 described above. However, the configuration of the saw blade cartridge 210 illustrated in FIGS. 16 to 24 is constructed with an alternative configuration of the first, second, and third plates, 212, 214, 216.

Figure 16:
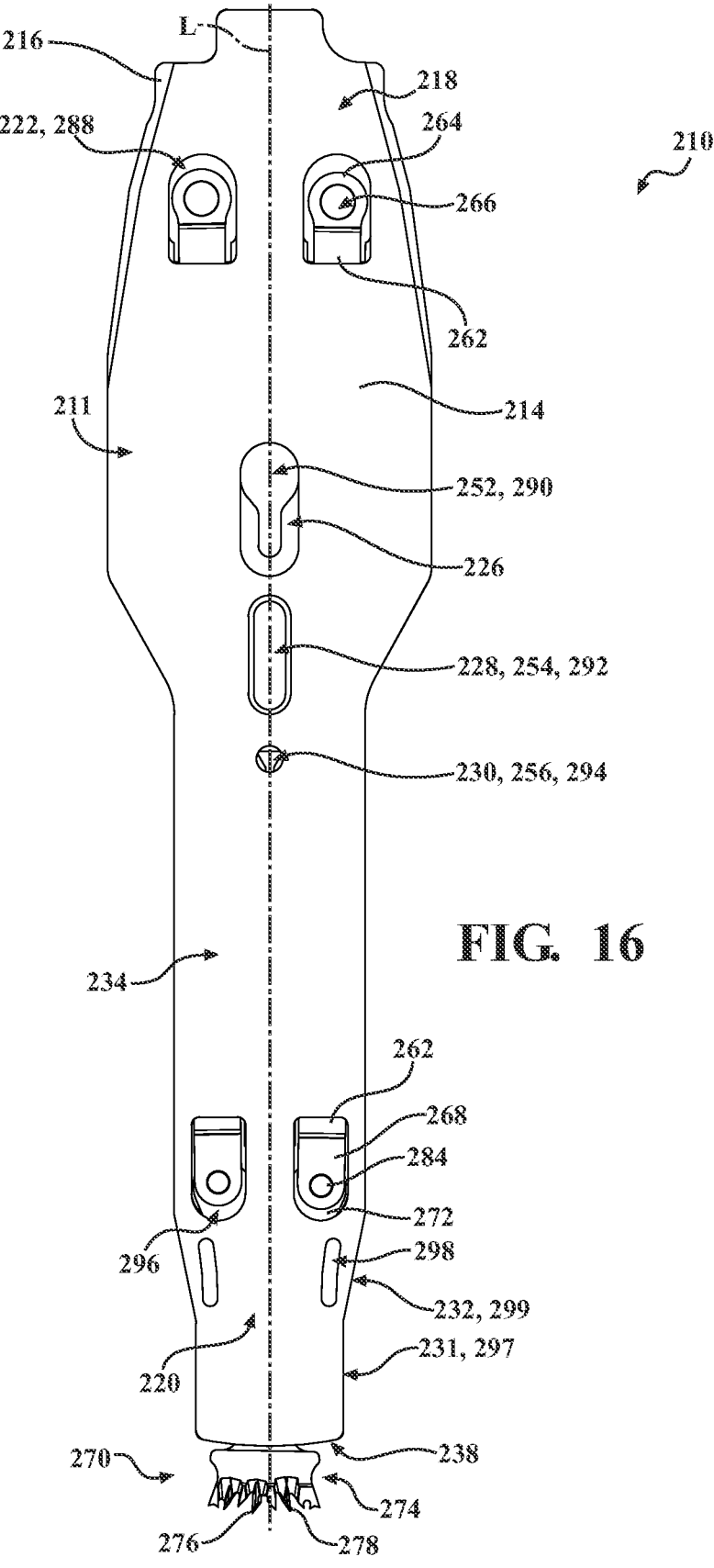
FIG. 16 is a top view of a second configuration of a saw blade cartridge including a distal portion with multiple tapers and a third configuration of a saw blade including a blade head with a plurality of base teeth and a single pilot tooth.
Figure 19:
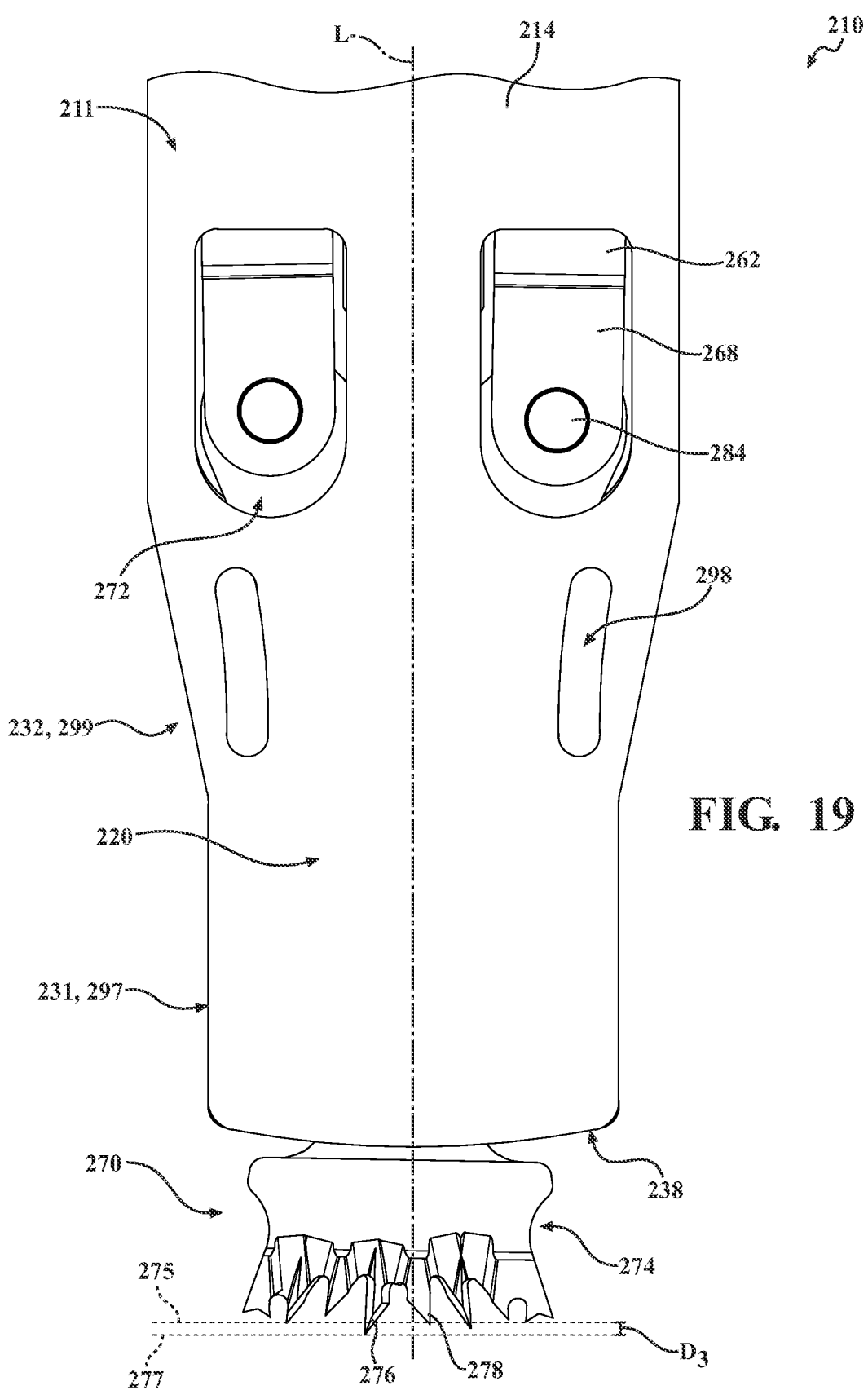
FIG. 19 is a top view of the distal portion of the saw blade cartridge of FIG. 16.
Figure 20:
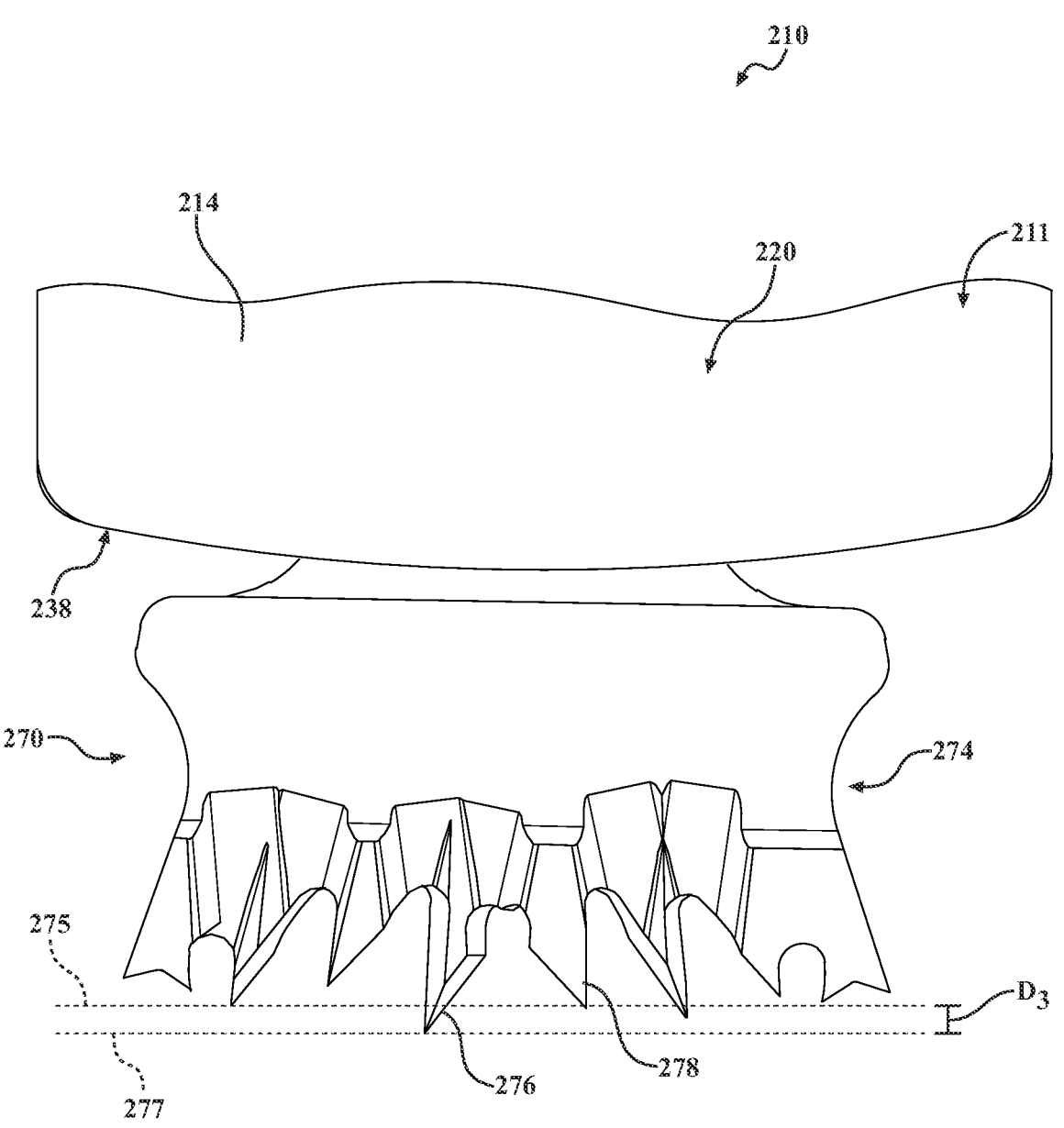
FIG. 20 is a top view of the blade head of the second configuration of the saw blade of FIG. 16, the blade head including the single pilot tooth proximate the central axis off the saw blade and configured to extend distally of the base teeth of the blade head.
Figure 21:
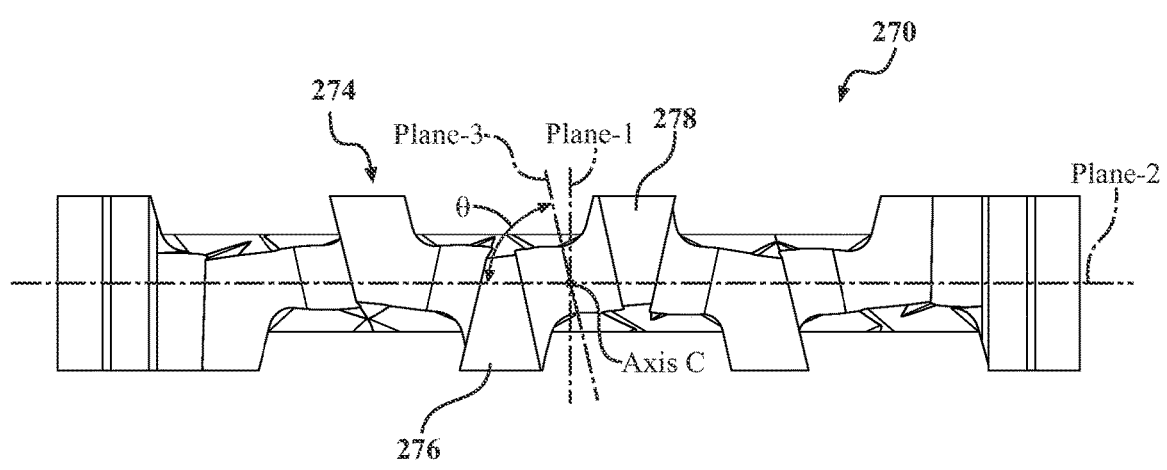
FIG. 21 is a front view of the blade head of the third configuration of the saw blade of the saw blade cartridge of FIG. 16 illustrating a front profile of the base teeth and pilot tooth.
Figure 22:
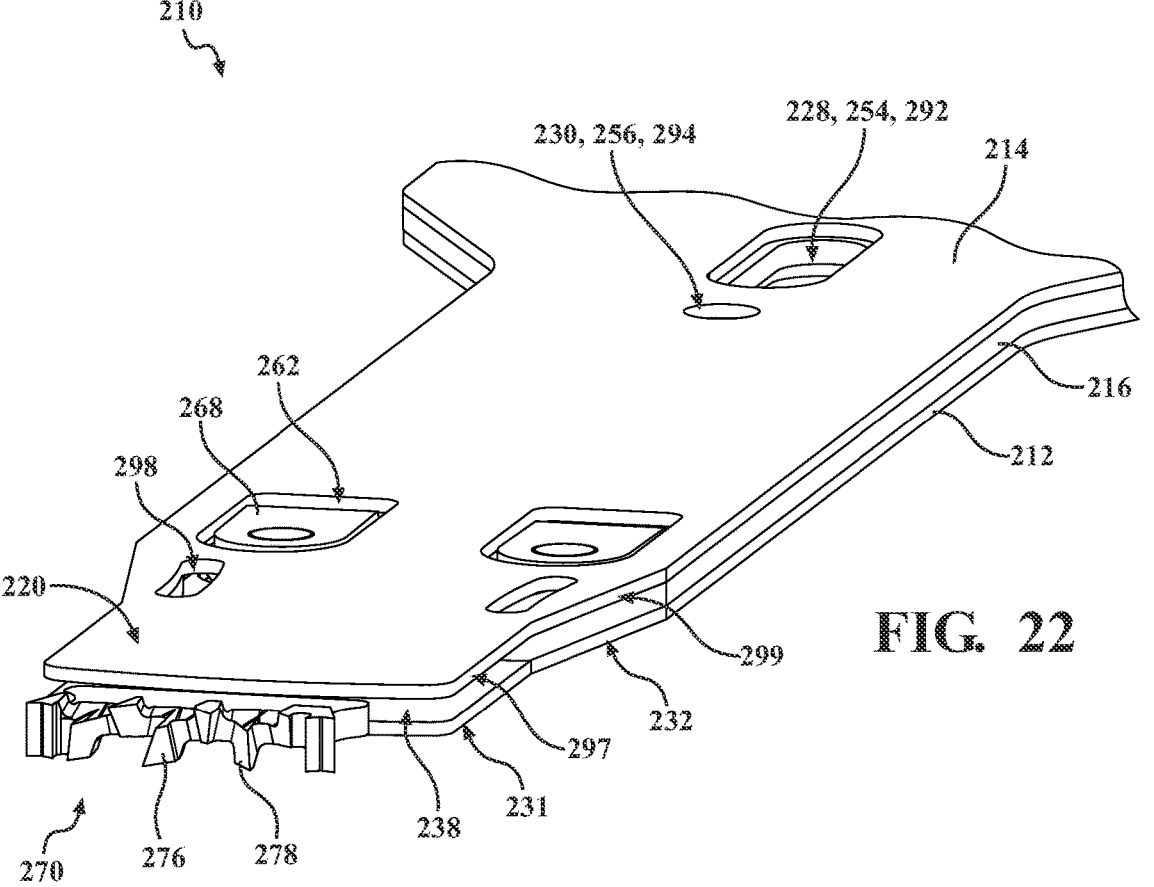
FIG. 22 is a side perspective view of the distal portion of the saw blade cartridge of FIG. 16.

The saw blade cartridge 210 may comprise a saw blade 270 that is the same or similar to either of the saw blades 70, 170 described above. For exemplary purposes, the saw blade cartridge 210, as illustrated in FIG. 16 comprises a saw blade 270 similar to the second configuration of the saw blade 170 described above. The saw blade includes a blade body 272 and a blade head 274. The blade head 274 may comprise two type of teeth, base teeth 278 and one or more pilot teeth 276. For example, as illustrated in FIGS. 18 and 19, the blade head 274 may comprises a single pilot tooth 276. However, as described above, it is contemplated that the blade head 274 may also comprise two or more pilot teeth. The pilot tooth 276 may be disposed proximate the center of the distal surface of the blade head 274. Furthermore, the pilot tooth 276 may be configured to extend a third distance D3 distally beyond the adjacent base teeth 278A, 278B of the blade head 274, as best seen in FIGS. 19 and 20. In operation, with the pilot tooth 276 extends distally beyond the adjacent base teeth 278A, 278B, the pilot tooth 276 is configured to oscillate along a first arc distance 277 as the adjacent base teeth 278 oscillate about a second arc distance 275, such that the first arc distance 277 is distal to the second arc distance 275.

Referring to FIG. 19, a guide bar 211 including an alternative configuration and/or shape of the distal portion 220 is illustrated. As described above, with regard to FIG. 1, the opposing edges of the distal portion 20 of the guide bar 11 may comprise a tapered edge 32, 99 defined by the first and second plates 11. As illustrated in FIG. 19, the distal portion 220 of the guide bar 211 may also be formed such that opposing edges comprise both a tapered portion 232, 299 and a parallel portion 231, 297. For example, the distal portion 220 of the guide bar 211 comprise a tapered edge 232, 299 immediately forward of the middle portion of the guide bar 211. The opposing edges 232, 299 of the first and second plates 212, 214 may be tapered inward toward the longitudinal axis L of the guide bar 211 as you move distally along the guide bar 211. Forward of the tapered edge 231, 299, the guide bar 211 may be formed such that the opposing edges 231, 297 of the first and second plates 212, 214 are generally parallel to the longitudinal axis L of the guide bar 211.

The distal portion of the guide bar 11 may also comprises a pair of generally oval shaped opening 298 in the second plate 214. While two openings 298 are illustrated in the figures, it is contemplated that guide bar may be constructed with only a single opening, or with more than two openings. Furthermore, while the openings are illustrated in the figures as being defined in the second plate 214, it is contemplated that the similar openings may also be defined in the first plate 212. The openings 298 may comprise a curve and/or bend that extends longitudinally along the length of the distal portion 220 of the second plate 214. The opening may be configured to assist with the removal of debris that may become trapped between the first and second plates 212, 214 when the saw blade cartridge 210 is utilized to cut biological tissue.

Figure 23:
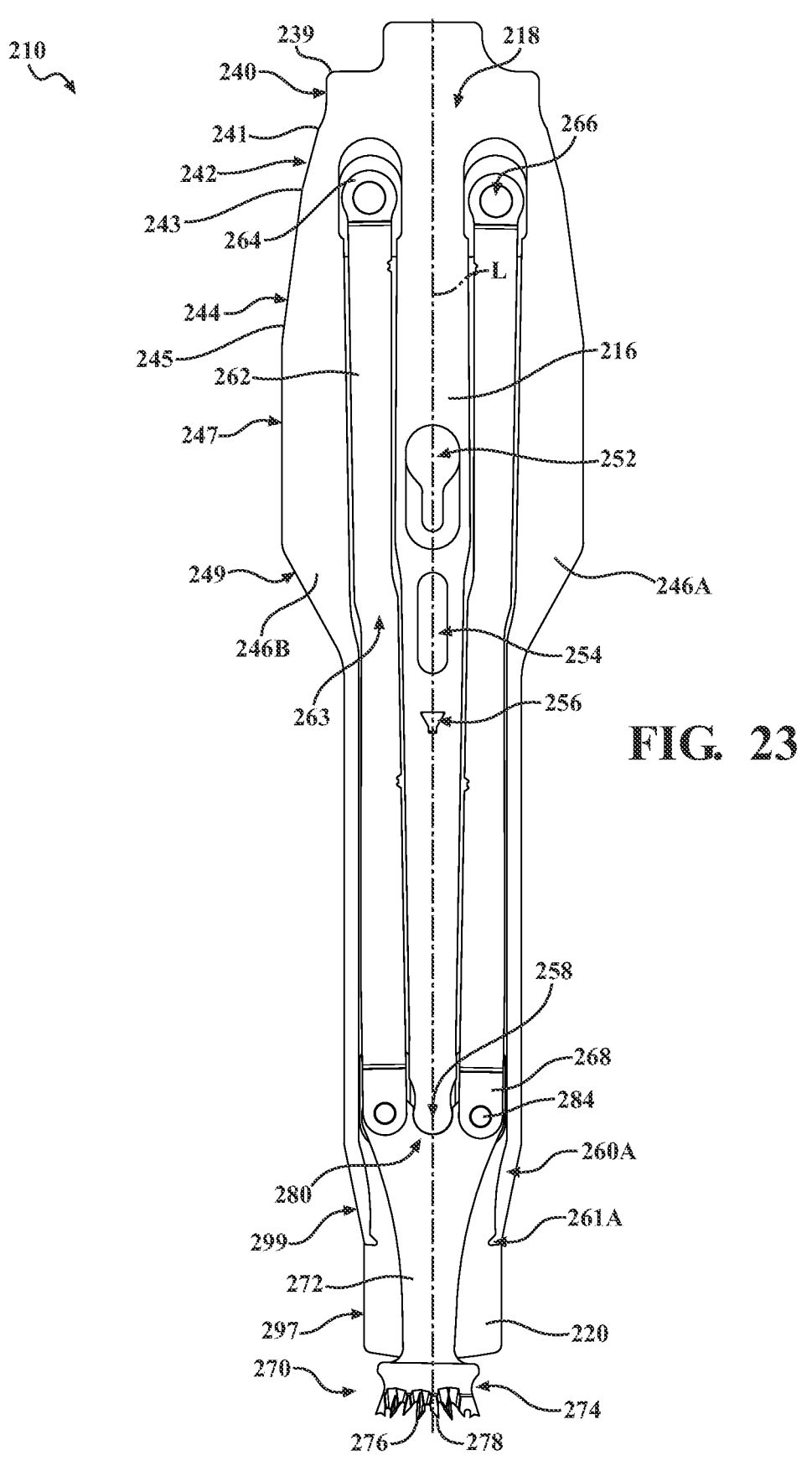
FIG. 23 is a top section al view illustrating the interior features of the saw blade cartridge of FIG. 16.
Figure 24:
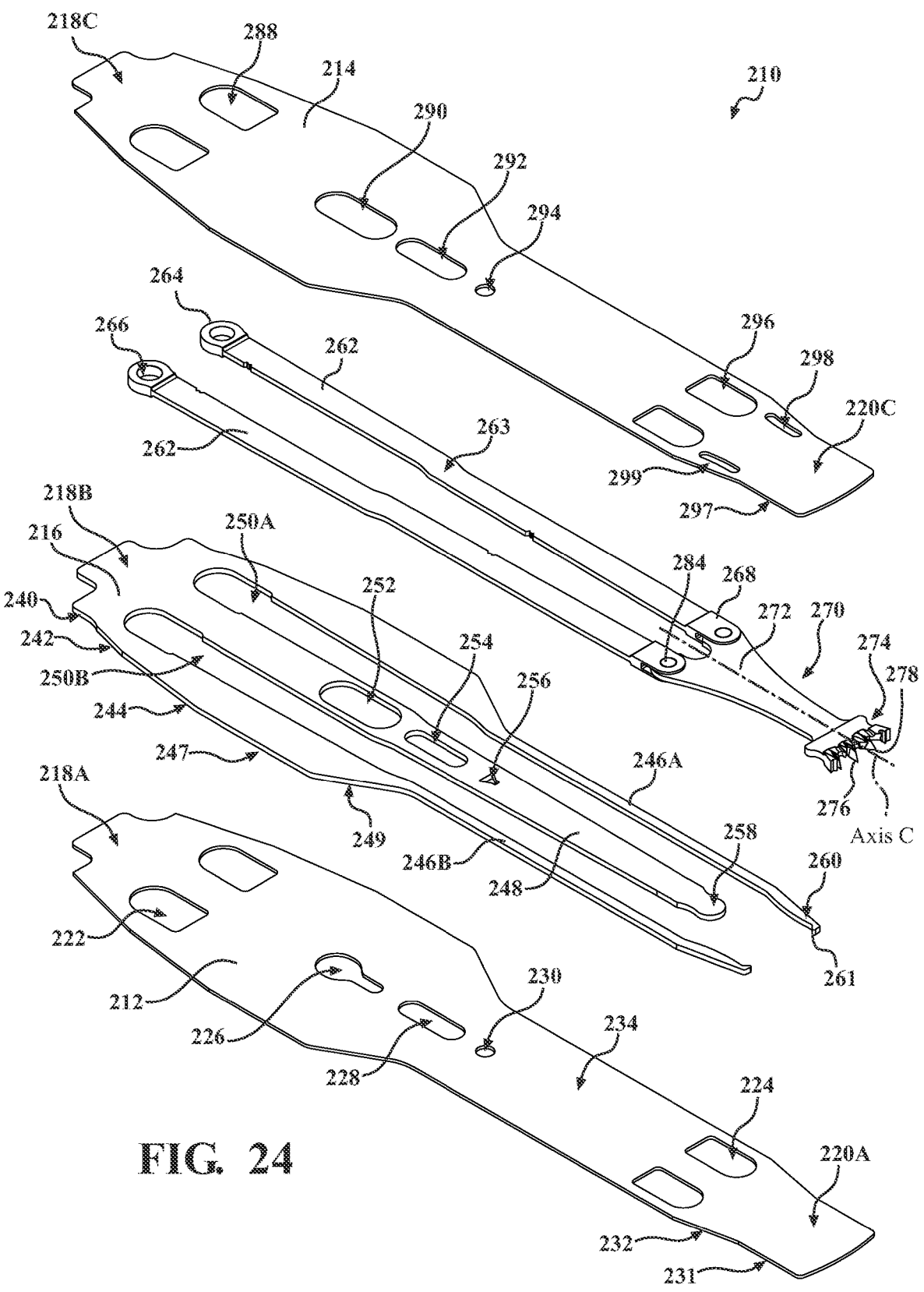
FIG. 24 is an exploded view of the saw blade cartridge of FIG. 16.

Referring to FIG. 23, an alternative configuration of the outer tines 246A, 246B is illustrated. Adjacent the distal end of each tine 246A, 246B, each tine is shaped to have a tab 261 one identified, that extends inwardly to the longitudinal axis L of the guide bar 211. Proximal to the tab 261, each tine 246A, 246B is shaped to have a lobe 260A, 260B, that extends inwardly towards the longitudinal axis L of the guide bar 211. Moving proximally to distally along the tine 246A, 246B, the associated lobe 260A, 260B first curves inwardly toward the longitudinal axis L of the guide bar 211 and then curves outwardly. The third plate 216 is formed so that lobes 260A, 260B are spaced proximally away from tabs 261.

Figure 25:
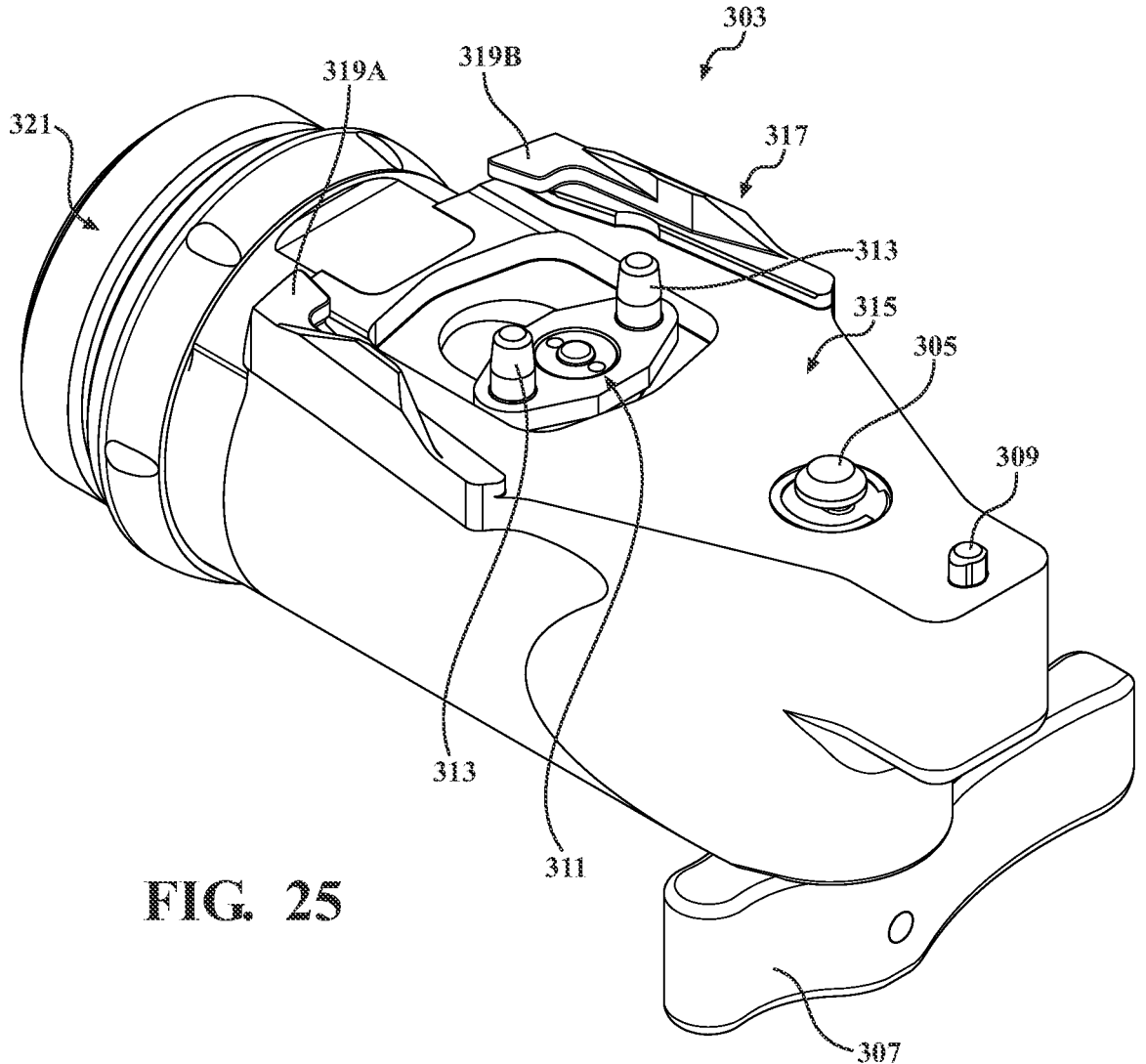
FIG. 25 is a perspective view of an exemplary configuration of a mount for a saw blade cartridge.
Figure 26:
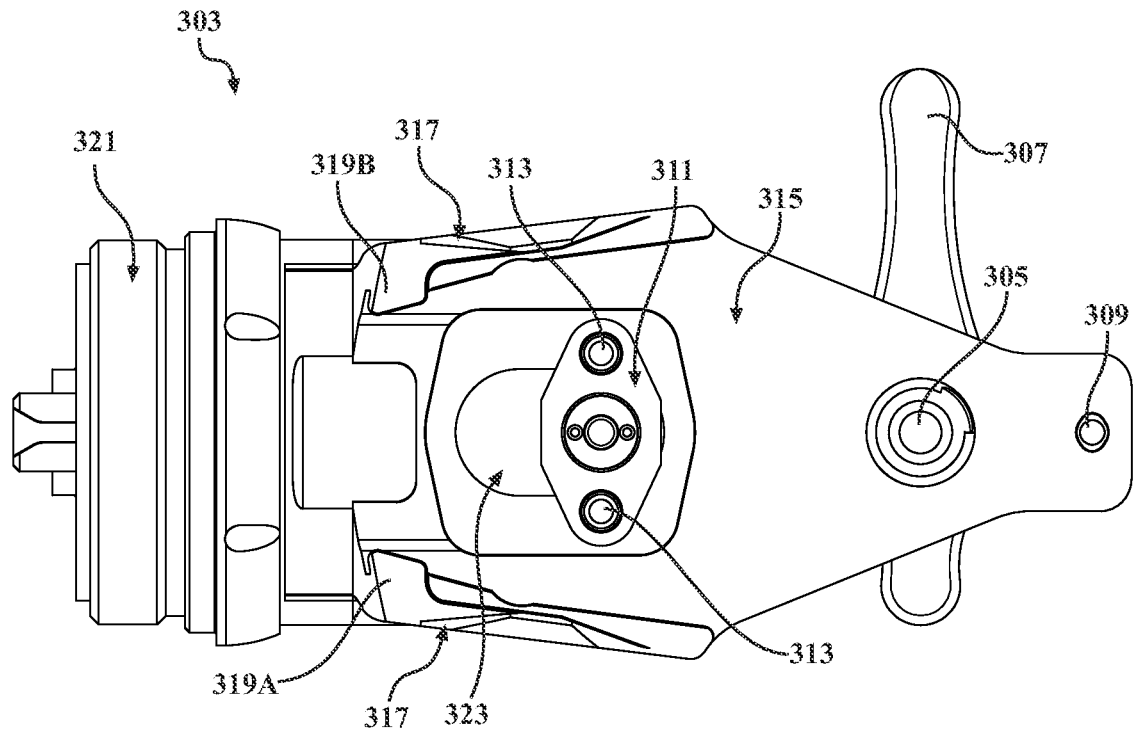
FIG. 26 is a top view of the mount for a saw blade cartridge of FIG. 24.
Figure 27:
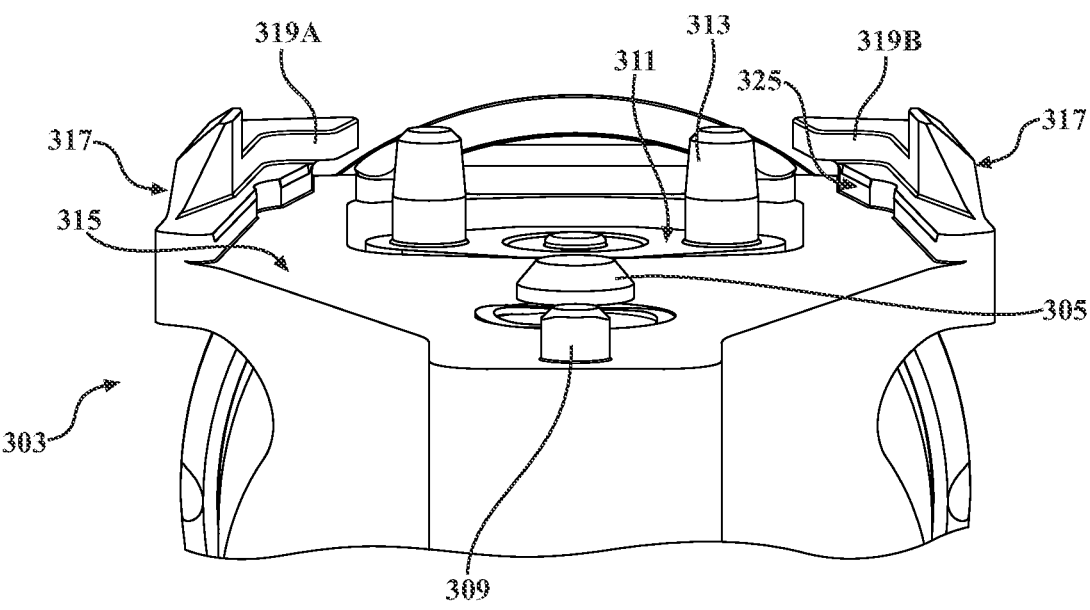
FIG. 27 is a front perspective view of the mount for a saw blade cartridge of FIG. 24.
Figure 28:
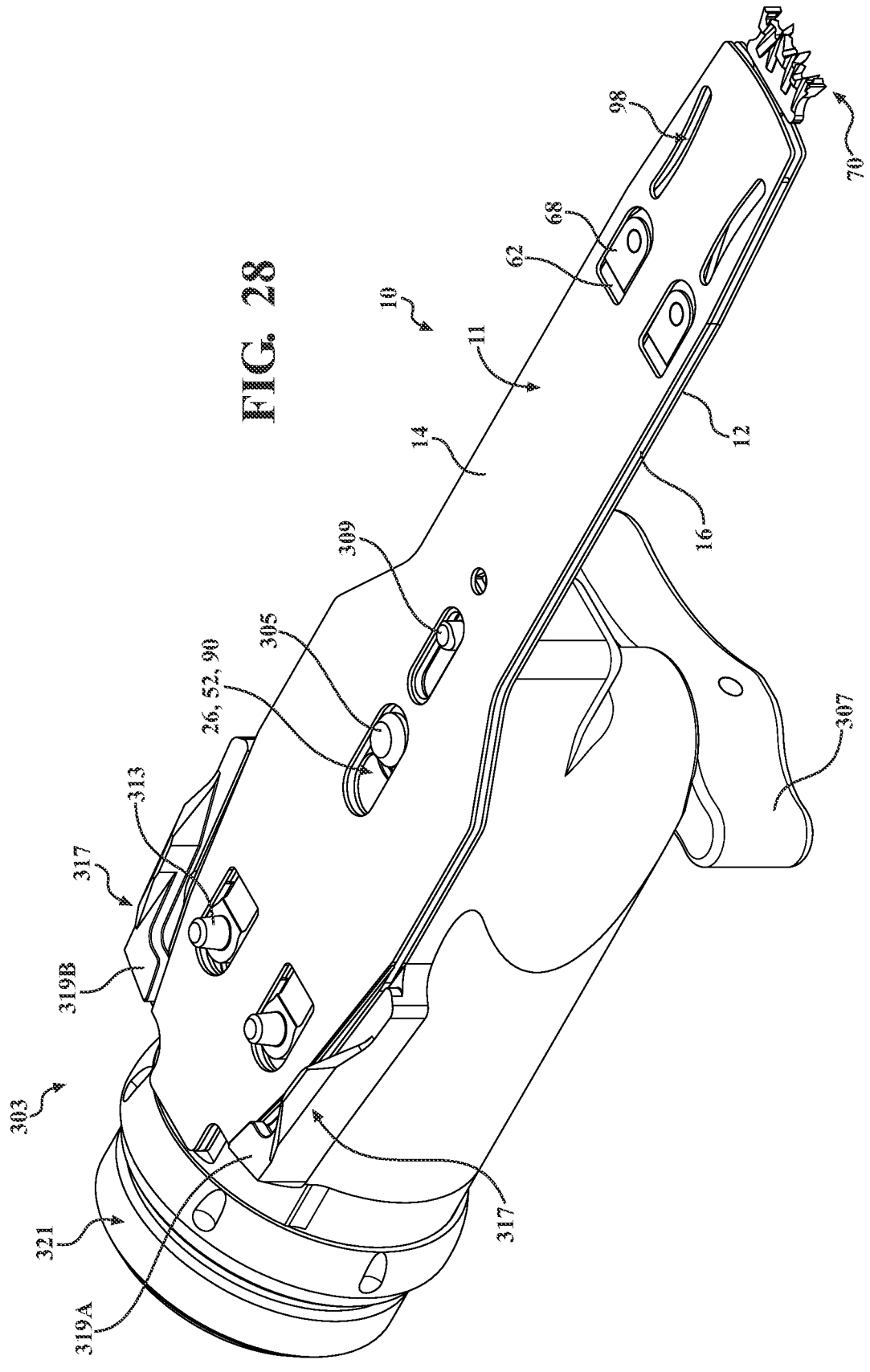
FIG. 28 is a perspective view of the saw blade cartridge of FIG. 1 mounted to the mount of FIG. 24.
Figure 29:
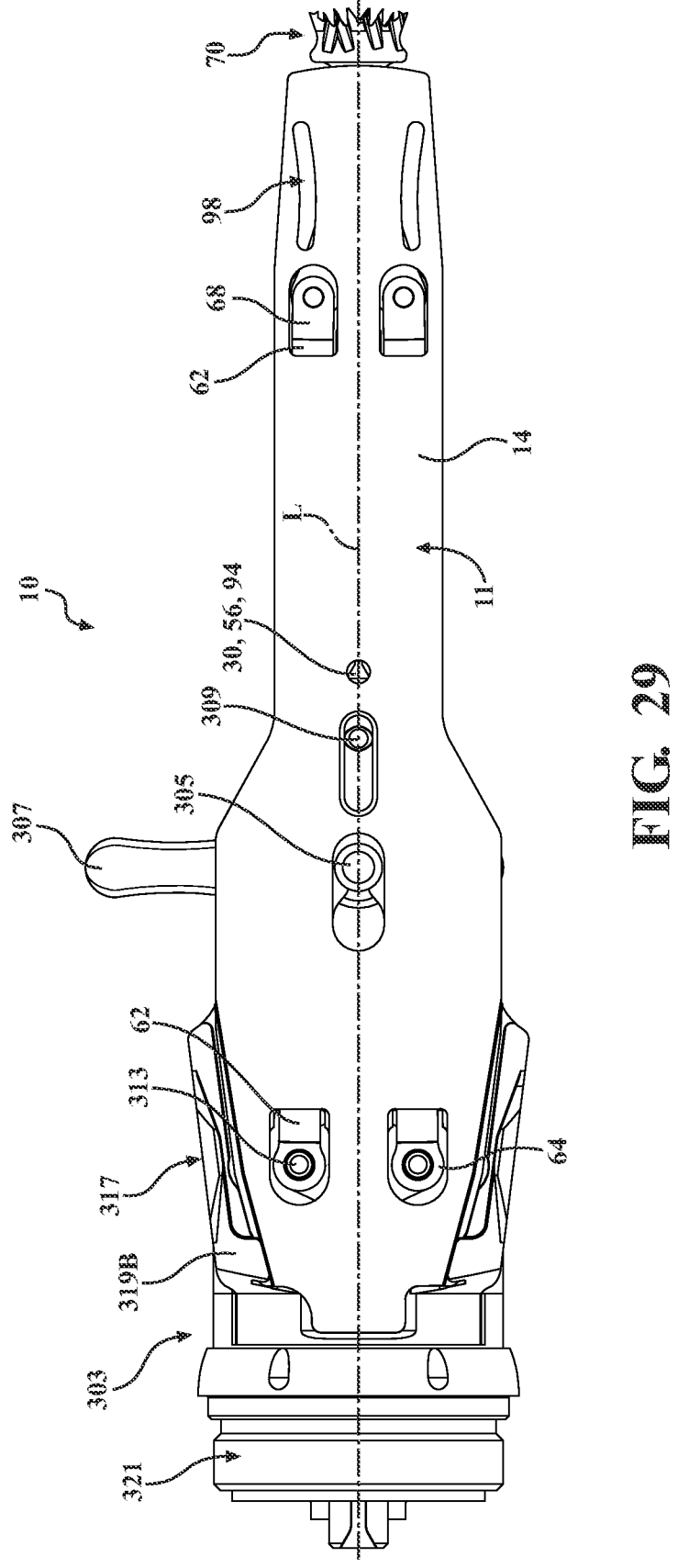
FIG. 29 is a top view of the saw blade cartridge of FIG. 1 mounted to the mount of FIG. 24.
Figure 30:
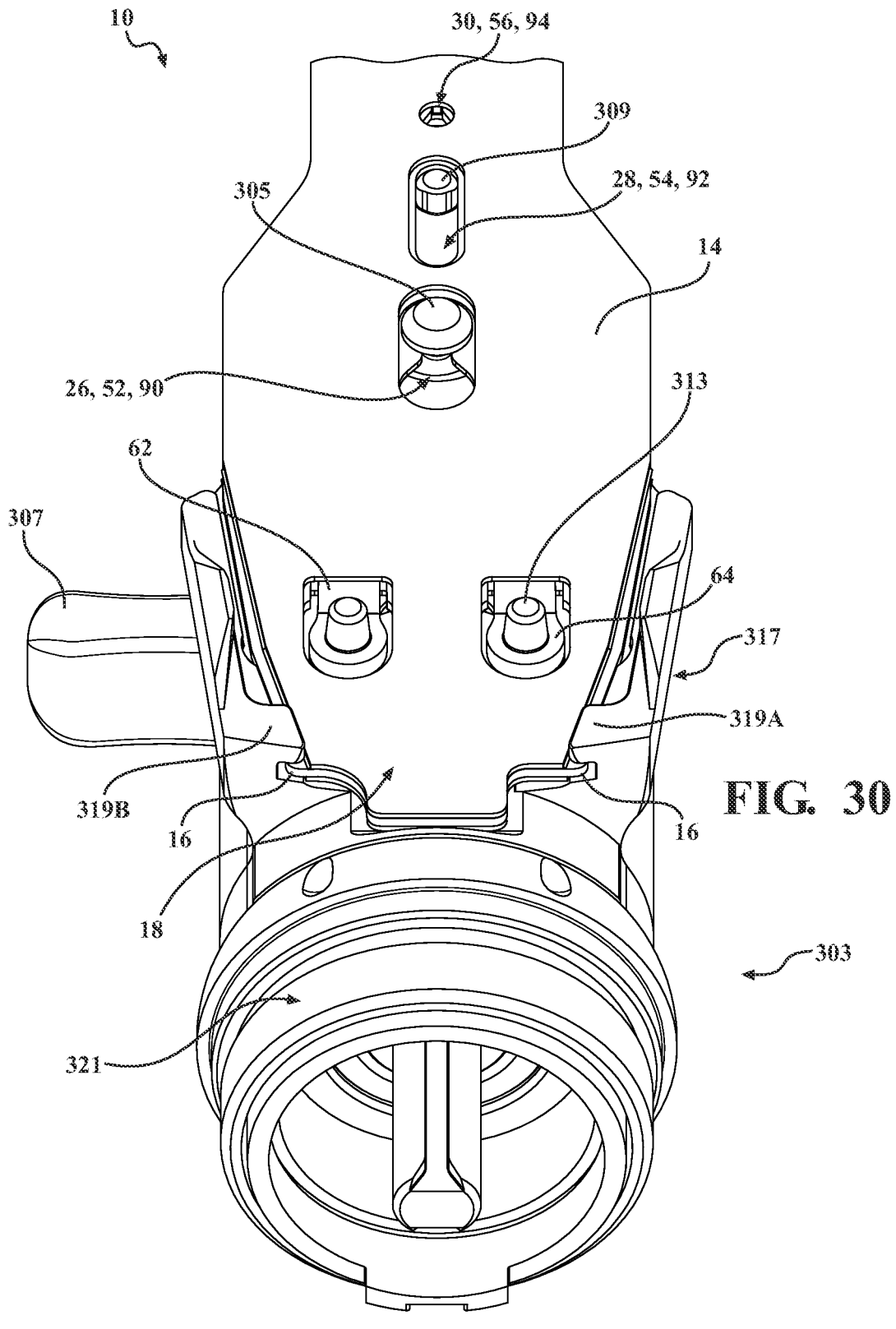
FIG. 30 is a rear perceptive view of the saw blade cartridge of FIG. 1 mounted to the mount of FIG. 24 illustrating the interaction between the mounting features of the proximal portion of the saw blade cartridge with the mount.
Figure 31:
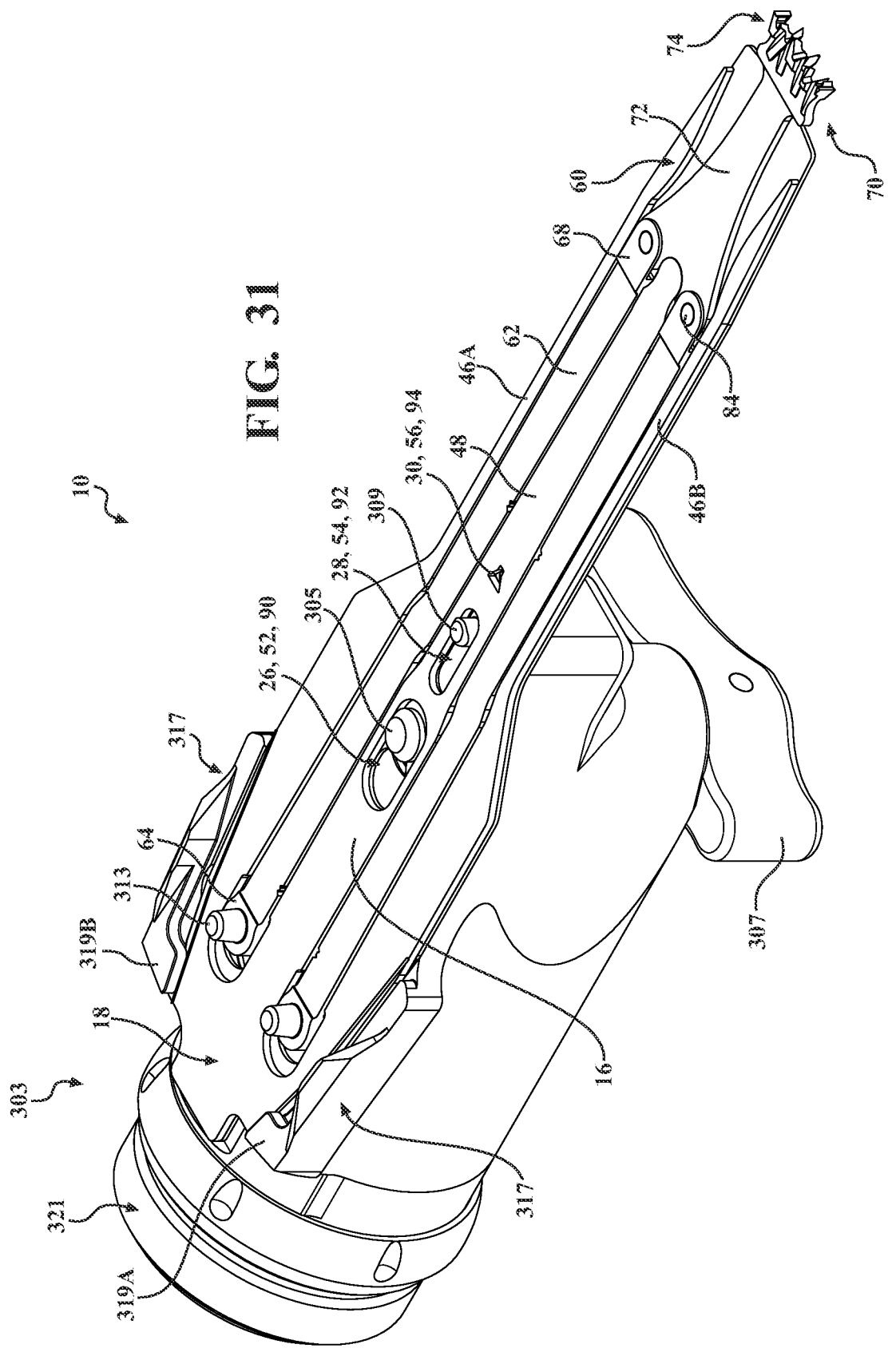
FIG. 31 is a perspective view of a sectional view of the saw blade cartridge of FIG. 1 mounted to the mount of FIG. 24 illustrating how the interior features of the saw blade cartridge interact with the mount.
Figure 32:
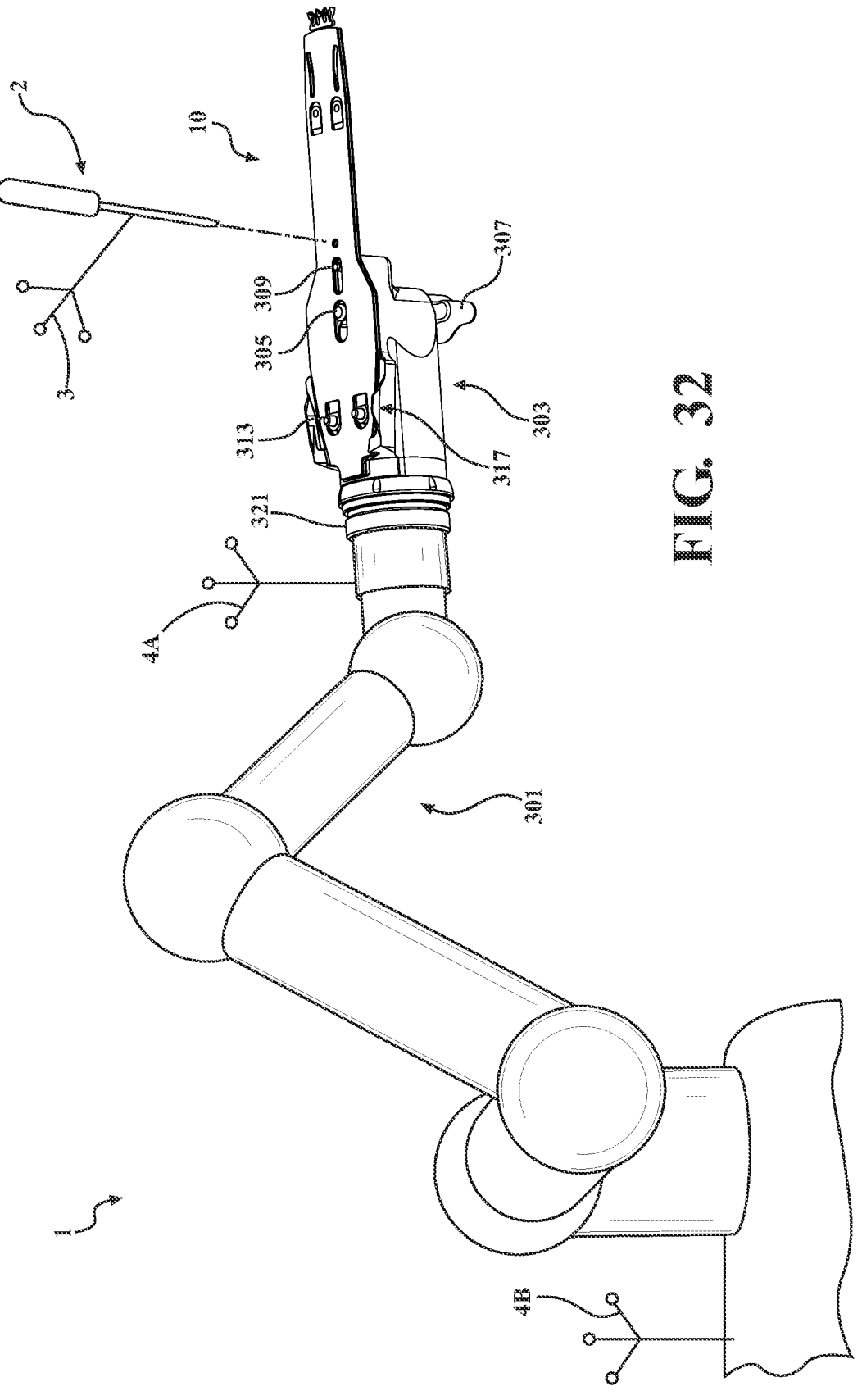
FIG. 32 is a perceptive view of the saw blade cartridge of FIG. 1 mounted to the mount of FIG. 24, the mount connected to a surgical robot used to operate the saw blade cartridge.

Referring to FIGS. 25 to 27, an exemplary configuration of a mount 303 for securing a saw blade cartridge 10, 110, 210 to a surgical manipulator 301 is illustrated. The mount 303 may comprise a coupling rod 305 configured to removably secure the saw blade cartridge 10, 110, 210 to the mount 303. The coupling rod 305 may interact with the openings 26, 52, 90, 126, 152, 190, 226, 252, 290 of the saw blade cartridge 10, 110, 210, such as the key hole opening 26, 126, 226 to removably couple the saw blade cartridge 10, 110, 210 to the mount 303. The coupling rod 305 may comprise a head configured to fit thought the larger portion of the keyhole opening 26, 126, 226, and the shaft of the coupling rod 305 may be configured to fit within the smaller portion of the keyhole opening 26, 126, 226 after the head has been inserted through the larger portion. The larger portion may then be seated above the smaller portion and configured to removably secure the saw blade cartridge 10, 110, 210 to the mount 303. An exemplary configuration of a mount for a saw blade cartridge is disclosed in International Publication No. WO2007/030793 and U.S. Pat. No. 8,696,673, both of which are incorporated herein in their entirety.

The coupling rod 305 may be controlled by a coupling lever 307 configured to manipulate the coupling rod 305 between a locked and unlocked state. For example, the coupling lever 307 may be rotated in one direction to retract the coupling rod 305 to a locked stated configured to secure the saw blade cartridge 10, 110, 210 to the mount 303. Alternatively, the coupling lever 307 may be rotated in the opposite direction to extend or advance the coupling rod 305 to an unlocked stated configured to allow for installation and/or removal of the saw blade cartridge 10, 110, 210 from the mount 303.

The mount may further comprise an alignment feature 309 configured to interact with the opening 28, 54, 92, 128, 154, 192, 228, 254, 292 in each of the first, second, and/or third plates 12, 14, 16, 112, 114, 116, 212, 214, 216. The alignment feature 309 may comprise a pin configured to be inserted through the opening 28, 54, 92, 128, 154, 192, 228, 254, 292 in each of the first, second, and/or third plates 12, 14, 16, 112, 114, 116, 212, 214, 216 when the saw blade cartridge 10, 110, 210 is coupled to the mount 303. alignment feature 303 may be sized to simultaneously engage opposing lateral surfaces of the first opening 28, 54, 92, 128, 154, 192, 228, 254, 292. The alignment feature 309 may be defined to have a round, oval, square, diamond, or similar polygonal shape. While the shape is not critical, in configurations where the alignment feature 309 is intended to provide the functionality of aligning the saw blade cartridge 10 with the surgical manipulator 301, the width of the surgical alignment feature 309 (as measured in a direction generally perpendicular to the lateral axis L of the saw blade cartridge 10) may be sized to simultaneously engage opposing lateral surfaces of the first opening 28, 54, 92, 128, 154, 192, 228, 254, 292. The combination of the coupling rod 305 and the alignment feature 309 may be configured to orient the longitudinal axis L of the saw blade cartridge 10, 110, 210 with the mount 303. Proper and precise alignment of the saw blade cartridge 10, 110, 210 with the mount can be particularly advantageous when the saw blade cartridge 10, 110, 210 and/or the mount 303 do not have their own dedicated tracker. For example, the pose of the saw blade cartridge 10, 110, 210 may be determine based on a tracker 4A, 4B coupled to the surgical manipulator 301 and/or the mount 303 and a transformation based on known information about the mount 303 and/or the saw blade cartridge 10, 110, 210. In this particular scenario, the alignment of the saw blade cartridge 10, 110, 210 with the mount 303 is important to accurately tracking the pose of the saw blade cartridge 10, 110, 210.

The mount 303 may also comprise a mount surface 315 configured to receive the saw blade cartridge 10, 110, 210. When the saw blade cartridge 10, 110, 210 is coupled to the mount, bottom surface of the proximal portion of the first plate 12, 112, 212 may seated adjacent the mounting surface 315. When the coupling rod 305 is in the locked state, the coupling rod 305 may be configured to press the saw blade cartridge 10, 110, 210 against the mount surface 315 to hold the saw blade cartridge 10, 110, 210 in place.

A method of the surgical saw blade 10 to the surgical manipulator 301 may include inserting the alignment feature 309 of the surgical manipulator 301 in a first opening 28, 54, 92, 128, 154, 192, 228, 254, 292 of the surgical saw blade 10 and inserting the coupling rod 305 of the surgical manipulator 301 in the second opening 26, 52, 90, 126, 152, 190, 226, 252, 290 of the surgical saw blade 10. The method may also includes sliding the surgical saw blade 10 proximally toward the surgical manipulator 301 causing each of the alignment feature 303 and the coupling rod 305 to move from a proximal position within each of the first opening 28, 54, 92, 128, 154, 192, 228, 254, 292 and the second opening 26, 52, 90, 126, 152, 190, 226, 252, 290 respectively to a distal position within each of the first opening 28, 54, 92, 128, 154, 192, 228, 254, 292 and the second opening 26, 52, 90, 126, 152, 190, 226, 252, 290. The alignment feature 309 may be sized and/or shaped to simultaneously engage opposing lateral surfaces of the first opening 28, 54, 92, 128, 154, 192, 228, 254, 292 when positioned within the distal position of the first opening 28, 54, 92, 128, 154, 192, 228, 254, 292 to axially align the surgical saw blade 10 relative to the surgical manipulator 301 as the surgical saw blade 10 is slid proximally toward the surgical manipulator 301. It is further contemplated that the alignment feature 309 may be sized and/or shaped to engage the first opening 28, 54, 92, 128, 154, 192, 228, 254, 292 to transversely align the surgical saw blade 10 relative to the surgical manipulator 301.

The mount 303 may also comprise a drive rod 311 for actuating the saw blade 70, 170, 270 of the saw blade cartridge 10, 110, 210. The drive rod 311 may comprise at least one drive pin 313 configured to be seated in the holes 66, 166, 266 formed in a drive link foot 64, 164, 264. While a pair of drive pins are illustrated in the figures, it is contemplated that the mount 303 may be configured to actuate the saw blade 70, 170, 270 of the saw blade cartridge 10, 110, 210 with only a single drive pin 313. In operation, the drive rod 311 may be oscillated and/or partially rotated back and forth causing the drive pin(s) to reciprocate, and in turn reciprocating the drive link 62, 162, 262.

The drive rod 311 may also comprise a biasing member (not shown) configured to urge the drive rod 311 in a proximal direction toward a locked position. The force of biasing member may be overcome by pulling the drive rod 311 in a distal direction toward a loading position. In operation, the holes 66, 166, 266 formed in a drive link foot 64, 164, 264 may be seated over the drive pin(s) 313 while the drive rod 311 is in the locked position. The saw blade cartridge 10, 110, 210 may then be pulled distally (forward) to overcome the force of the biasing member and urging the drive rod toward the loading position where the saw blade cartridge 10, 110, 210 can be mounted to the mount 303. Once the saw blade cartridge 10, 110, 210 is loaded, i.e. the coupling rod is inserted through the key hole opening 26, 126, 226 and the proximal portion 18, 118, 218, of the first plate 12, 112, 212 is adjacent the mounting surface 315, the saw blade cartridge 10, 110, 210 may be released and the biasing member will move the saw blade cartridge 10, 110, 210 proximally and until it has reached the locked position.

The mount 303 may further comprise a bracket 317 positioned on opposing sides of the mounting surface 315. The bracket may extend upward from the mounting surface and comprise a tab 319 that is configured to at least partially extend over the top surface of the second plate 14, 114, 214 of the saw blade cartridge 10, 110, 210 when the saw blade cartridge 10, 110, 210 is coupled to the mount 303. The purpose of the pulling the saw blade cartridge 10, 110, 210 distally (forward) to load the saw blade cartridge 10, 110, 210 on the mount is to allow the proximal portion 18, 118, 218 of the saw blade cartridge 10, 110, 210 to clear the tabs 319 of the brackets 317. Then when the biasing member moves the saw blade cartridge 10, 110, 210 proximally, a portion of the proximal portion 18, 118, 218 of the saw blade cartridge 10, 110, 210 is seated between the tab 319 and the mounting surface 315.

The bracket 317 may also comprise a tapered surface 325. The tapered surface 325 may be configured to match the various tapers of the opposing edges of the proximal portion 18, 118, 218 of the third plate 16, 116, 216 for the purpose of orient and/or securing the saw blade cartridge 10, 110, 210 to the mount 303. The tapered surface 325 may be configured to match the various tapers of the opposing edges of the proximal portion 18, 118, 218 of the third plate 16, 116, 216 to such the biasing member urging the saw blade cartridge 10, 110, 210 proximally will cause the proximal portion 18, 118, 218 of the third plate 16, 116, 216 to be wedged between the opposed tapered surface 325 of the bracket 317 to axially align the surgical saw blade 10 relative to the surgical manipulator 301. It is also contemplated that the third plate 16, 116, 216 to be wedged between the opposed tapered surface 325 of the bracket 317 to transversely align the surgical saw blade 10 relative to the surgical manipulator 301. The opposing edges of the proximal portion 18, 118, 218 of the third plate 16, 116, 216 formed with various segments having different taper angles and the tapered surface 325 of bracket 317 being formed to match can provide improved alignment of the saw blade cartridge 10, 110, 210 with the mount 303, improving the accuracy of the navigation of the saw blade cartridge 10, 110, 210.

Referring to FIGS. 28 to 32, an exemplary configuration of the surgical assembly 1 is illustrated, including a saw blade cartridge 10, 110, 210 coupled to a mount 303 of a surgical manipulator 301.

In operation, the saw blade cartridge 10, 110, 210 may be coupled to a surgical manipulator 301, such as a robot arm, or a hand-hand power tool, including a hand-held robotic handpiece. The saw blade cartridge 10, 110, 210 may be fitted to a mount 303 of the surgical manipulator 301. To accomplish this, each drive pin 313 of the mount 303 is seated in a separate one of the holes 66, 166, 266 formed in a drive link foot 62, 162, 262, and the saw blade cartridge 10, 110, 210 may be pulled forward pulling the drive pins 313 and the driver mechanism 311 forward. The saw blade cartridge 10, 110, 210 may then be lowered such that the bottom surface of the first plate 12, 112, 212 is positioned adjacent the mounting surface 315 of the mount 313. In doing so, the coupling rod 305 of the mount may be inserted through the overlapping openings 26, 52, 90, 126, 152, 190, 226, 252, 290 of the saw blade cartridge 10, 110, 210. The coupling rod 305 may then be lowered using the coupling lever 307 to lower the head of the coupling rod 305 onto the guide bar 11, 111, 211 so the head of the coupling rod 305 presses against the top surface of which if the plates 12, 14, 16, 112, 114, 116, 212, 214, 216 include the key-hole shaped opening 26, 126, 226. This press action holds the saw blade cartridge 10, 110, 210 to the mount 303. When the saw blade cartridge 10, 110, 210 is secured to the mount 303, the drive pins 313 and drive links 311 cooperate to urge the saw blade cartridge 10, 110, 210 proximally. The proximal portion 18, 118, 218 of the saw blade cartridge 10, 110, 210 is seated adjacent the mount surface 315.

The saw blade cartridge 10, 110, 210 may be actuated by actuating of the motor (not shown) of the surgical manipulator 301. The actuation of the motor results in the back-and-forth oscillation of the drive pins 313. The movement of the drive pins 313 causes the drive links 62, 162, 262 to engage in opposed back and forth reciprocation of the drive links 62, 162, 262. The opposed back and forth motion of the drive links 62, 162, 262 causes the saw blade 70, 170, 270 to pivot back and forth around the head 58. 158, 258 of the guide bar 11, 111, 211. The pivoting action of the saw blade 70, 170, 270 causes oscillation of the blade head 74, 174, 274, and by extension the blade teeth 76, 78, 176, 178, 276, 278 causing the teeth to cut the tissue against which the saw blade cartridge 10, 110, 210 is pressed.

Once the saw blade cartridge 10, 110, 210 has been mounted to the mount 303 and/or the surgical manipulator 301, the reference feature 56, 156, 256 of the saw blade cartridge 10, 110, 210 may be utilized to register and/or verify the pose of the saw blade cartridge 10, 110, 210 with the navigation system. A method of registering the saw blade cartridge 10, 110, 210 with a navigation system may comprise touching a registration tool or instrument 2 including a first tracking device 3 to the reference feature 56, 156, 256 on the inner plate 16, 116, 216 by inserting a distal end of the instrument through the aperture 30, 94, 130, 194, 230, 294 in one of the first plate 12, 112, 212 or the second plate 14, 114, 214. The reference feature 56 156, 256 may be configured to register the position and/or orientation of the saw blade cartridge 10, 110, 210 to the navigation system, and/or verify the position and/or orientation of the saw blade cartridge 10, 110, 210 in the surgical navigation system. The method may further comprise tracking the position and orientation of the first tracking device 3 as the instrument 1 is touched to the reference feature 56, 156, 256 on the saw blade cartridge 10, 110, 210 and determining an actual position and orientation of the reference feature 56 156, 256. The method may also comprise determining an expected position of the reference feature 56 156, 256 based on predetermined geometrical data corresponding to the relationship between a mounting feature and the reference feature 56, 156, 256 of the saw blade cartridge 10, 110, 210 as described above.

The actual position and orientation of the reference feature 56 156, 256 may further be configured to identify the type of saw blade cartridge 10, 110, 210. For example, the position of the reference feature 56 156, 256 may vary between different types and/or size blades. Therefore, when the actual position and orientation of the reference feature 56 156, 256 is determine, the navigation system may be configured to identify the type of saw blade cartridge 10, 110, 210 based on the actual position and orientation of the reference feature 56 156, 256. This may include identifying a characteristics of the saw blade cartridge 10, 110, 210, such as, but not limited to, a type of the blade, a blade thickness of the blade head, a tooth configuration of the blade head, a length of the guide bar, and/or a width of the guide bar 11, 111, 211.

Figure 33:
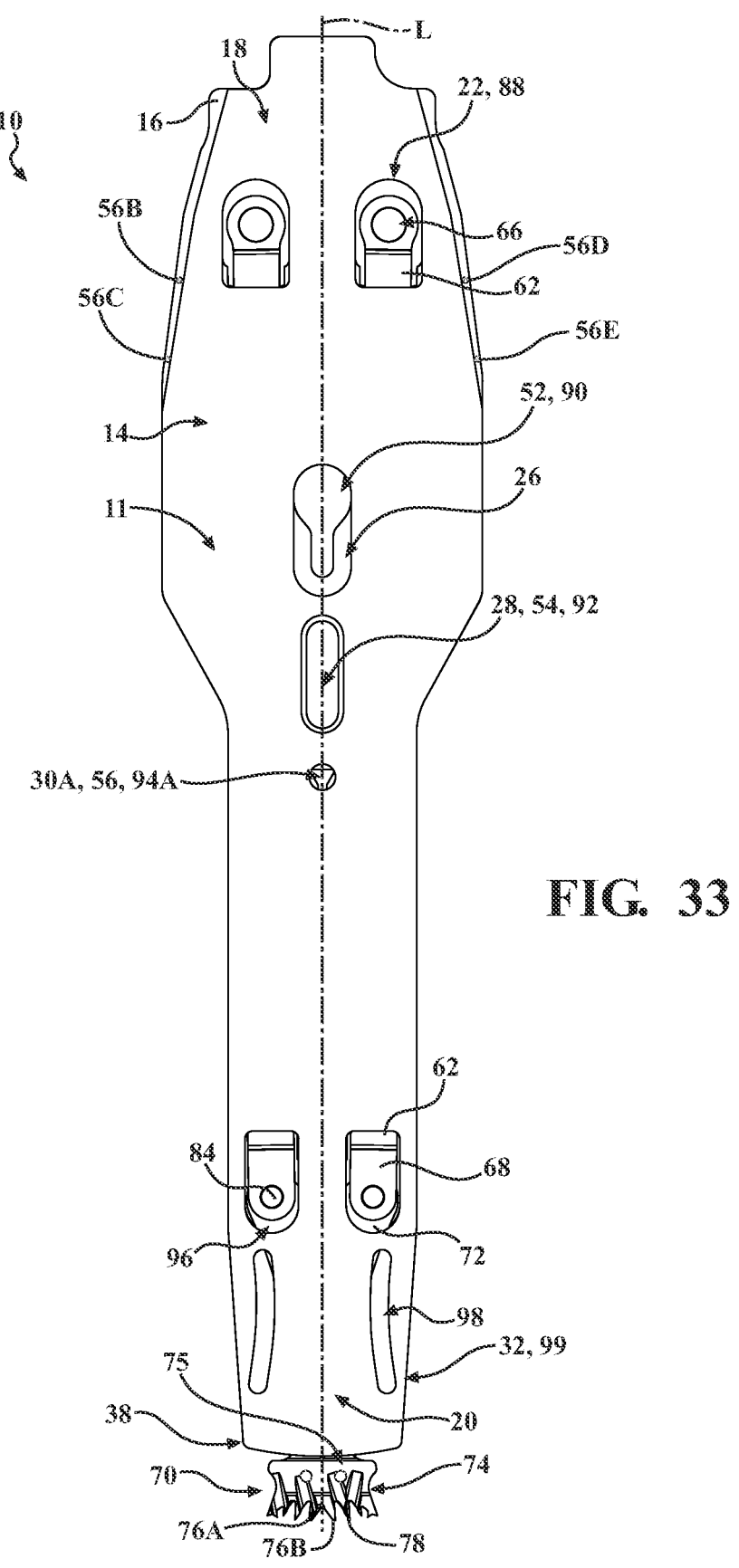
FIG. 33 is a top view of the saw blade cartridge of FIG. 1 including a fourth configuration of a saw blade and an inner plate including a plurality of reference features.
Figure 34:
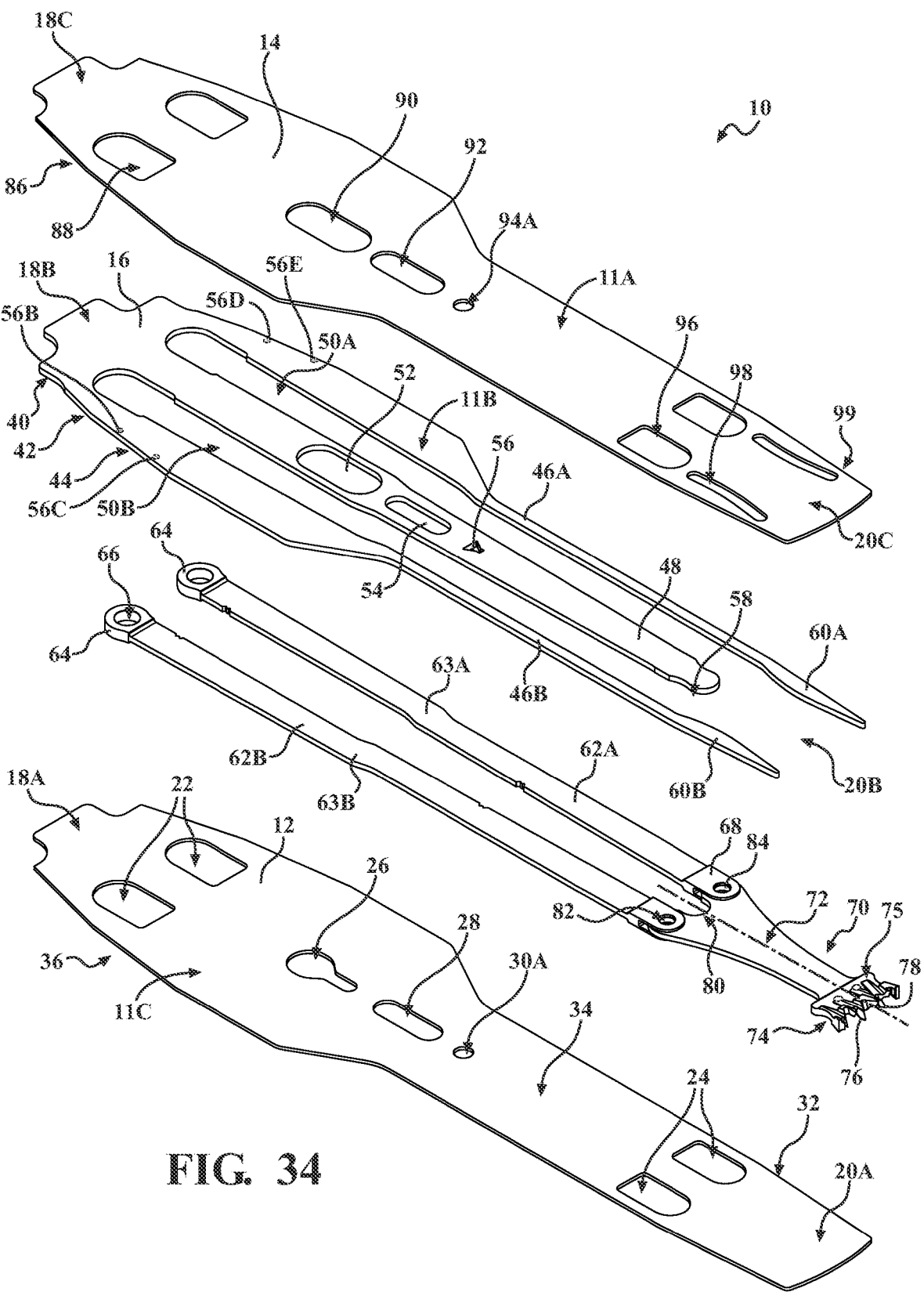
FIG. 34 is an exploded view of the saw blade cartridge of FIG. 34.
Figure 35A:
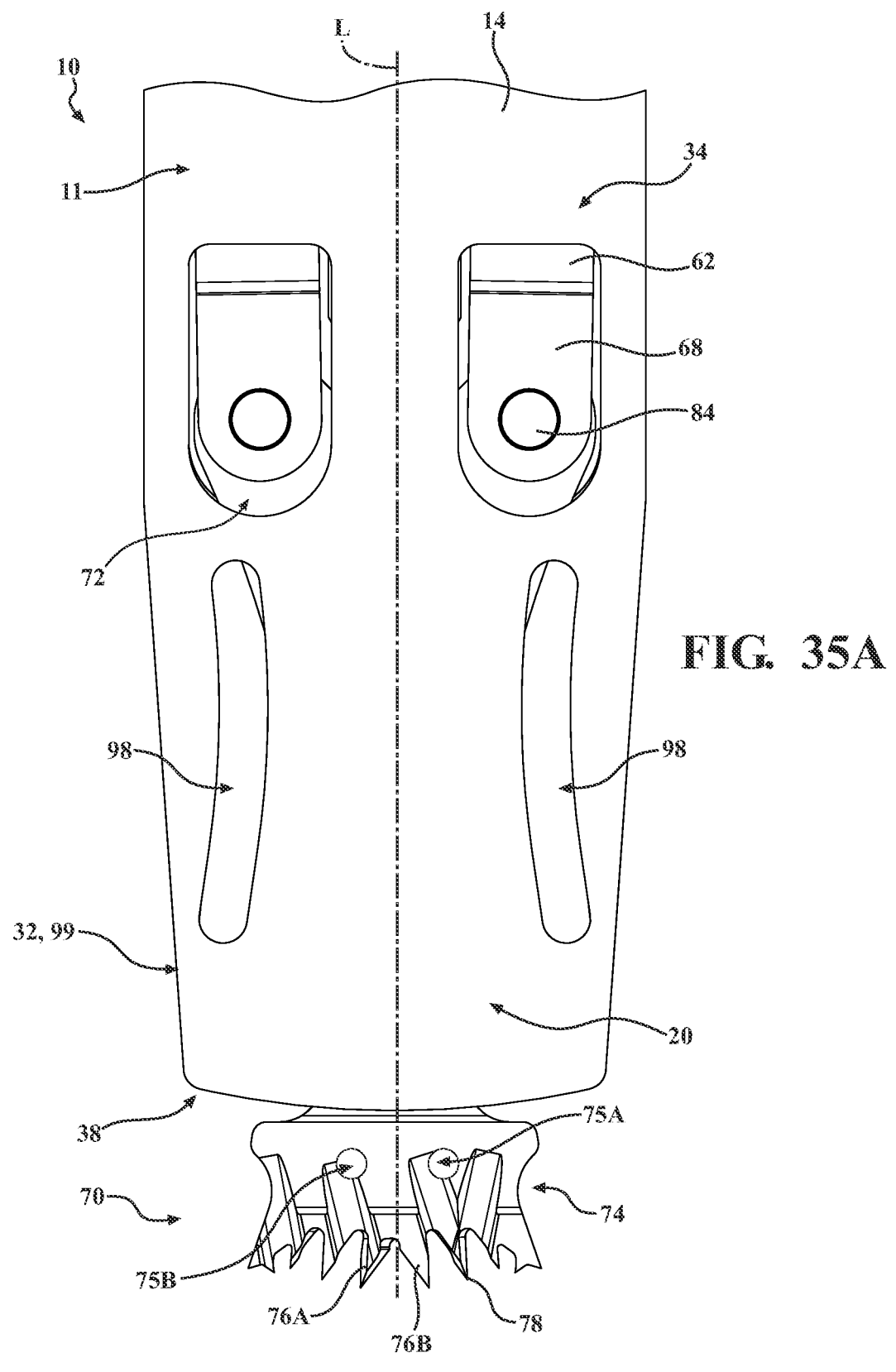
FIG. 35A is a top view of the distal portion of the saw blade cartridge of FIG. 33 including the fourth configuration of a saw blade, the fourth configuration saw blade including at least one aperture in the saw blade.
Figure 35B:
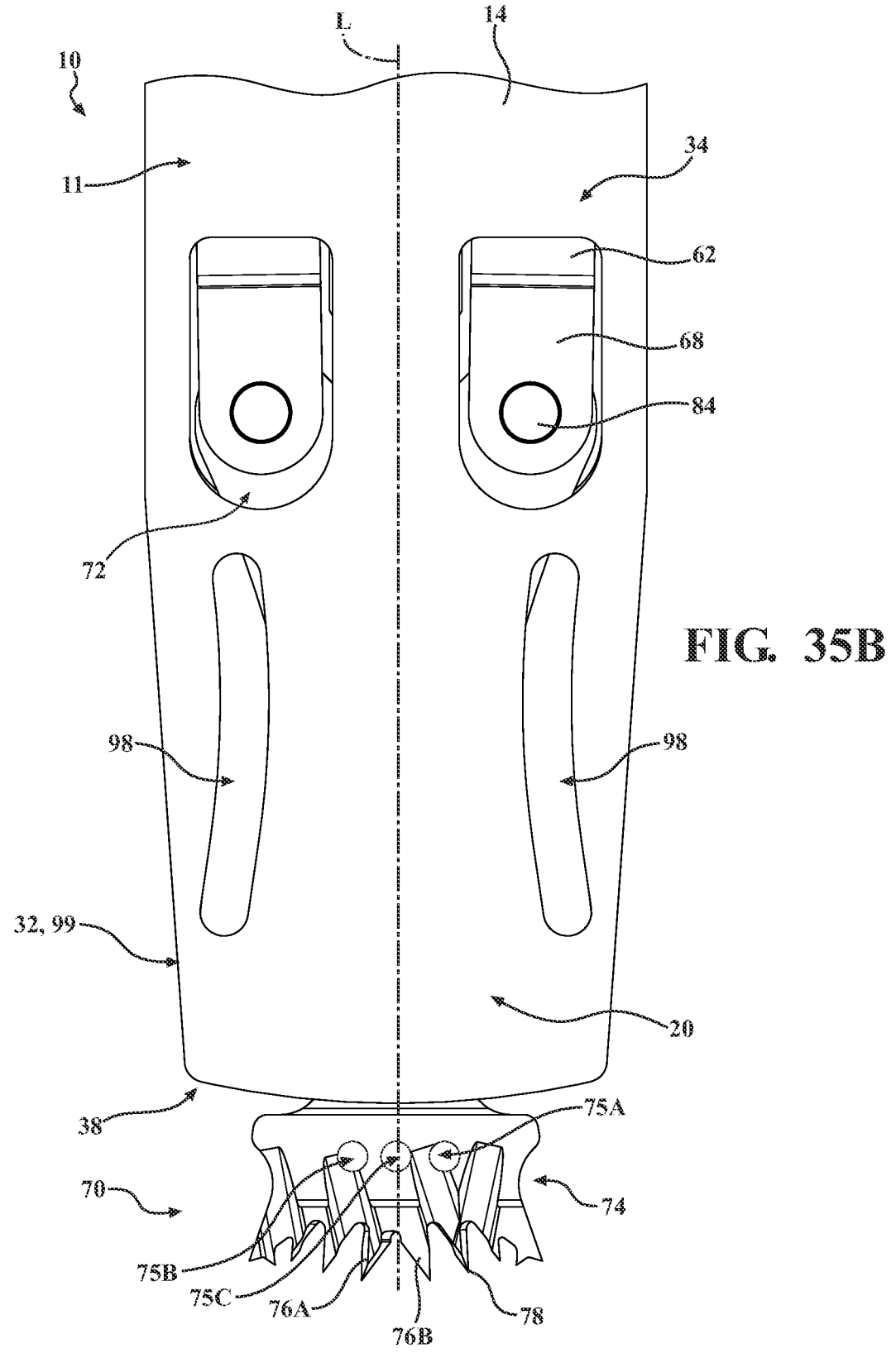
FIG. 35B is a top view of the distal portion of the saw blade cartridge of FIG. 33 including a fifth configuration of a saw blade, the fifth configuration saw blade including a plurality of apertures in the saw blade.
Figure 36:
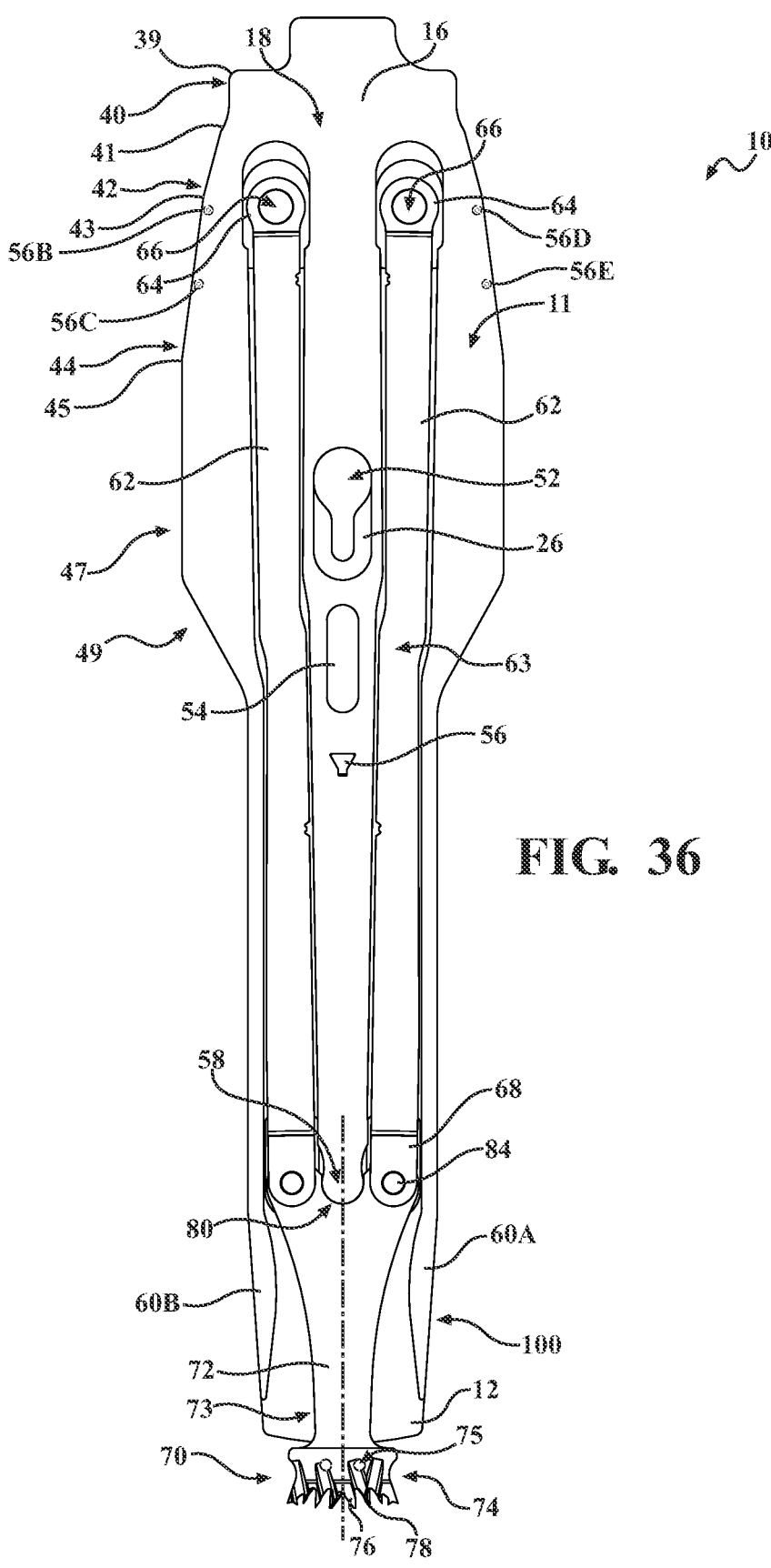
FIG. 36 is a top sectional view illustrating the interior features of the saw blade cartridge of FIG. 33, including the blade with apertures and the inner plate including reference features.

Referring to FIGS. 33 to 36 the saw blade cartridge 10 described above is illustrated including an alternative configuration of reference features 56, 56A, 56B, 56C, 56D. As described above, the saw blade cartridge 10 may comprise a plurality of reference features 56, 56A, 56B, 56C, 56D. FIGS. 33, 34, and 36 show the surgical saw blade cartridge including an exemplary arrangement of reference features 56, 56A, 56B, 56C, 56D. The plurality of reference features 56, 56A, 56B, 56C, 56D may be located on the third plate 16, the first and/or second plates 12, 14 may be shaped to expose the reference features 56, 56A, 56B, 56C, 56D. For example, as illustrated in FIG. 33, the first and/or second plates 12, 14 may comprise an opening 30A, 94A to provide access to the reference feature 56. It is also contemplated that the reference feature(s) 56A, 56B, 56C, 56D may be positioned on a portion of the third plate 16 that is exposed from the first and/or second plates 12, 14. Referring to FIG. 33, a plurality of reference features 56A, 56B, 56C, 56D are defined on the proximal portion 18A of the third plate 16 that extends beyond the outer edge of the first and/or second plates 12, 14. While not illustrated, it is further contemplated that the first and/or second plates 12, 14, may comprise a cut-out, define a recess in an outer edge, and/or define additional apertured and/or openings to provide access to a the reference feature(s) 56 56A, 56B, 56C, 56D defined on the third plate 16. As described above, the reference features 56, 56A, 56B, 56C, 56D may be formed as an aperture, divot, engraving, color marking, or similar marking. Furthermore, while the reference features 56, 56A, 56B, 56C, 56D are illustrated in the figures as being disposed on the third plate 16, it is also contemplated that the reference features 56, 56A, 56B, 56C, 56D may be disposed on the first and/or second plate(s) 12, 14. The reference features 56, 56A, 56B, 56C, 56D for a given saw blade cartridge may be placed on any combination of the first, second, and/or third plate(s) 12, 14, 16.

Referring to FIGS. 35A and 35B, an alternative configuration for a saw blade 70 any of the saw blade cartridges 10, 110, 210 described above is illustrated. The saw blade 70 includes a blade head 74 with a plurality of teeth 76, 78. The blade head 74 may further be formed with one or more apertures 75. Referring to FIG. 35A, an exemplary blade head 74 including a pair of apertures 75A, 75B is illustrated. Alternatively, FIG. 35B illustrates an exemplary blade head 74 including a three apertures 75A, 75B, 75C. It is contemplated that the blade head 74 may be formed with any number of apertures 75. The apertures 75 may be configured to allow for removal of debris while cutting. It is also contemplated that the apertures 75 may be configured to provide cooling of the blade 70 and/or blade head 74 while cutting. Furthermore, the apertures 75 may be configured to assist in manufacturing the blade 70. For example, when manufacturing the blade 70, the apertures 75 may be machined and/or formed in the blank piece of material from which the blade will be formed. The apertures may then be used during manufacturing as a reference point, such that the blade body 72, blade head 74, and/or teeth 76, 78 may be machined/formed suing the aperture(s) 75 as a reference. For example, the manufacturing process may be setup such that the apertures 75 are identifiable, and the machining tool is programmed to cut and/or grind the blank piece of the material at a location based on the aperture(s) 75 to form the teeth.

Figure 37:
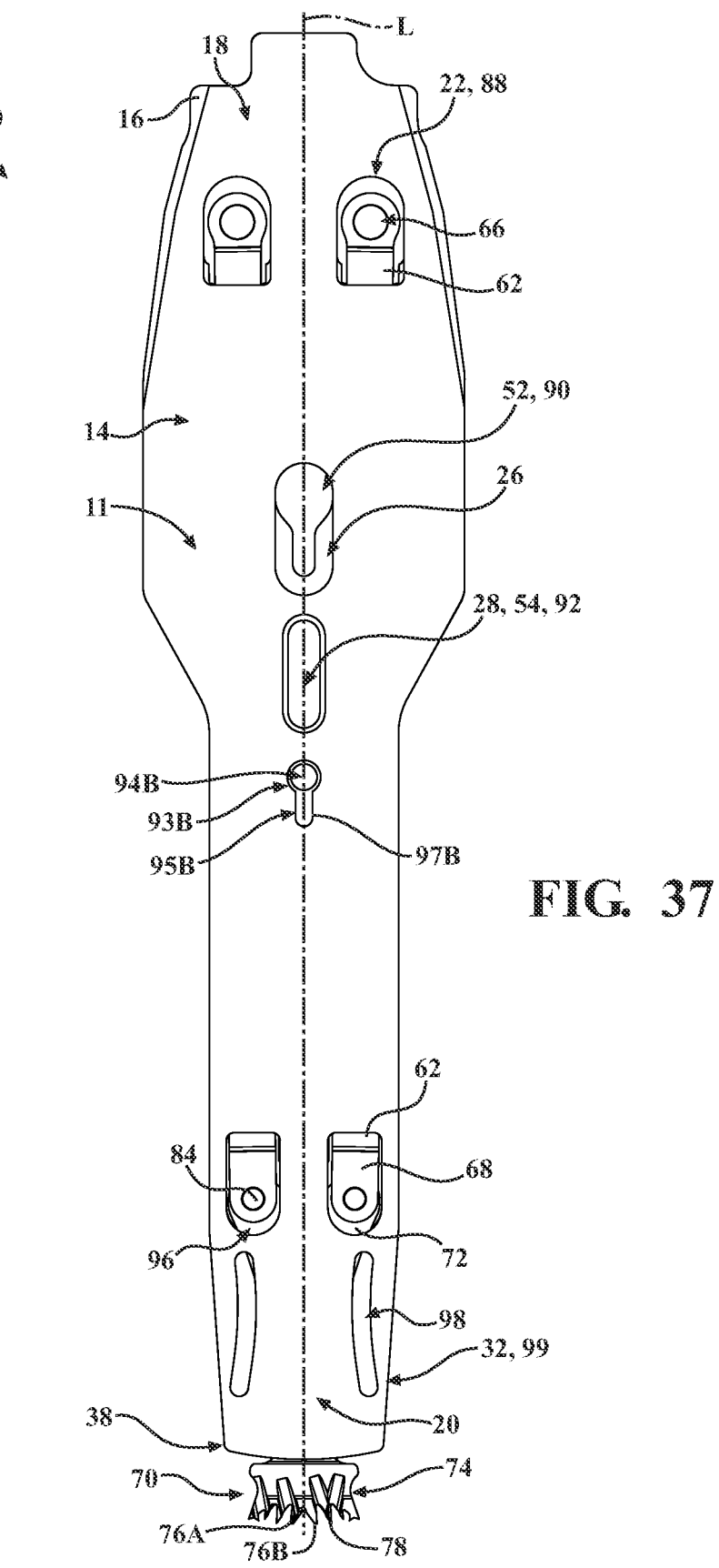
FIG. 37 is a top view of the saw blade cartridge of FIG. 1 including a second configuration of a guide bar including an opening in at least one of a first plate or a second plate, the opening sized and/or shaped to guide a registration tool to a reference feature on the guide bar.
Figure 38:
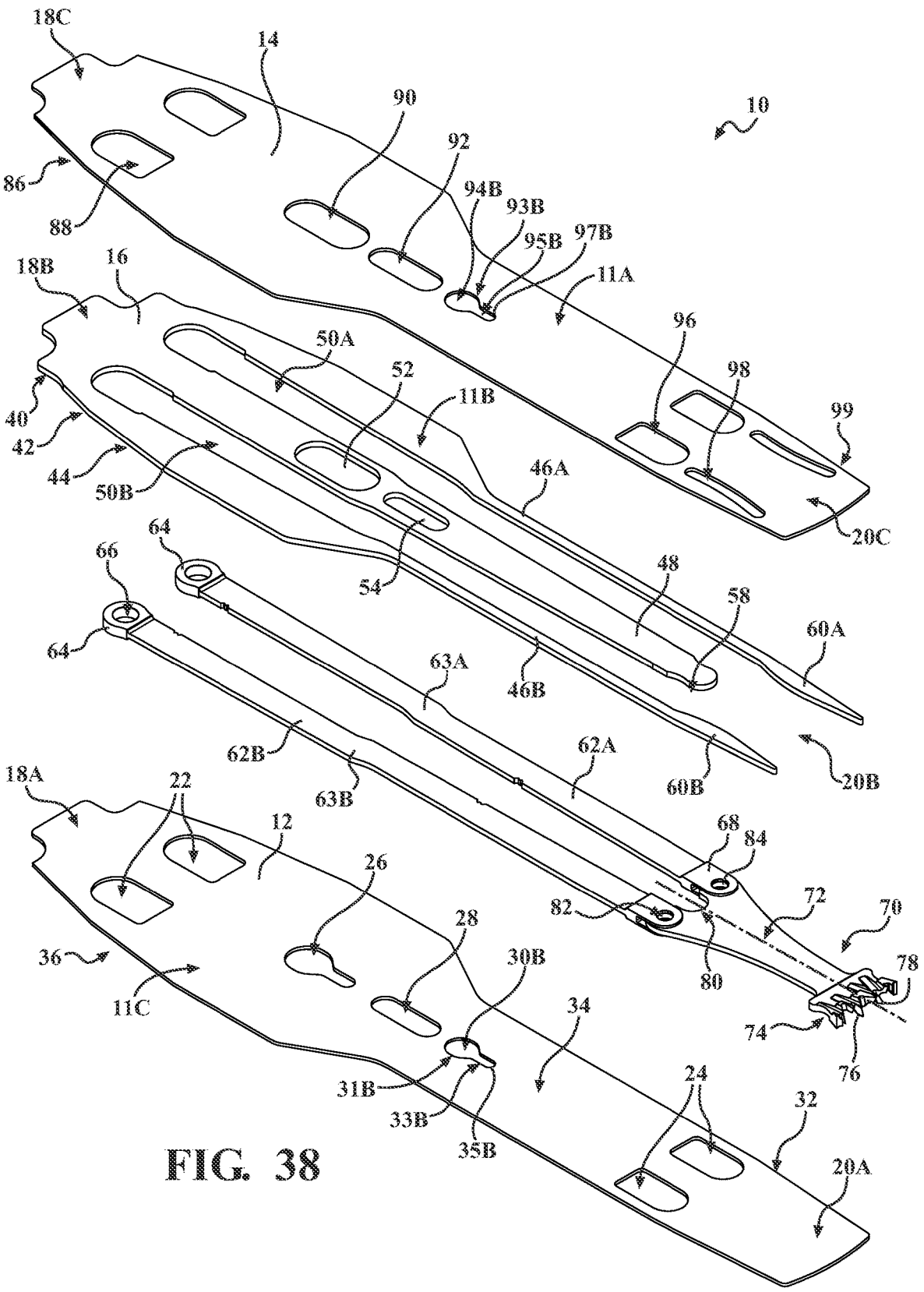
FIG. 38 is an exploded view of the saw blade cartridge of FIG. 37.

Referring to FIGS. 37 to 40, an alternative configuration for an opening 30, 94 in the guide bar 11 of any of the saw blade cartridges 10, 110, 210 described above is illustrated. As described above, either of the first and/or second plates 12, 14 may define an opening 30, 94 to provide access to a reference feature 56 that may be used for identifying and or registering the saw blade cartridges 10, 110, 210 to a navigation system. FIGS. 37 and 38 illustrate a guide bar 11 that may include alternative configuration of an opening 30B, 94B in the first and/or second plate 12, 14. The opening 30B, 94B may be shaped to define a first region 31B, 93B and a second region 33B, 95B. The first region 31B, 93B of the opening 30B, 94B may have a first size and be configured to receive a registration tool 2. The second region 33B, 95B of the opening 30B, 94B may have a second size that is smaller than the size of the first region 31B, 93B. The second region 33B, 95B may further be configured to identify and/or guide the registration tool 2 to a contact point 35B, 97B. The contact point 35B, 97B may be located on the first and/or second plate(s) 12, 14. It is also contemplated that the second region 33B, 95B may further be configured to guide the registration tool 2 to a contact point or reference feature on the third plate 16. For example, in operation, the registration tool 2 may be inserted into first region 31B, 93B of the opening 30B, 94B defined by the first and/or second plate 12, 14. The registration tool may be maneuvered within the opening 30B, 94B from the first region 31B, 93B to the second region 33B, 95B. The second region 33B, 95B may be sized and/or shaped such that the as the registration tool 2 is mover within the opening 30B, 94B, the second region 33B, 95B guides the registration tool 2 to contact point 35B, 97B that may correspond to a reference feature of the saw blade cartridges 10, 110, 210 that is recognizable and/or known by the navigation system. In this configuration of the guide bar 11, it is contemplated that the aperture configuration of the reference feature 56 may be removed from the third plate 16, and as the registration tool 2 is maneuvered within the opening 30B, 94B, the registration tool 2 may be in contact with the surface of the third plate 16. As illustrated in FIGS. 37 and 38, an exemplary configuration of the opening 30B, 94B may comprise a key-shape.

Figure 39:
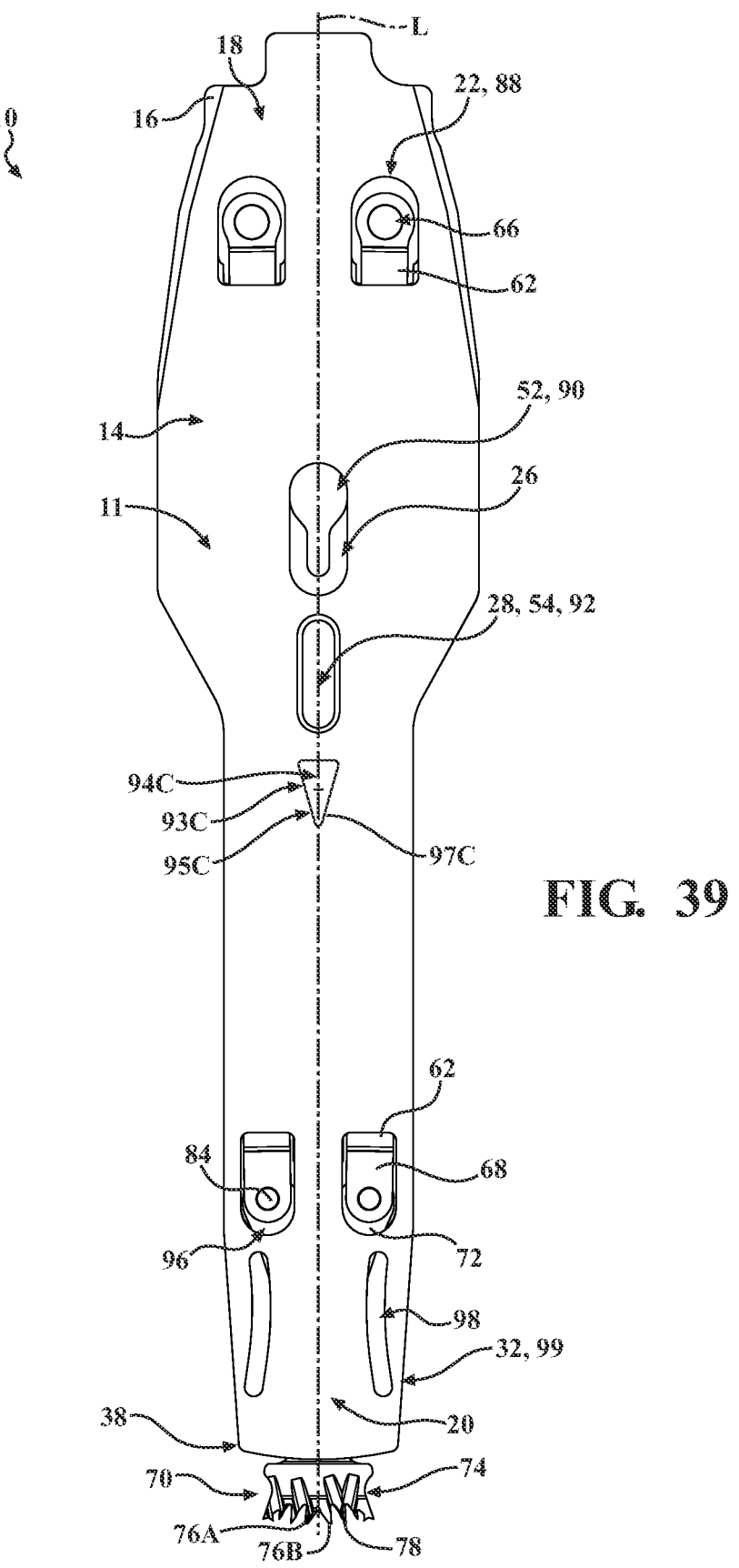
FIG. 39 is a top view of the saw blade cartridge of FIG. 1 including a third configuration of a guide bar including an opening in at least one of a first plate or a second plate, the opening sized and/or shaped to guide a registration tool to a reference feature on the guide bar
Figure 40:
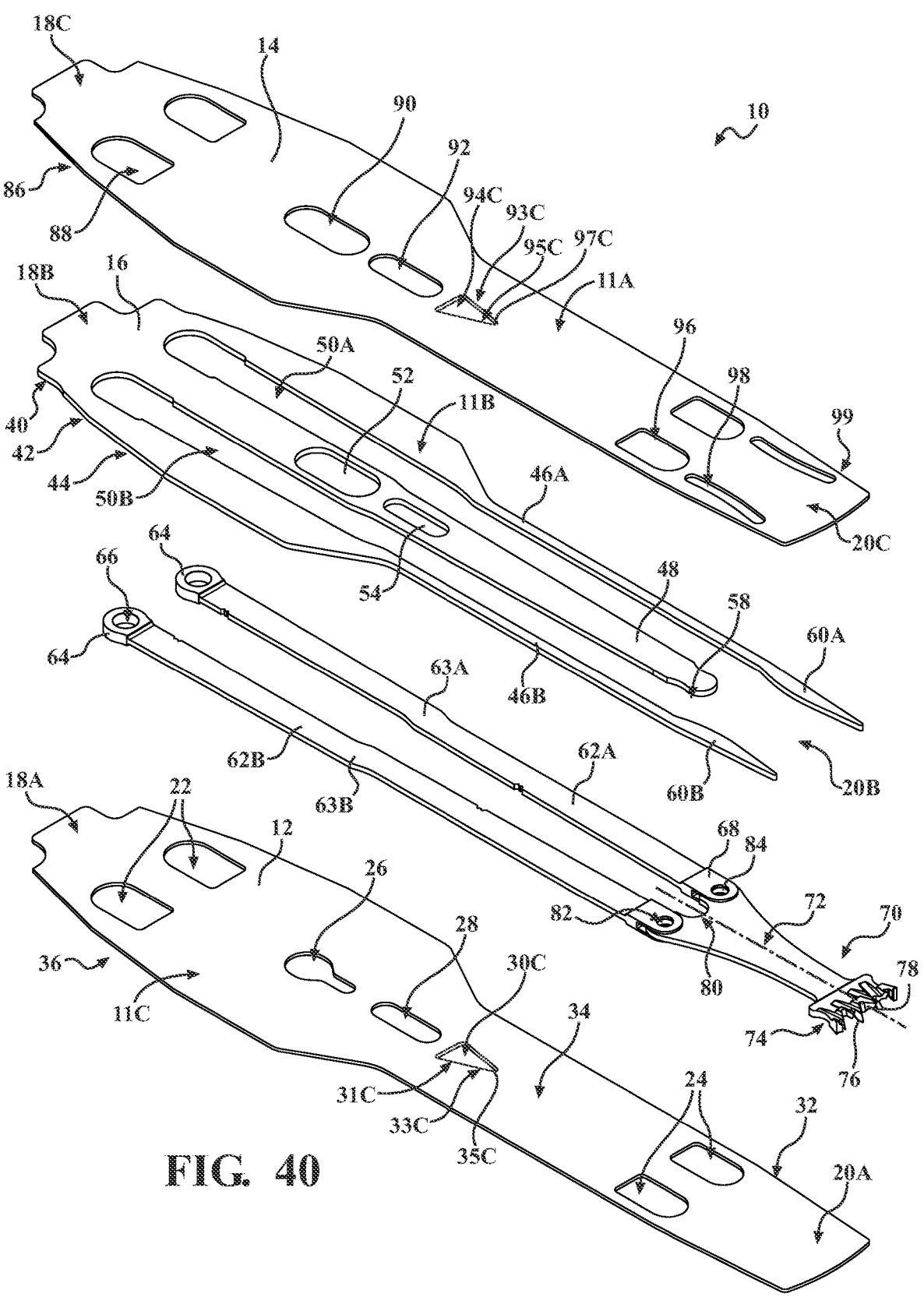
FIG. 40 is an exploded view of the saw blade cartridge of FIG. 39.

Referring a FIGS. 39 and 40, another alternative configuration for an opening 30, 94 in the guide bar 11 of any of the saw blade cartridges 10, 110, 210 described above is illustrated. Similar to the opening(s) 30B, 94B of FIGS. 37 and 38, the configuration of the opening(s) 30C, 94C illustrated in FIGS. 39 and 40 may be shaped to define a first region 31C, 93C and a second region 33C, 95C. The first region 31C, 93C of the opening 30C, 94C may have a first size and be configured to receive a registration tool 2. The second region 33C, 95C of the opening 30C, 94C may have a second size that is smaller than the size of the first region 31C, 93C. The second region 33C, 95C may further be configured to identify and/or guide the registration tool 2 to a contact point 35C, 97C. The contact point 35C, 97C may be located on the first and/or second plate(s) 12, 14. It is also contemplated that the second region 33C, 95C may further be configured to guide the registration tool 2 to a contact point or reference feature on the third plate 16. As illustrated in FIGS. 39 and 40, an exemplary configuration of the opening 30B, 94B may comprise a triangle-shape.

During the course of advancing the saw blade cartridge 10, 110, 210, the saw blade cartridge 10, 110, 210 is exposed to resistive forces. The inner plate 16, 116, 216 provides structural strength to the guide bar 11, 111, 211. This structural strength resists the extent to which the bar 11, 111, 211 would otherwise flex when exposed to these resistive forces. Further reinforcement of the guide bar 11, 111, 211 is provided by the sections of the outer tines 46, 146, 246 that extend forward of the head 58, 158, 258 of the inner tine 48, 148, 248. The lobes 60, 160, 260 and/or tabs 261 provide structural strength to the guide bar 11, 111, 211 at the distal portion 20, 120, 220 of the guide bar 11, 111, 211. This is the portion of the guide bar 11, 111, 211 initially exposed to the resistive forces. The presence of lobes 60, 160, 260 and/or tabs 261 thus further reduces the likelihood that the distal portion 20, 120, 220 of the guide bar 11, 111, 211 will skive or dive. The prevention of the skiving or diving of the distal portion 20, 120, 220 of the guide bar 11, 111, 211 reduces the likelihood that the saw blade cartridge 10, 110, 210 as whole will skive or dive.

A further feature of the saw blade cartridge 10, 110, 210 is that the drive links 62, 162, 262 are, on both sides, encased in the inner plate 16, 116, 216. This means that, if a surgeon holds or touches the sides of the guide bar 11, 111, 211 when the saw blade cartridge 10, 110, 210 is actuated, the surgeon's fingers do not come into contact with the reciprocating driving links 62, 162, 262. At a minimum, this makes it essentially impossible for the drive links 62, 162, 262 to, when moving, tear the glove off the surgeon's fingers. Still another benefit of this construction, is that it facilitates the efficient welding of the side portions of plates 12, 14, 16, 112, 114, 116, 212, 214, 216. This side welding of the plates 12, 14, 16, 112, 114, 116, 212, 214, 216 so as to form side welds along the opposed sides of the guide bar 11, 111, 211 serves to strengthen the guide bar.

For example, the various features of the different configurations of the saw blade cartridge 10, 110, 210 can be combined in any arrangement of the various components.

Likewise, not all configurations of the saw blade cartridge 10, 110, 210 may have all the described features. For example, it is not required that all configurations of the saw blade cartridge 10, 110, 210 include outer tines that extend forward of the inner tine. In yet another example, it may not be necessary that all outer tines include inwardly directed lobes.

Likewise, in some versions of the saw blade cartridge 10, 110, 210, the inner plate 16, 116, 216 may be wholly or partially formed with one or both of the first plate 12, 112, 212 or the second plate 14, 114, 214. Thus, in these versions of the saw blade cartridge 10, 110, 210, once a blank is formed, the blank is machined to define the slots in which the drive rods are seated and that define the perimeter of the tines. Alternatively, the opening- and slot-defining portion of the guide bar may be formed by molding.

In some versions of the saw blade cartridge 10, 110, 210, a single drive link may be all that is needed to pivot the blade head. In some versions of the saw blade cartridge 10, 110, 210 the one or more drive links may not be parallel to the longitudinal axis through the cartridge. Thus, in these versions of the saw blade cartridge 10, 110, 210, the openings in the guide bar through in which elements of the one or more drive links are seated likewise may not be aligned on line that are parallel to the longitudinal axis through the cartridge.

In versions of the saw blade cartridge 10, 110, 210 in which the at least one drive link and the blade are provided with complementary teeth, the guide bar may have a structure different from what has been described. Specifically, the guide bar may be formed so that head are which the blade head is not an integral part of one of the plates forming the bar. In these versions of the saw blade cartridge 10, 110, 210, the structure around which the blade pivots may be a pin mounted to or integral with at least one of the plates that form the bar.

In some versions of the saw blade cartridge 10, 110, 210 two or all three of the plates that form the guide bar may not be three distinct plates that are welded or otherwise secured together. In these alternative versions of the saw blade cartridge 10, 110, 210, the plural plates are machined or molded together as a single unit.

The various shapes of the elements may also vary from what has been described.

Accordingly, it is an object of the appended claims to cover all such variations and modifications that cover the true spirit and scope of the saw blade cartridge 10, 110, 210.

What is claimed is:

1. A saw blade cartridge for use with a surgical device, the saw blade cartridge comprising:
    a guide bar including a distal portion and a proximal portion, the guide bar comprising:
    a first plate;
    a second plate; and
    an inner plate disposed partially between the first and the second plates, the inner plate defining a pivot surface;
    a blade at least partially disposed between the first and the second plates, the blade comprising:
    a blade body including a proximal end and a distal end; and
    a blade head disposed on the distal end of the blade body, the blade head formed with teeth, wherein the proximal end of the blade body abuts the pivot surface;
    wherein the proximal portion defines a proximal end;
    wherein one of the first and second plates define a first outer edge,
    wherein the inner plate defines a second outer edge, the second outer edge extends beyond the first outer edge defined by one of the first and second plates and wherein the second outer edge tapers outwardly from the proximal end to the distal end of the proximal portion such that the second outer edge assists in aligning the saw blade cartridge with the surgical device.

2. The saw blade cartridge of claim 1, wherein the guide bar further defines a longitudinal axis extending between the distal portion and the proximal portion of the guide bar; and
    wherein the second outer edge defines a first taper angle relative to the longitudinal axis between a first point and a second point on the second outer edge; and
    wherein the second outer edge defines a second taper angle relative to the longitudinal axis between the second point and a third point on the second outer edge, the first point being closer to a proximal end of the cartridge than the third point and the second point being disposed between the first point and the third point.

3. The saw blade cartridge of claim 1, wherein the inner plate further comprises a tine extending from a proximal end of the guide bar, the tine defining the pivot surface.

4. The saw blade cartridge of claim 3, wherein the tine is an inner tine, and further comprising a first outer tine and a second outer tine, the first and second outer tines being positioned between the first and second plates and the inner tine being disposed between the first and second outer tines.

5. The saw blade cartridge of claim 4, wherein the first and second outer tines extend closer to the distal end of the guide bar than the inner tine.

6. The saw blade cartridge of claim 4, wherein the first and second outer tines each comprises a distal end;
    wherein the guide bar is configured such that the distal end of each of the first and second outer tines is proximal to a distal end of the first and the second plates; and
    wherein a side defined by the first and the second plates defines an aperture proximal to the distal end of the first and the second plates and distal to the distal end of each of the first and second outer tines, the aperture provides for debris exit.

7. The saw blade cartridge of claim 1, wherein the pivot surface is an arcuate surface; and
    wherein the proximal end of the blade body defining a recess that abuts the pivot surface, such that the blade body is configured to pivot about the pivot surface defined by the inner plate when the blade body is actuated.

8. The saw blade cartridge of claim 7, wherein the teeth define a thickness of the blade head that is equal to or greater than a thickness of the guide bar to allow the insertion of the guide bar into a kerf cut by the blade head.

9. The saw blade cartridge of claim 1, wherein the inner plate extends laterally beyond the outer edge of the first and second plates.

10. The saw blade cartridge of claim 1, wherein at least one of the plates defines a reference feature configured to facilitate determination of a position and/or orientation of the surgical blade with a navigation system.

11. The saw blade cartridge of claim 10, wherein the reference feature is selected from the group comprising an optical marking, a divot, or an aperture.

12. The saw blade cartridge of claim 10, wherein the reference feature comprises a plurality of laser markings; and
    wherein at least one of the plurality of laser markings is positioned on each side of the longitudinal axis.

13. The saw blade cartridge of claim 10, wherein the reference feature is configured to identify the saw blade cartridge to the navigation system, including one or more characteristics of the saw blade cartridge; and
    wherein the characteristic including at least one of the following: a type of the blade, a blade thickness of the blade head, a tooth configuration of the blade head, a length of the guide bar, and/or a width of the guide bar.

14. The saw blade cartridge of claim 1, wherein the inner plate further comprises a reference feature configured to facilitate determination of a position and/or orientation of the surgical blade with a navigation system.

15. A saw blade cartridge for use with a surgical device, the saw blade cartridge comprising:
    a guide bar including a distal portion and a proximal portion, the guide bar comprising:
    a first plate;
    a second plate disposed below the first plate;
    an inner plate disposed partially between the first and the second plates, the inner plate defining a pivot surface;
    a blade comprising:

a blade body including a proximal end and a distal end; and a blade head disposed on the distal end of the blade body and configured to extend from the distal portion of the guide bar, the blade head formed with teeth, wherein the proximal end of the blade body abuts the pivot surface;

wherein the proximal portion defines a proximal end;

wherein the first plate defines a first outer edge;

wherein the inner plate defines a second outer edge;

the guide bar is configured such that the second outer edge extends beyond the first outer edge; and wherein the second outer edge tapers outwardly from the proximal end to the distal end of the proximal portion of the guide bar such that the second outer edge assists in aligning the saw blade cartridge with the surgical device.

16. The saw blade cartridge of claim 15, wherein at least one of the plates defines a reference feature configured to facilitate determination of a position and/or orientation of the surgical blade with a navigation system; and wherein the reference feature is selected from the group comprising an optical marking, a divot, or an aperture.

17. The saw blade cartridge of claim 16, wherein the reference feature is configured to identify the saw blade cartridge to the navigation system, including one or more characteristics of the saw blade cartridge; and wherein the characteristics include at least one of the following: a type of the blade, a blade thickness of the blade head, a tooth configuration of the blade head, a length of the guide bar, and/or a width of the guide bar.

18. A surgical saw system, the system comprising:

a surgical device including a mount, the mount defining a mount surface, and the mount comprising:

a first wall and a second wall extending above the mounting surface, the first and second wall positioned on opposing sides of a longitudinal axis of the mount;

at least one tab disposed on each of the first and second walls, each of the at least one tabs positioned above and extending over the mounting surface;

a saw blade cartridge removably couplable to the mount of the surgical device, the saw blade cartridge comprising:

a guide bar including a distal portion and a proximal portion, the guide bar comprising:

a first plate;

a second plate; and an inner plate disposed partially between the first and the second plates, wherein one of the first and second plates define a first outer edge, wherein the inner plate is configured to define a second outer edge, the second outer edge extends beyond the first outer edge defined by one of the first and second plates;

wherein the first and second walls are tapered relative to the longitudinal axis of the mount to facilitate alignment of the saw blade cartridge along the longitudinal axis; and wherein each of the first and second walls engage the second outer edge of the inner plate and an under surface of each of the at least one tabs engage a top surface of the inner plate.

19. The surgical saw system of claim 18, wherein at least one of the plates defines a reference feature configured to facilitate determination of a position and/or orientation of the surgical blade with a navigation system; and wherein the reference feature is selected from the group comprising an optical marking, a divot, or an aperture.

20. The surgical saw system of claim 19, wherein the reference feature is configured to identify the saw blade cartridge to the navigation system, including one or more characteristics of the saw blade cartridge; and wherein the characteristics include at least one of the following: a type of blade, a blade thickness of a blade head, a tooth configuration of the blade head, a length of the guide bar, and/or a width of the guide bar.

* * * * *